(12) United States Patent
Kashmiri et al.

(10) Patent No.: US 7,763,719 B2
(45) Date of Patent: Jul. 27, 2010

(54) VARIANTS OF HUMANIZED ANTI-CARCINOMA MAB CC49

(75) Inventors: Syed V S. Kashmiri, Gaithersburg, MD (US); Eduardo A. Padlan, Kensington, MD (US); Jeffrey Schlom, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 350 days.

(21) Appl. No.: 11/776,437

(22) Filed: Jul. 11, 2007

(65) Prior Publication Data
US 2008/0050810 A1 Feb. 28, 2008

Related U.S. Application Data

(62) Division of application No. 10/927,433, filed on Aug. 25, 2004, now Pat. No. 7,256,004, which is a division of application No. 09/830,748, filed as application No. PCT/US99/25552 on Oct. 29, 1999, now Pat. No. 6,818,749.

(60) Provisional application No. 60/106,534, filed on Oct. 31, 1998, provisional application No. 60/106,757, filed on Nov. 2, 1998.

(51) Int. Cl.
*C07H 21/04* (2006.01)
(52) U.S. Cl. .................................................. 536/23.53
(58) Field of Classification Search ........................ None
See application file for complete search history.

(56) References Cited

U.S. PATENT DOCUMENTS

| | | | |
|---|---|---|---|
| 4,816,567 A | 3/1989 | Cabilly et al. |
| 5,472,693 A | 12/1995 | Gourlie et al. |
| 5,482,040 A | 1/1996 | Martin, Jr. |
| 5,512,443 A | 4/1996 | Schlom et al. |
| 5,534,254 A | 7/1996 | Huston et al. |
| 5,585,089 A | 12/1996 | Queen et al. |
| 5,688,657 A | 11/1997 | Tsang et al. |
| 5,976,531 A | 11/1999 | Mezes et al. |
| 5,976,845 A | 11/1999 | Mezes et al. |
| 5,994,511 A | 11/1999 | Lowman et al. |
| 6,054,297 A | 4/2000 | Carter et al. |
| 6,180,370 B1 | 1/2001 | Queen et al. |
| 6,333,405 B1 | 12/2001 | Anderson et al. |
| 6,495,137 B1 | 12/2002 | Mezes et al. |
| 7,081,518 B1 | 7/2006 | Pastan et al. |

FOREIGN PATENT DOCUMENTS

| | | |
|---|---|---|
| CA | 2131355 | 3/1996 |
| CA | 2068593 | 7/2003 |
| EP | 0239400 | 9/1987 |
| EP | 0365997 | 5/1990 |
| WO | WO 89/00692 | 1/1989 |
| WO | WO 89/01783 | 3/1989 |
| WO | WO 90/04410 | 5/1990 |
| WO | WO 91/00295 | 1/1991 |
| WO | WO 93/12231 | 6/1993 |
| WO | WO 96/13594 | 5/1996 |
| WO | WO 97/26010 | 7/1997 |
| WO | WO 98/18809 | 5/1998 |
| WO | WO 99/43816 | 9/1999 |
| WO | WO 00/26394 | 5/2000 |
| WO | WO 2004/003155 | 1/2004 |
| WO | WO 2005/021594 | 3/2005 |

OTHER PUBLICATIONS

Overbeek, 1994, "Factors affecting transgenic animal production," Transgenic animal technology, pp. 96-98.*
Wall, 1996 Theriogenology, vol. 45, pp. 57-68.*
Houdebine, 1994, J. Biotech. vol. 34, pp. 269-287, specifically p. 281.*
Kappell, 1992, Current Opinions in Biotechnology, vol. 3, pp. 548-553.*
Cameron, 1997, Mol. Biol. 7, pp. 253-265.*
Mullins, 1993, Hypotension, vol. 22, pp. 630-633.*
Mullins, 1990, Nature, vol. 344, 541-544.*
Hammer, 1990, Cell, vol. 63, 1099-1112.*
Niemann, 1997, Transg. Res. 7, pp. 73-75.*
Mullins, 1989, EMBO J., vol. 8, pp. 4065-4072.*
Taurog, 1988, J. Immunol., vol. 141, pp. 4020-4023.*
Mullins,1996, J. Clin. Invest. vol. 98, pp. S37-S40.*
Rudikoff et al., Proc. Natl. Acad. Sci. USA, 1982, vol. 79, 1979-1983.*
Fundamental Immunology p. 242 (William E. Paul, M.D. ed., 3d ed. 1993).*
Abergel et al., "Crystallographic Studies and Primary Structure of the Antitumor Monoclonal CC49 Fab'," *Proteins: Structure, Function, and Genetics* 17:438-443, 1993.
Adams and Schier, "Generating improved single-chain Fv molecules for tumor targeting," *Journal of Immunological Methods*, 231(1-2):249-260, 1999.
Bending, "Humanization of Rodent Monoclonal Antibodies by CDR Grafting," *Methods: A Companion to Methods in Enzymology*, 8:83-93 (1995).

(Continued)

*Primary Examiner*—Christopher H Yaen
*Assistant Examiner*—Hong Sang
(74) *Attorney, Agent, or Firm*—Klarquist Sparkman, LLP.

(57) ABSTRACT

The invention is directed towards mouse-human chimeric variants of CC49 monoclonal antibodies with minimal murine content. A first aspect of the invention provides CDR variants of humanized monoclonal antibody (HuCC49) in which less than all six (three heavy chain and three light chain) Complementarity Determining Regions (CDRs) of CC49 are present. A second aspect of the invention provides SDR variants of humanized monoclonal antibody (HuCC49) in which only Specificity Determining Regions (SDRs) of at least one CDR from CC49 are present. The invention is also directed towards biotechnological methods of making the variants and therapeutic methods of using the variants.

23 Claims, 23 Drawing Sheets

OTHER PUBLICATIONS

Colcher et al., "Radioimmunolocalization of Human Carcinoma Xenografts with B72.3 Second Generation Monoclonal Antibodies," *Cancer Research* 48:4597-4603, 1988.

De Pascalis et al., "In Vitro Affinity Maturation of a Specificity-Determining Region-Grafted Humanized Anticarcinoma Antibody: Isolation and Characterization of Minimally Immunogenic High-Affinity Variants," *Clinical Cancer Research*, 9(15):5521-5531 (2003).

De Pascalis et al.,"Grafting of "abbreviated" complementarity-determining regions containing specificity-determining residues essential for ligand contact to engineer a less immunogenic humanized monoclonal antibody," *J. Immunol.* 169:3076-3084 (2002).

Divgi et al., "Clinical Comparison of Radiolocalization of Two Monoclonal Antibodies (mAbs) Against the TAG-72 Antigen," *Nucl. Med. Biol.* 21(1):9-15, 1994.

Gonzales et al., "Minimizing immunogenicity of the SDR-grafted humanized antibody CC49 by genetic manipulation of the framework residues," *Mol. Immunol.*, 40:337-349, 2003.

Gonzales et al., "Reducing the potential immunogenicity of humanized CC49 by genetic manipulation of framework residues," *Proceedings of the American Association for Cancer Research*, 44:1118, 2003.

Hakimi et al., "Reduced immunogenicity and improved pharmacokinetics of humanized anti-Tac in cynomolgus monkeys," *J. Immunol.* 147:1352-1359, 1991.

Hand et al., "Potential for Recombinant Immunoglobulin Constructs in the Management of Carcinoma," *Cancer Supplement* 73(3):1105-1113, 1994.

Iwahashi et al., "CDR Substitutions of a Humanized Monoclonal Antibody (CC49): Contributions of Individual CDRs to Antigen Binding and Immunogenicity," *Molecular Immunology* 36:1079-1091, 1999.

Johnson et al., "Analysis of a Human Tumor-associated Glycoprotein (TAG-72) Identified by Monoclonal Antibody B72.3," *Cancer Research* 46:850-857, 1986.

Jones et al., "Replacing the Complementarity-determining Regions in a Human Antibody with those from a Mouse," *Nature* 321:522-525, 1986.

Kashmiri et al, "Generation, Characterization, and in Vivo Studies of Humanized Anticarcinoma Antibody CC49," *Hybridoma* 14(5):461-473, 1995.

Kashmiri et al., "Development of a minimally immunogenic variant of humanized anti-carcinoma monoclonal antibody CC49," *Crit. Rev. Oncol. Hematol.* 38:3-16, 2001.

Kashmiri et al., "SDR grafting—a new approach to antibody humanization," *Methods*, 36:25-34, 2005.

Kashmiri et al., Chapter 21 in *Methods in Molecular Biology*, vol. 248: *Antibody Engineering: Methods and Protocols*, p. 361-376; Lo (ed.), Humana Press, Inc., Tolowa, NJ, 2003.

Mulligan et al., "Phase I Study of Intravenous $^{177}$Lu-labeled CC49 Murine Monoclonal Antibody in Patients with Advanced Adenocarcinoma," *Clinical Cancer Research* 1:1447-1454, 1995.

Muraro et al., "Generation and Characterization of B72.3 Second Generation Monoclonal Antibodies Reactive with the Tumor-associated Glycoprotein 72 Antigen," *Cancer Research* 48:4588-4596, 1988.

Padlan et al., "Identification of Specificity-determining Residues in Antibodies," *The FASEB Journal* 9:133-139, 1995.

Padlan, "A Possible Procedure for Reducing the Immunogenicity of Antibody Variable Domains while Preserving their Ligand-binding Properties," *Molecular Immunology* 28(4/5):489-498, 1991.

Padlan, "Anatomy of the antibody molecule," *Mol. Immunol.* 31:169-217, 1994.

Paul, *Fundamental Immunology*, Raven Press, NY, Ch. 8, p. 242, 1993.

Reichman et al., "Reshaping human antibodies for therapy," *Nature* (London) 332:323-327, 1988.

Rixon et al., "Preferential Use of a H Chain V Region in Antitumor-associated Glycoprotein-72 Monoclonal Antibodies," *The Journal of Immunology* 151(11):6559-6568, 1993.

Rudikoff et al., "Single amino acid substitution altering antigen-binding specificity," *PNAS* 79(6):1979-1983, 1982.

Saldanha et al., "A single backmutation in the human kIV framework of a previously unsuccessfully humanized antibody restores the binding activity and increases the secretion in cos cells," *Mol. Immunol.* 36:709-719, 1999.

Schier et al., "Isolation of picomolar affinity anti-c-erbB-2 single-chain Fv by molecular evolution of the complementarity determining regions in the center of the antibody binding site," *J. Mol. Biol.* 263:551-567, 1996.

Sha et al., "A Heavy-chain Grafted Antibody that Recognizes the Tumor-associated TAG72 Antigen," *Cancer Biotherapy* 9(4):341-349, 1994.

Sharkey et al., "Evaluation of a complementarity-determining region-grafted (humanized) anti-carcinoembryonic antigen monoclonal antibody in preclinical and clinical studies," *Cancer Res.* 55:5935s-5945s, 1995.

Slavin-Chiorini et al., "A CDR-grafted (humanized) domain-deleted antitumor antibody," *Cancer Biother. Radiopharm.* 12:305-316, 1997.

Slavin-Chiorini et al., "Biological Properties of Chimeric Domain-deleted Anticarcinoma Immunoglobulins," *Cancer Research (Supplement)* 55:5957s-5967s, 1995.

Tamura et al., "Structural Correlates of an Anticarcinoma Antibody: Identification of Specificity-determining Residues (SDRs) and Development of a Minimally Immunogenic Antibody Variant by Retention of SDRs Only," *Journal of Immunology* 164(3):1432-1441, 2000.

Wu et al., "Humanization of a murine monoclonal antibody by simultaneous optimization of framework and CDR residues," *J. Mol. Biol.* 294:151-162, 1999.

Xiang et al., "Complementarity Determining Region Residues Aspartic Acid at H55, Serine at H95 and Tyrosines at H97 and L96 Play Important Roles in the B72.3 Antibody-TAG72 Antigen Interaction," *Protein Engineering* 9(6):539-543, 1996.

Xiang et al., "Light-chain framework region residue Tyr71 of chimeric B72.3 antibody plays an important role in influencing the TAG72 antigen binding," *Protein Eng.* 12:417-421, 1999.

Xiang et al., "The Tyrosine Residue at Position 97 in the $V_H$ CDR3 Region of a Mouse/Human Chimeric Anti-Colorectal Carcinoma Antibody Contributes Hydrogen Bonding to the TAG72 Antigen," *Cancer Biotherapy* 8(3):253-262, 1993.

\* cited by examiner

FIG. 2

Light chain

CDR1

| | 24 | 25 | 26 | 27 | c | b | a | d | e | f | 28 | 29 | 30 | 31 | 32 | 33 | 34 |
|---|---|---|---|---|---|---|---|---|---|---|---|---|---|---|---|---|---|
| CC49/HuCC49 | Lys | Ser | Ser | Gln | Ser | Leu | Leu | Tyr | Ser | Gly | Asn | Gln | Lys | Asn | Tyr | Leu | Ala |
| LEN | Lys | Ser | Ser | Gln | Ser | Val | Leu | Tyr | Ser | Ser | Asn | Ser | Lys | Asn | Tyr | Leu | Ala |

CDR2

| | 50 | 51 | 52 | 53 | 54 | 55 | 56 |
|---|---|---|---|---|---|---|---|
| CC49/HuCC49 | Trp | Ala | Ser | Ala | Arg | Glu | Ser |
| LEN | Trp | Ala | Ser | Thr | Arg | Glu | Ser |

CDR3

| | 89 | 90 | 91 | 92 | 93 | 94 | 95 | 96 | 97 |
|---|---|---|---|---|---|---|---|---|---|
| CC49/HuCC49 | Gln | Gln | Tyr | Tyr | Ser | Tyr | Pro | Leu | Thr |
| LEN | Gln | Gln | Tyr | Tyr | Ser | Thr | Pro | Tyr | Ser |

Heavy chain

CDR1

| | 31 | 32 | 33 | 34 | 35 |
|---|---|---|---|---|---|
| CC49/HuCC49 | Asp | His | Ala | Ile | His |
| 21/28'CL | Ser | Tyr | Ala | Met | Ile |

CDR2

| | 50 | 51 | 52 | 53 | 54 | 55 | 56 | 57 | 58 | 59 | 60 | 61 | 62 | 63 | 64 | 65 |
|---|---|---|---|---|---|---|---|---|---|---|---|---|---|---|---|---|
| CC49/HuCC49 | Tyr | Phe | Ser | Pro | Gly | Asn | Asp | Phe | Lys | Tyr | Asn | Glu | Arg | Phe | Lys | Gly |
| 21/28'CL | Trp | Ile | Asn | Ala | Gly | Asn | Asn | Thr | Lys | Asn | Ser | Gln | Lys | Phe | Gln | Gly |

CDR3

| | 95 | 96 | 97 | 98 | 99 | 100 | a | b | 101 | 102 |
|---|---|---|---|---|---|---|---|---|---|---|
| CC49/HuCC49 | Ser | Leu | Asn | Met | Ala | – | – | – | – | Tyr |
| 21/28'CL | Gly | Gly | Tyr | Tyr | Gly | Ser | Ser | Ser | Asn | Tyr |

```
                       .        .        .        .        .        .        .    CDR1   .        .        .        .
LEN                    DIVMTQSPDSLAVSLGERATINC                                              WYQQKPGQPPKLLIY
HuCC49                 DIVMSQSPDSLAVSLGERVTLNC KSSQSLLYSGNQKNYLA                            WYQQKPGQSPKLLIY

CDR2                    .        .        .        .        .        .        .    CDR3   .
LEN                                              GVPDRFSGSGSGTDFTLTISSLQAEDVAVYYC                           FGQGTKLEIK
HuCC49                 WASARES                   GVPDRFSGSGSGTDFTLTISSVQAEDVAVYYC QQYYSYPLT                 FGAGTKLELK
```

B.

```
                       .        .        .        .        .        .        .    CDR1   .        .        .        .
21/28'CL               QVQLVQSGAEVKKPGASVKVSCKASGYTFT                                        WVRQAPGQRLEWMG
HuCC49                 QVQLVQSGAEVKKPGASVKISCKASGYTFT DHAIH        WVKQNPGQRLEWIG

CDR2                    .        .        .        .        .        .        .
                                                                   RVTITRDTSASTAYMELSSLRSEDTAVYYCAR
21/28'CL               YFSPGNDDFKYNERFKG          KATLTADTSASTAYVELSSLRSEDTAVYFCTR
HuCC49

CDR3   .        .        .
21/28'CL               WGQGTLVTVSS
HuCC49                 SLNMAY   WGQGTLVTVSS
```

```
1    gcaagcttccaccATGGATAGCCAGGCCCAGGTGCTCATGCTCCTGCTGCTGTGGGTGAG
     ---------+---------+---------+---------+---------+---------+   60
     cgttcgaaggtggTACCTATCGGTCCGGGTCCGGGTCCACGAGTACGAGGACGACGACACCCACTC 61   CGGCACATGCGGCGGCACATCGTGATGAGCCAGTCTCCAGACTCCCTGGCCGTGTCCCAGGG
     ---------+---------+---------+---------+---------+---------+   120
     GCCGTGTACGCCGCCGTGTAGCACTACTCGGTCAGAGGTCTGAGGGACCGGCACAGGACCC 121  CGAGAGGGTGACTCTGAATTGCAAGTCCAGCCAGTCCCTGCTCTATAGCGGAAATCAGAA
     ---------+---------+---------+---------+---------+---------+   180
     GCTCTCCCACTGAGACTTAACGTTCAGGTCGGTCAGGGACGAGATATCGCCTTTAGTCTT 181  GAACTATCTCGCCTGGTATCAGCAGAAACCAGGGCAGAGCCCTAAACTGCTGATTTACTG
     ---------+---------+---------+---------+---------+---------+   240
     CTTGATAGAGCGGACCATAGTCGTCTTTGGTCCCGTCTCGGATTTGACGACTAAATGAC 241  GGCCATCCGCTAGGGAATCCGGGCGTGCCTGATCGCTTCAGCAGCGGGATCTGGGACAGA
     ---------+---------+---------+---------+---------+---------+   300
     CCGTAGGCGATCCCTTAGGCCGCACGGACTAGCGAAGTCGTCGCCTAGACCCTGTCT 301  CTTCACTCTCTGACAATCAGCAGCGTGCAGGCAGAAGACGTGGCAGTCTATTATTGTCAGCA
     ---------+---------+---------+---------+---------+---------+   360
     GAAGTGAGACTGTTAGTCGTCGCACGTCCGTCTTCTGCACCGTCAGATAATAACAGTCGT 361  GTATTATAGCTATCCCCTCACATTCGGCGCTGGCACCAAGCTGGAACTGAAAcgggccgc
     ---------+---------+---------+---------+---------+---------+   420
     CATAATATCGATAGGGGAGTGTAAGCCGCGACCGTGGTTCGACTTTgccccggcg 421  ggct    424
     ccga
```

```
  1  ctaagcttccaccATGGAGTGGTCCTGGGTCTTCCTCTTCCTCCTGCTGCTGTGGGTGAG  60
     ------------------------------------------------------------
     gattcgaaggtggTACCTCACCAGGACCCAGAAGGAGAAGGACGACGACACCCACTC 61  AGTGCACTCCCAGGTGCAGCTGGTGCAGTCCGGCGCTGAGTCCGGCCGTGTCCCAGGG   120
     ------------------------------------------------------------
     TCACGTGAGGGTCCAGGTCGACCACGTCAGGCCGCGACTCAGGCCGGCACAGGGACCC 121  CGTGAAGATTTCCTGCAAGGCAAGCGGCTACACCTTCACTCTCTATAGCGGAAATCAGAA   180
     ------------------------------------------------------------
     GCACTTCTAAAGGACGTTCCGTTCGCCGATGTGGAAGTGAGAGATATCGCCTTTAGTCTT 181  GAAACAGAATCCTGGACAGCGCCTGGAGTGGATTGGAGATTGGATATATTTCTCCCGGAAACGATGA   240
     ------------------------------------------------------------
     CTTTGTCTTAGGACCTGTCGCGGACCTCACCTAACCTATAAAGAGAGGGCCTTTGCTACT 241  TTTTAAGTACAATGAGAGGTTCAAGGGCAGCTCTCCAGCCTGAGATCCGAGATCCGCCAG   300
     ------------------------------------------------------------
     AAAATTCATGTTACTCTCCAAGTTCCCGTTCGGAGACGTCGGACTCTAGACGGTC 301  CACTGCCTACGTGGAGCTCTCCAGCCTGAGATCTCCAGCCTGAGGATACTGCAGTTCTGCAC   360
     ------------------------------------------------------------
     GTGACGGATGCACCTCGAGAGGTCGGACTCCTAGGCTCGGACTCCTATGACGTCACATGAAGACGTG 361  AAGATCCCTGAATATGGCCTACTGGGGACAGGGAACCCTGGTCACCGTCTCCAGCgccaa   420
     ------------------------------------------------------------
     TTCTAGGGACTTATACCGGATGACCCCTGTCCCTTGGGACCAGTGGCCAGAGGTCGcggtt 421  aactacgggcccat   434
     --------------
     ttgatgcccgggta
```

FIG. 14

HPLC ANALYSIS OF PATIENT REACTIVITY TO CDR SUBSTITUTION VARIANTS OF HuCC49

| COMPETITOR | | | PATIENTS | | | |
|---|---|---|---|---|---|---|
| | CDR SUBSTITUTIONS | ANTIGEN BINDING | DG | CP | EA | DS |
| NONE | --- | | 46.2[b] | 32.2 | 56.8 | 33.5 |
| HuCC49 | --- | +++ | 0 | 1.5 | 0.5 | 0 |
| HuIgG | --- | − | 59.0 | N.D. | 63.6 | 46.4 |
| LIGHT | L3M94 | +/− | 30.2 | 20.3 | 16.4 | 28.9 |
| | L3M96 | − | 39.2 | 31.1 | 42.9 | 35.2 |
| | L3M97 | +++ | 0.6 | 1.3 | 0.7 | 2.4 |
| | L3M94,97 | +/− | 26.5 | 18.2 | 18.6 | 25.6 |
| | L1,2+3M97 | ++ | 21.3 | 17.6 | 23.8 | 17.1 |
| | L1,2+3M94,97 | + | 53.2 | 38.1 | 44.2 | 37.3 |
| HEAVY | 1M32,34 | − | 1.4 | 5.5 | 3.8 | 0.7 |
| | 2M60−62,64 | ++ | 24.4 | 17.9 | 21.8 | 16.5 |
| BOTH | L3M97 H2M60−62,64 | ++++ | 13.0 | 16.1 | 3.9 | 20.1 |
| | L1,2+3M97 H2M60−62,64 | ++ | 33.0 | 30.7 | 24.9 | 32.1 |

FIG. 18

BIODISTRIBUTION OF I.V. ADMINISTERED RADIOLABELED HuCC49 AND VARIANT IN ATHYMIC MICE BEARING LS-174T HUMAN COLON CARCINOMA XENOGRAFTS: PERCENT OF INJECTED DOSE/GRAM

| ANTIBODY | ORGAN | TIMEPOINTS (hr) | | | | |
|---|---|---|---|---|---|---|
| | | 24 | 48 | 72 | 120 | 168 |
| VARIANT | TUMOR | 15.83 | 23.75 | 21.01 | 17.74 | 9.21 |
| | BLOOD | 6.35 | 4.93 | 4.88 | 2.19 | 0.63 |
| | LIVER | 3.39 | 2.14 | 1.46 | 0.91 | 0.32 |
| | SPLEEN | 5.90 | 6.04 | 2.55 | 2.43 | 3.96 |
| | KIDNEY | 2.52 | 1.27 | 1.00 | 0.77 | 0.36 |
| | LUNG | 3.22 | 2.57 | 2.50 | 1.12 | 0.36 |
| HuCC49 | TUMOR | 11.86 | 17.59 | 15.31 | 13.75 | 5.24 |
| | BLOOD | 4.17 | 2.94 | 2.85 | 1.29 | 0.18 |
| | LIVER | 4.77 | 3.05 | 1.41 | 0.70 | 0.12 |
| | SPLEEN | 6.41 | 7.47 | 2.28 | 2.00 | 0.46 |
| | KIDNEY | 1.86 | 0.92 | 0.70 | 0.57 | 0.14 |
| | LUNG | 2.17 | 1.58 | 1.46 | 0.68 | 0.12 |

VARIANTS OF HUMANIZED ANTI-CARCINOMA MAB CC49

PRIORITY CLAIM

This is a division of U.S. patent application Ser. No. 10/927,433, filed Aug. 25, 2004, now U.S. Pat. No. 7,256,004, issued Aug. 14, 2007, which is a division of U.S. patent application Ser. No. 09/830,748, filed Apr. 30, 2001, now U.S. Pat. No. 6,818,749, issued Nov. 16, 2004, which is the §371 U.S. national stage of International Application No. PCT/US99/25552 filed Oct. 29, 1999, which was published in English under PCT Article 21(2), which in turn claims the benefit of U.S. Provisional Application 60/106,534 filed Oct. 31, 1998 and U.S. Provisional Application 60/106,757 filed Nov. 2, 1998, all of which are incorporated herein in their entirety.

BACKGROUND

Antibodies are specific immunoglobulin (Ig) polypeptides produced by the vertebrate immune system in response to challenges by foreign proteins, glycoproteins, cells, or other antigenic foreign substances. The binding specificity of such polypeptides to a particular antigen is highly refined, with each antibody being almost exclusively directed to the particular antigen which elicited it. This specificity resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions do influence the overall domain structure and hence the combining site.

There are two major methods for generating vertebrate antibodies: generation of polyclonal antibodies in situ by mammalian B lymphocytes and generation of monoclonal antibodies in cell culture by B cell hybrids.

To generate antibodies in situ, an animal (such as a mouse or rabbit) is injected with an antigen. Several weeks later, blood is drawn from the animal and centrifuged. The resulting serum contains antibodies against the injected antigen. The resulting antibodies are polyclonal antibodies because they are products of many different populations of antibody producing cells and hence differ somewhat in their precise specificity and affinity for the antigen.

Monoclonal antibodies are produced using hybridoma technology in which an antibody producing cell is fused with a tumor cell that has the capacity for unlimited proliferation. In contrast to polyclonal antibodies, monoclonal antibodies are homogeneous because they are synthesized by a population of identical cells that are derived from a single hybridoma cell.

However, the use of monoclonal antibodies in humans is severely restricted when the monoclonal antibody is produced in a non-human animal. Repeated injections in humans of a "foreign" antibody, such as a mouse antibody, may lead to harmful hypersensitivity reactions, i.e., anti-mouse antibody (HAMA) or an anti-idiotypic, response. The HAMA response makes repeated administrations ineffective due to an increased rate of clearance from the patient's serum and/or allergic reactions by the patient.

Attempts have been made to manufacture human-derived monoclonal antibodies using human hybridomas. Unfortunately, yields of monoclonal antibodies from human hybridoma cell lines are relatively low compared to mouse hybridomas. Additionally, human cell lines expressing immunoglobulins are relatively unstable compared to mouse cell lines, and the antibody producing capability of these human cell lines is transient. Thus, while human immunoglobulins are highly desirable, human hybridoma techniques have not yet reached the stage where human monoclonal antibodies with the required antigenic specificities can be easily obtained.

Thus, antibodies of non-human origin have been genetically engineered to create chimeric or humanized antibodies. Such genetic engineering results in antibodies with a reduced risk of a HAMA response compared to that expected after injection of a human patient with a mouse antibody. For example, chimeric antibodies can be formed by grafting non-human variable regions to human constant regions. Khazaeli et al. (1991), *J. Immunotherapy* 15:42-52. Generally humanized antibodies, are formed by grafting non-human complementarity determining regions (CDRs) onto human framework regions (FRs) (See European Patent Application 0 239 400; Jones et al. (1986), *Nature* (London), 321:522-525; and Reichman et al. (1988), *Nature* (London), 332:323-327). Typically, humanized monoclonal antibodies are formed by grafting all six (three light chain and three heavy chain) CDRs from a non-human antibody into Framework Regions (FRs) of a human antibody. Alternately, Fv antibodies (See U.S. Pat. No. 4,642,334) or single chain Fv (SCFV) antibodies (See U.S. Pat. No. 4,946,778) can be employed to reduce the risk of a HAMA response.

However, these modified antibodies still retain various non-human light and heavy chain variable regions: the chimeric, Fv and single chain Fv antibodies retain entire non-human variable regions and CDR-grafted antibodies retain CDR of non-human origin. Such non-human regions can elicit an immunogenic reaction when administered to a human patient. Thus, many humanized MAbs remain immunogenic in both subhuman primates and in humans, with the humoral response of the host directed towards the variable region of these MAb (Hakimi et al. (1991), *J. Immunol.*, 147:1352-1359; Stephens et al. (1995), *Immunology*, 85:668-674; Singer et al. (1993), *J. Immunol.*, 150:2844-2857; and Sharkey et al. (1995), *Cancer Res.* 55:5935s-5945s).

One known human carcinoma tumor antigen is tumor associated glycoprotein-72 (TAG-72), as defined by monoclonal antibody B72.3 (See Thor et al., (1986) *Cancer Res.*, 46:3118-3124; and Johnson et al., (1986), *Cancer Res.*, 46:850-85). TAG-72 is associated with the surface of certain tumor cells of human origin.

Numerous murine monoclonal antibodies have been developed which have binding specificity for TAG-72. Exemplary murine monoclonal antibodies include the "CC" (colon cancer) monoclonal antibodies, which are a library of murine monoclonal antibodies developed using TAG-72. Certain CC antibodies have been deposited with the ATCC, including CC49 (ATCC No. HB 9459). Monoclonal antibody (MAb) CC49 is a second-generation antibody of B72.3 that reacts with the pancarcinoma tumor-associated antigen, TAG-72. Radiolabeled MAb CC49 has been shown to target tumor in both animal models and in ongoing radioimmunotherapeutic and raiodimmunodiagnostic clinical trials. (Divgi et al. (1994) *Nucl. Med. Biol.*, 21:9-15; Meredith et al. (1994), *J. Nucl. Med.*, 35:1017-1022; Mulligan et al. (1995), *Clin. Cancer Res.*, 1:1447-1454; Arnold et al. (1992), *Ann. Surgery*, 216:627-632)The potential clinical utility of MAb CC49 is evident both from animal studies and ongoing clinical trials with the antibody. However, patients administered MAb CC49 do generate HAMA responses (Divgi et al, (1994) *Nuc. Med. Biol.*, 21:9-15); Mulligan et al., (1995) *Clin. Cancer Res.*, 1:1447-1454).

A humanized monoclonal antibody (HuCC49) has been formed by grafting hypervariable regions from monoclonal antibody CC49 into variable light ($V_L$) and variable heavy ($V_H$) frameworks of human monoclonal antibodies LEN and 21/28'CL, respectively, while retaining murine framework residues required for integrity of the antigen combining-site structure. (See, Kashmiri et al., (1995) *Hybridoma*, 14(5): 461-473). This HuCC49 was shown to bind the TAG-72 antigen, albeit with a lower affinity, and demonstrated equivalent tumor targeting in animal models bearing human tumor xenografts.

It has been shown that not all residues of CDRs are critical in the complementarity of antigen/antibody surfaces. Known structures of the antigen-antibody complexes suggests that only 20-33% of CDR residues are involved in antigen contact (Padlan, (1994) *Mol. Immunol.*, 31: 169-217). A comprehensive analysis of the available data of the sequences and the three dimensional structure of antibody combining sites has helped identify CDR residues that may be most critical in the antigen antibody interaction (Padlan et al., (1995) *FASEB J.*, 9:133-139). These residues are designated as specificity determining residues (SDRs). Specificity determining residues vary between antibodies.

SUMMARY

The invention is directed towards mouse-human chimeric variants of CC49 monoclonal antibodies with minimal murine content which elicit minimal adverse responses when administered to a human patient. The invention is also directed towards biotechnological methods of making the variants and therapeutic methods of using the variants.

A first aspect of the invention provides CDR variants of humanized monoclonal antibody (HuCC49) in which less than all six (three heavy chain and three light chain) Complementarity Determining Regions (CDRs) of CC49 are present. A second aspect of the invention provides SDR variants of humanized monoclonal antibody (HuCC49) in which only Specificity Determining Regions (SDRs) of at least one CDR from CC49 are present. Surprisingly, the CC49 variants of the invention have the same or similar binding affinity as humanized CC49 monoclonal antibody which includes all six (three heavy chain and three light chain) CDRs.

In particular, the invention relates to variants of HuCC49 in which either L-CDR1 or L-CDR2, or both, are from a human monoclonal antibody (LEN) (LEN L-CDR1 and LEN L-CDR2 correspond to SEQ ID NOs: 7 and 8, respectively). These variants of HuCC49 have the substantially the same affinity constant as HuCC49, or show only a two fold lower relative affinity than that of HuCC49.

Other suitable variants include corresponding human residues at position 97 of the light chain in addition to a substitution of L-CDR1 and/or L-CDR2 from CC49 with the corresponding CDRs from a human antibody. In another embodiment, the variant includes a substitution at position 97 on the light chain in addition to a substitution of L-CDR1 and/or L-CDR2 from CC49 with the corresponding CDRs from a human antibody in combination with substitutions at positions 60, 61, 62 and 64 on the heavy chain. In another embodiment, the variant includes a substitution at position 97 on the light chain in combination with substitutions at positions 60, 61, 62 and 64 on the heavy chain.

BRIEF DESCRIPTION OF THE FIGURES

FIG. 2 shows a comparison of the CDR sequences of murine MAb CC49 and humanized MAb HuCC49 with the corresponding CDR sequences of human MAbs LEN and 21/28'CL. Amino acid residues are numbered using the convention of Kabat et al. The underlined numbers indicate the specificity determining residues (SDRs). CDR1, CDR2 and CDR3 within the light chain of HuCC49 and CC49 correspond to SEQ ID NOs: 1-3, respectively. CDR1, CDR2 and CDR3 within the heavy chain of HuCC49 and CC49 correspond to SEQ ID NOs: 4-6, respectively. CDR1, CDR2 and CDR3 within the light chain of human antibody LEN correspond to SEQ ID NOs: 7-9, respectively. CDR1, CDR2 and CDR3 within the heavy chain of human antibody 21/28°CL correspond to SEQ ID NOs: 10-12, respectively.

Figure 10:
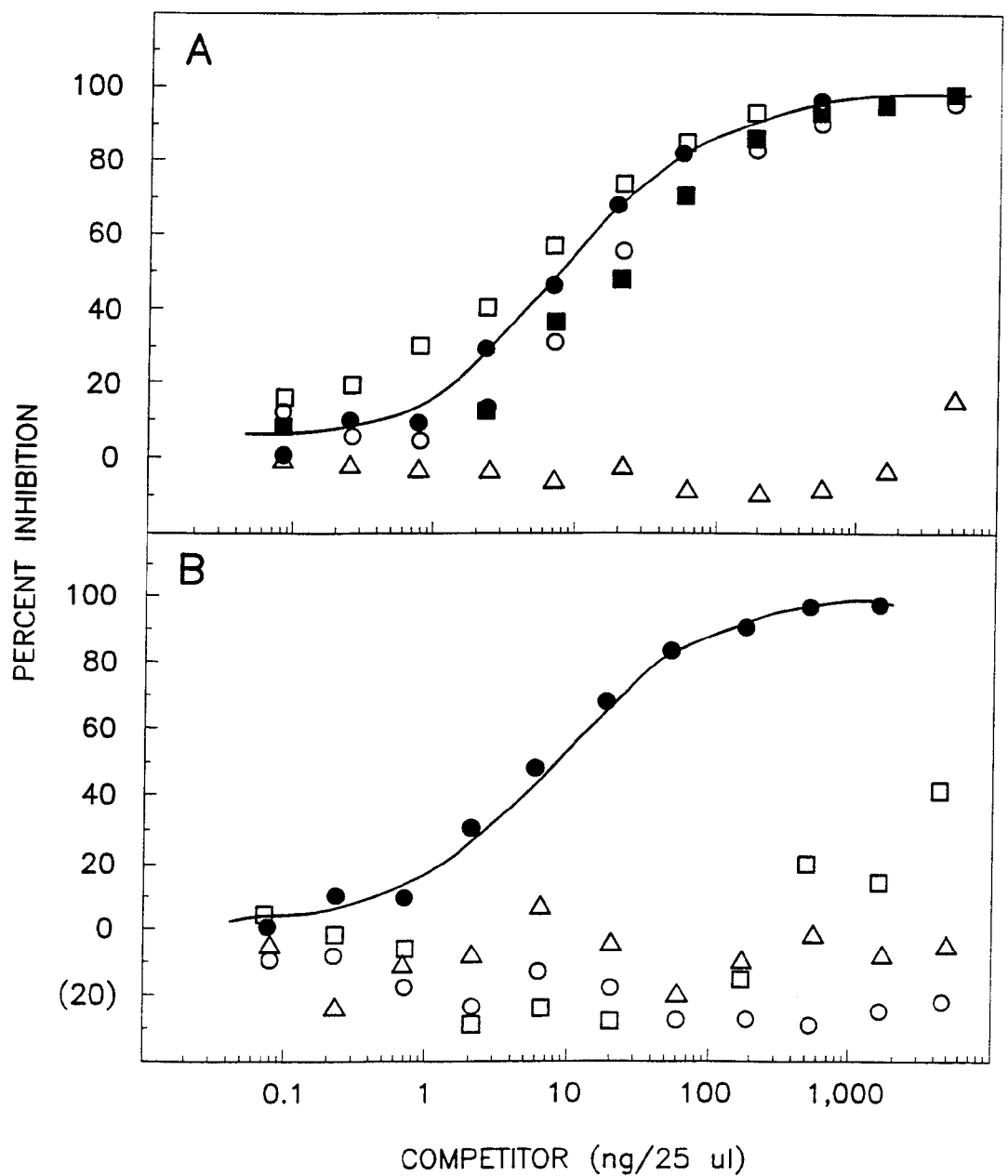

FIG. 10 shows an analysis of human anti-idiotypic antibodies to HuCC49 variants using a competative RIA by HPLC methodology. A patient's anti-idiotypic response to CC49 was characterized using purified parental HuCC49 and CDR variants as competitors with $^{125}$I-HuCC49. The inability of a variant to inhibit complex formation of the patient's sera with the $^{125}$I-HuCC49 indicates that the CDR replaced from the variant was immunogenic to the patient. In panel A, the competitors were: HuCC49, L-1, L-2, L-3, L-1,2. In panel B, the competitors were: H-1, H-2 and H-3.

FIG. 11 shows the amino acid sequences of $V_L$ frameworks of human MAb LEN (SEQ ID NOs: 33-36) and humanized $V_L$ of CC49 (HuCC49) (SEQ ID NO: 13) in panel A. Panel B shows the amino acid sequences of $V_H$ frameworks of human MAb 21/28'CL (SEQ ID NOs: 37-40) and humanized $V_H$ of CC49 (HuCC49) (SEQ ID NO: 14). Framework residues that are deemed to be important in maintaining the combining site structure of CC49 are marked by an asterisk.

FIG. 12 shows the nucleotide sequence of HuCC49 variable light ($V_L$) (SEQ ID NO: 41 and SEQ ID NO: 42) and variable heavy ($V_H$) region (SEQ ID NO: 43 and SEQ ID NO: 44) genes in panels A and B, respectively. Sequences of flanking oligomers that do not encode the variable region domains or their leader peptides are shown in lowercase letters. The $V_L$ region (A) is encoded by nucleotides from positions 74 to 412, while nucleotides from position 70 to 415 (B) comprise the $V_H$ region. The four overlapping oligomers depicted by long arrows in FIG. 12A are represented by SEQ ID NOs: 19-22. The four overlapping oligomers depicted by long arrows in FIG. 12B are represented by SEQ ID NOs: 15-18.

Figure 13:
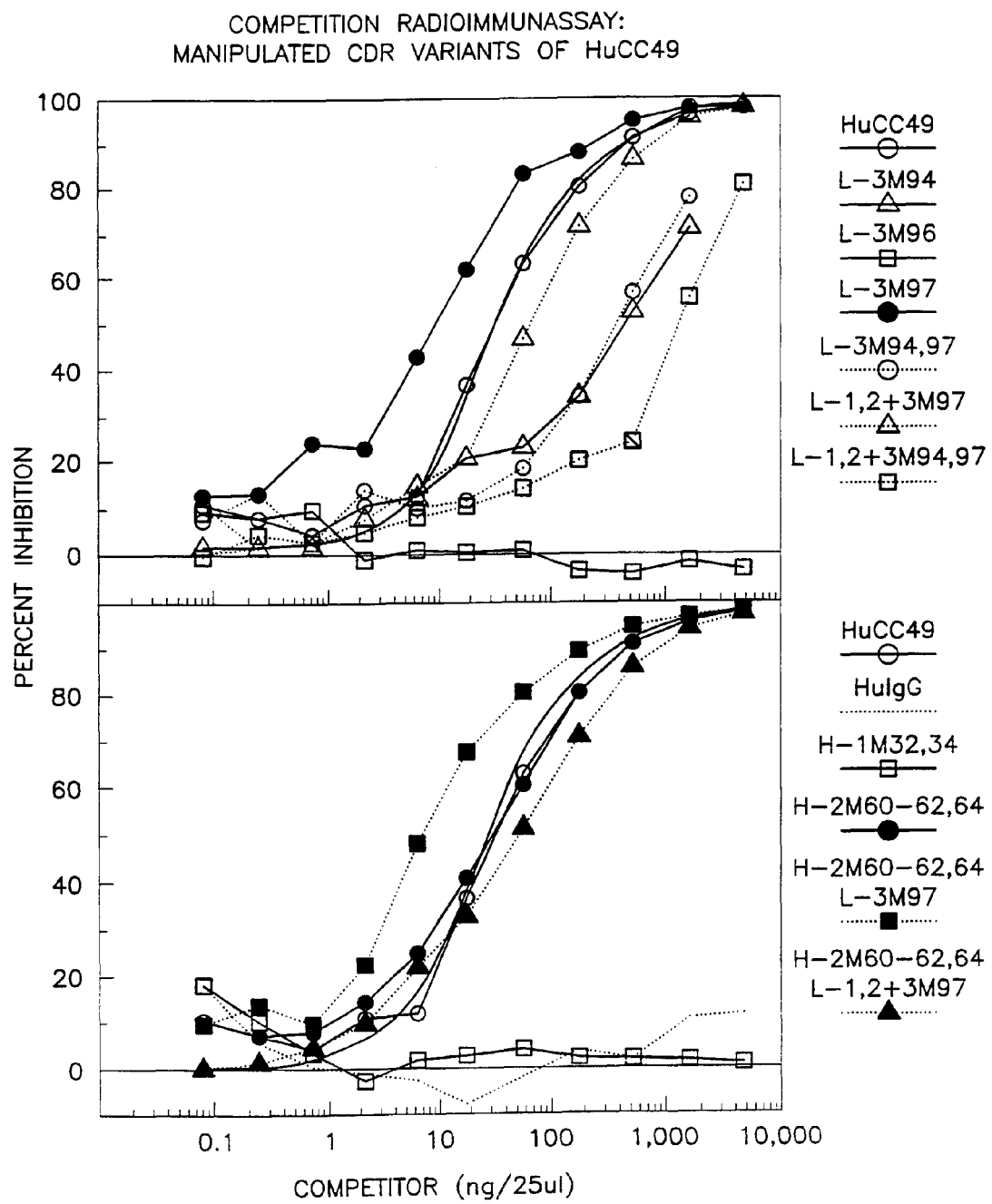

FIG. 13 is a graph of the results of a competition assay using variants of HuCC49.

FIG. 14 shows the results of an HPLC analysis of patient reactivity to variants of HuCC49. Competitors were at 5 Tg per reaction. The values are the percent of complexes, the higher molecular weight species, resolved by size-exclusion chromatography. Complex formation indicates removal of the epitope recognized by the patient's antibody. Inhibition of complex formation indicates that the immunogenic epitope is still present in the HuCC49 variant.

Figure 15:
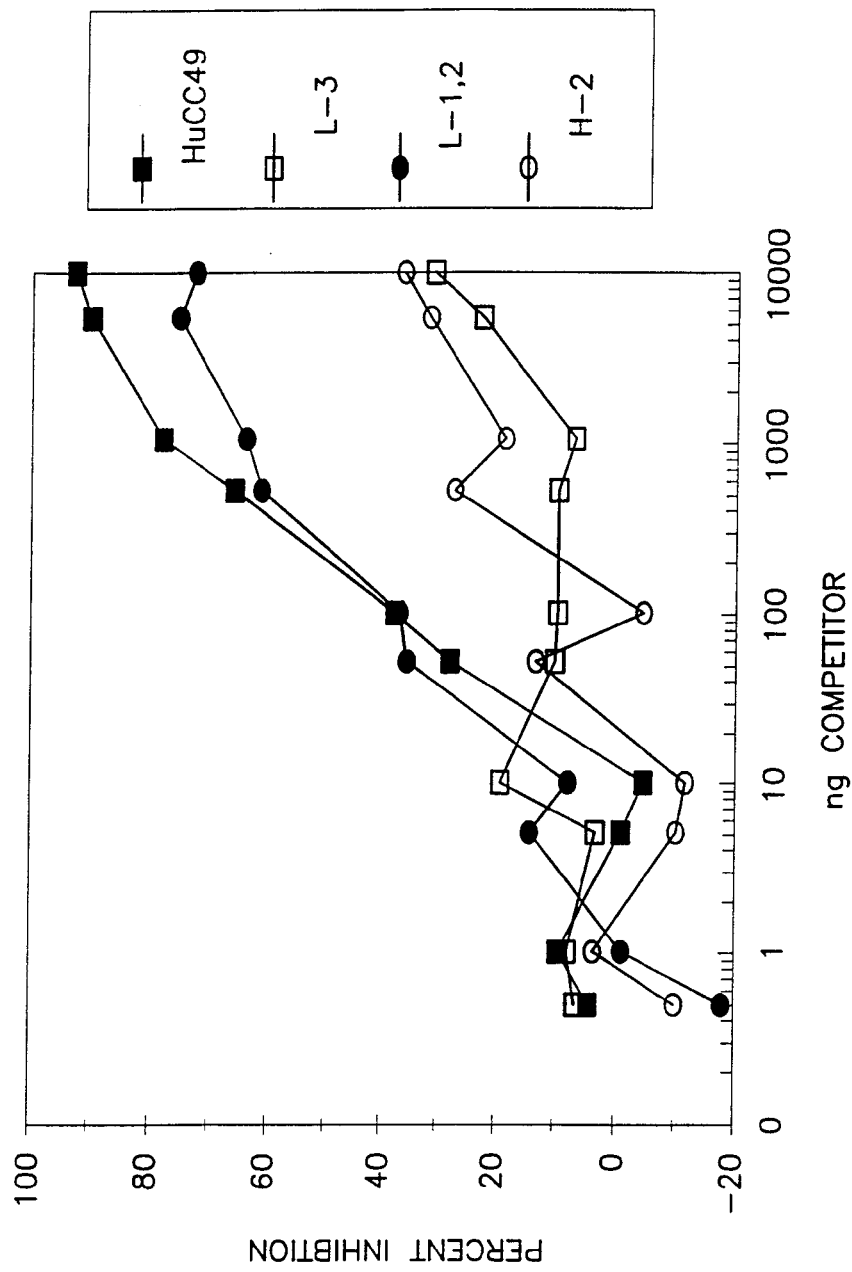

FIG. 15 is a graph showing the comparison of patient reactivity with HuCC49 and various variants thereof.

Figure 16:
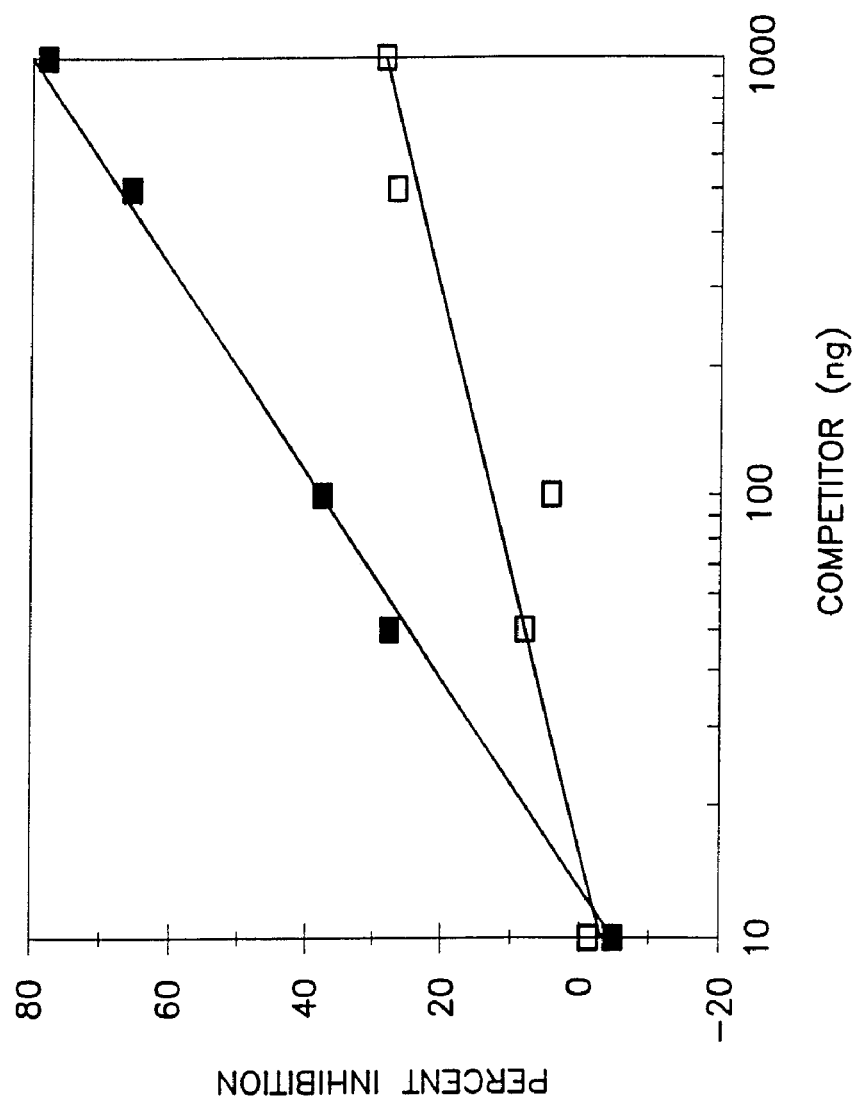

FIG. 16 is graph showing the immunoreactivity of variant $^{97}L_{1,2}/^{60-62,64}H$.

Figure 17:
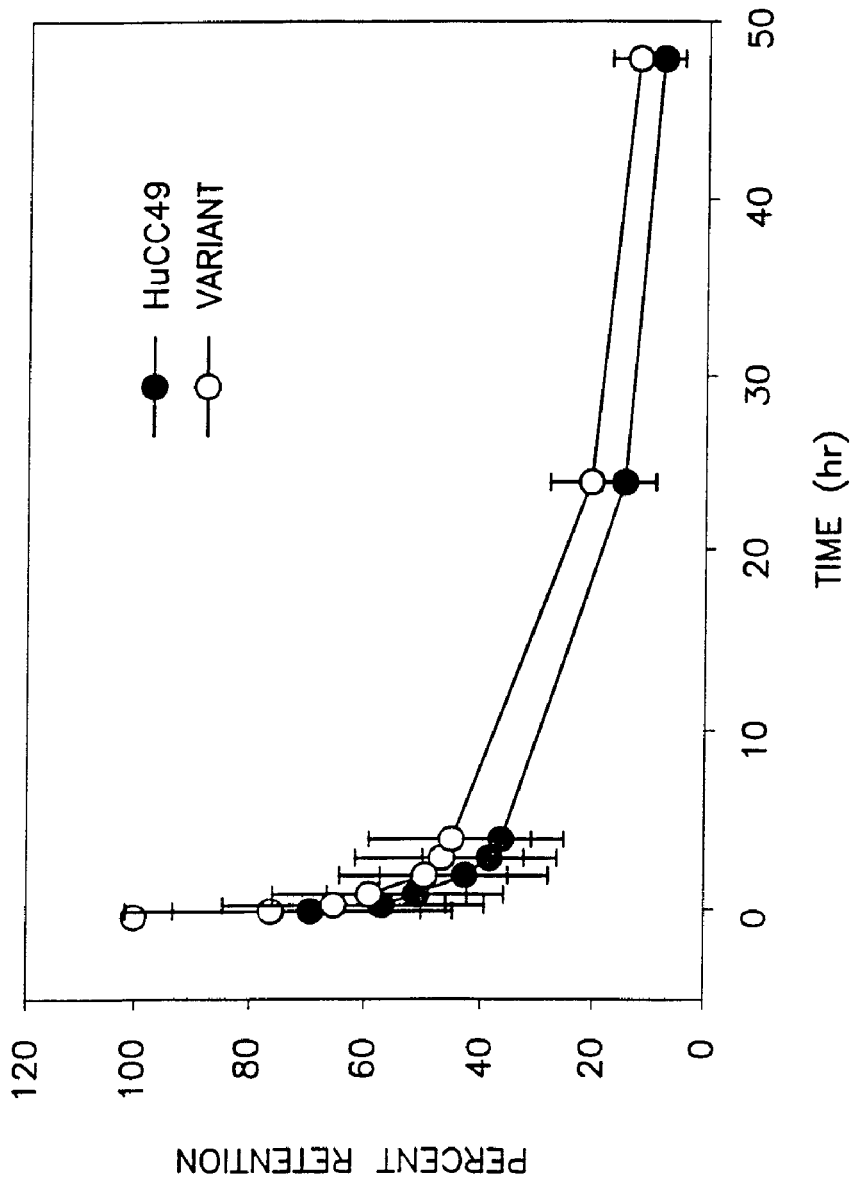

FIG. 17 is a graph of the pharmacokinetics of plasma retention of HuCC49 and a variant thereof.

FIG. 18 is a table showing the biodistribution of i.v. administered radiolabeled HuCC49 and variants in athymic mice bearing LS-174T human colon carcinoma xenografts. Athymic mice bearing LS-174T human colon carcinoma xenografts (s.c.) were coinjected with 1.4TCi of $^{131}$I-HuCC49 and 4.4 of $^{125}$I-Variant. The mice were sacrificed at the timepoints indicated, the organs harvested, wet-weighed and the radioactivity detected in a K-scintillation counter. The percent weight injected dose per gram for each tissue was calculated. The standard error of the mean was also calculated and were 0.06% ID/g or less.

Figure 19:
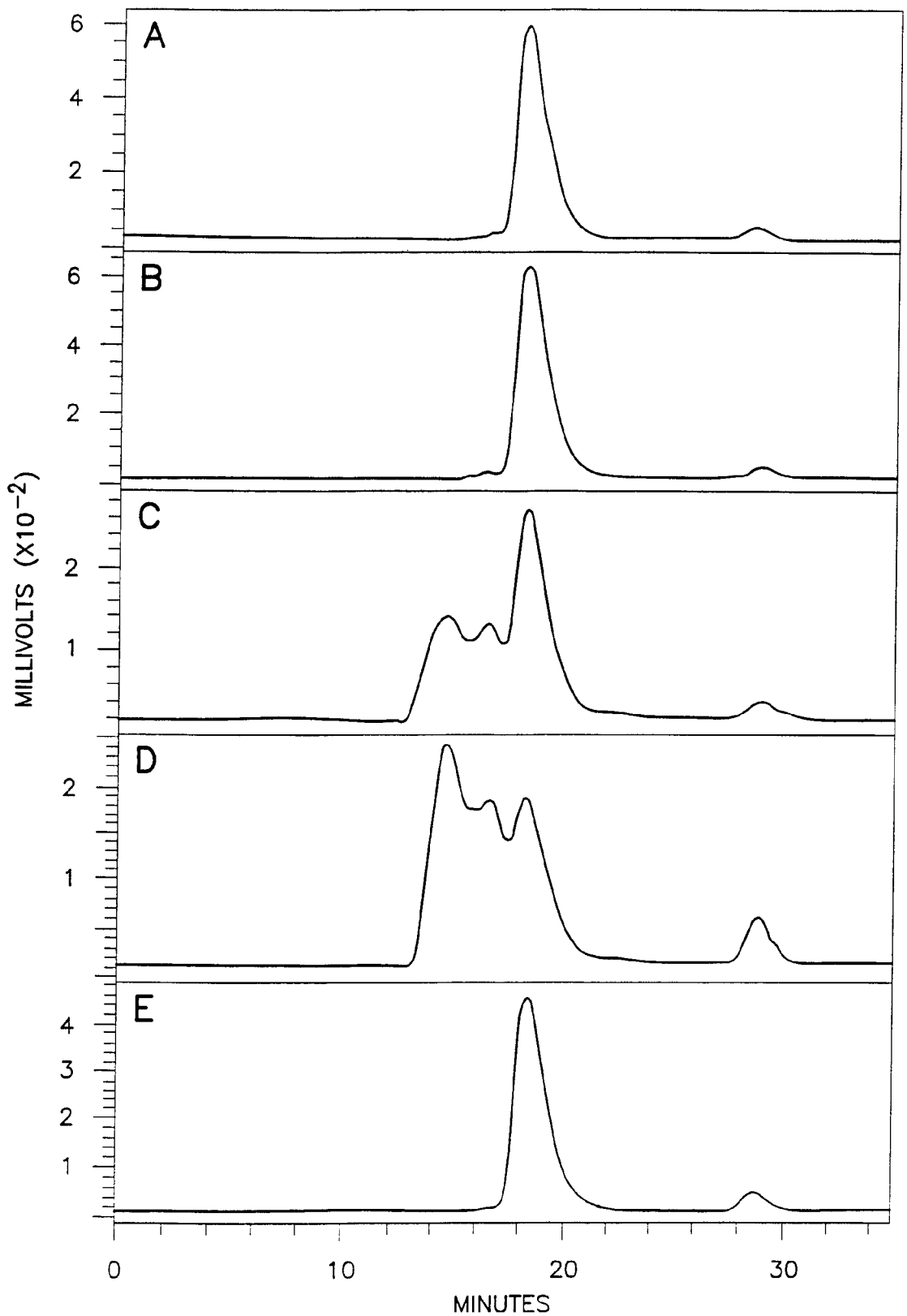

FIG. 19. HPLC analysis of patient HAMA following intravenous injection of $^{177}$LU-CC49.

Figure 20:
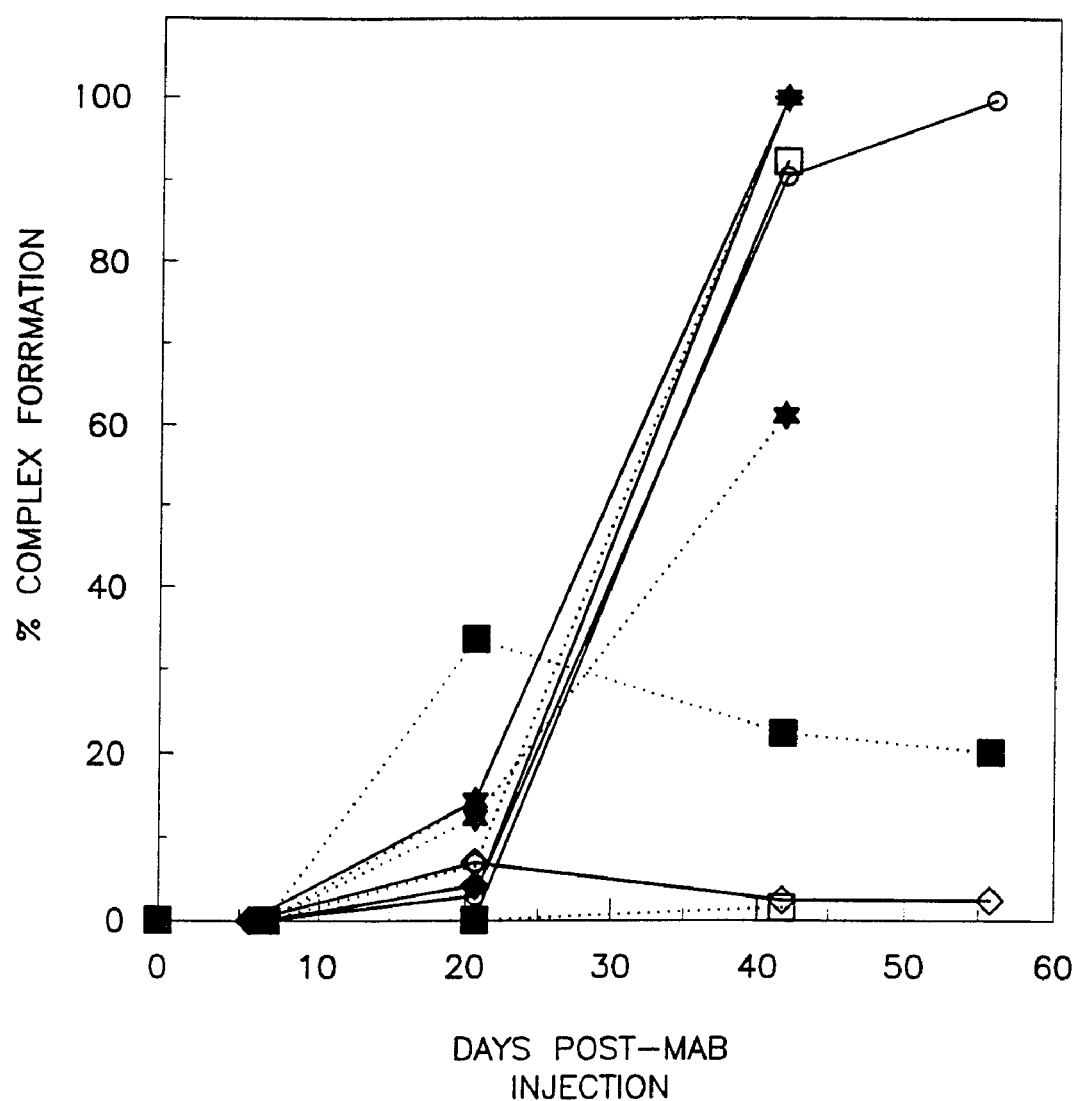
Figure 21:
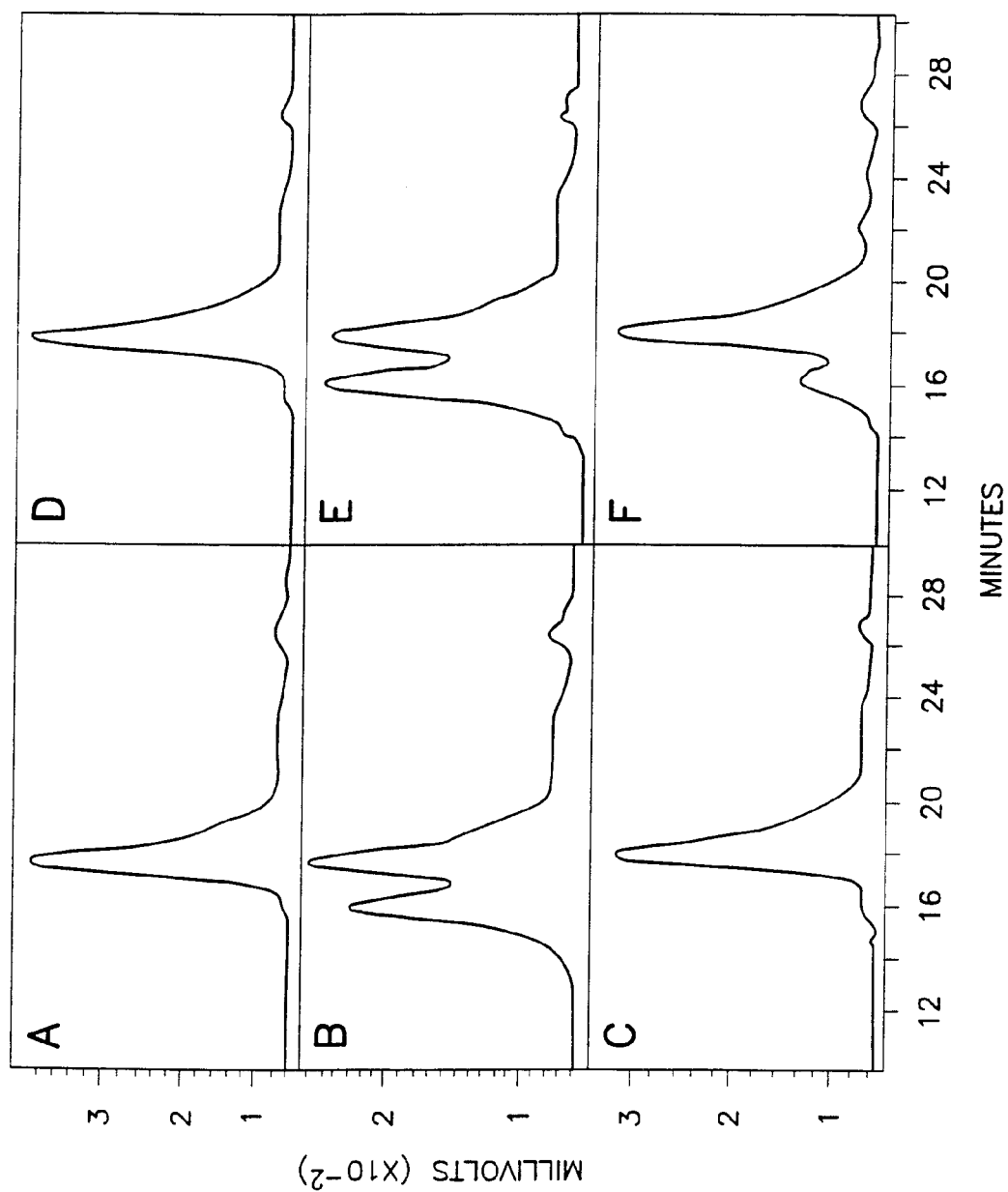

FIG. 20. HPLC analysis of patient' humoral response to the variable region of MAb CC49. The percent complex formation has been plotted versus time for (solid lines) patients DS (○), LW (□), JJ (Δ), DG (●), LJ (■), TD(▲); (dotted lines) JG (○), RW (□), JM A), EA (●), CP (■), LQ (▲);

FIG. 21. Detection of patient anti-idiotypic antibody response to murine CC49.

Figure 22:
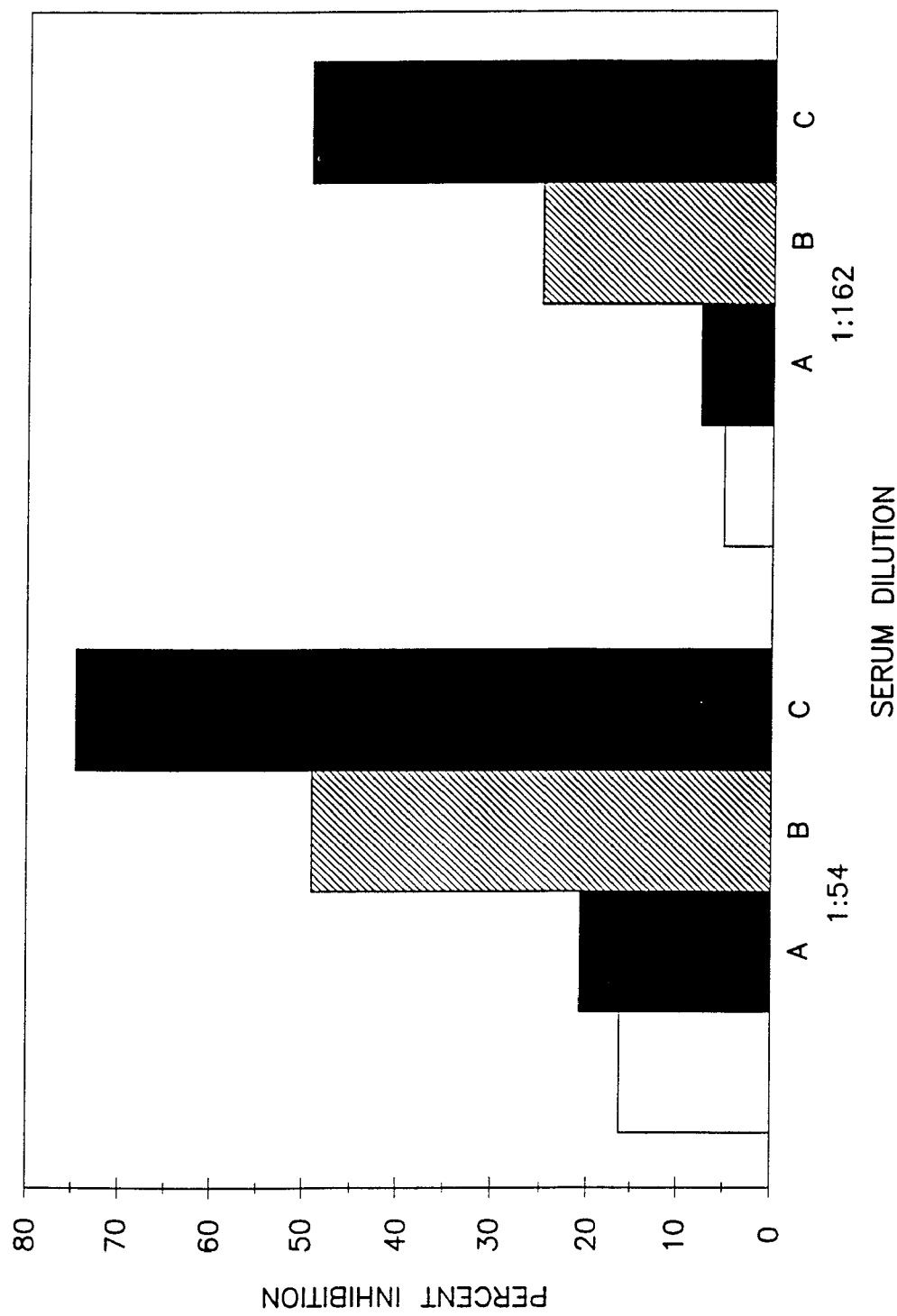

FIG. 22. HPLC analysis demonstrating CDR specificity of patient LQ.

SEQUENCE LISTING

The nucleic and amino acid sequences listed in the accompanying sequence listing are shown using standard letter abbreviations for nucleotide bases and three letter code for amino acids, as defined in 37 C.F.R. 1.822. In the accompanying sequence listing:

SEQ ID NO: 1 shows the amino acid sequence of CDR1 from the light chain of murine antibody CC49 and humanized antibody HuCC49.

SEQ ID NO: 2 shows the amino acid sequence of CDR2 from the light chain of murine antibody CC49 and humanized antibody HuCC49.

SEQ ID NO: 3 shows the amino acid sequence of CDR3 from the light chain of murine antibody CC49 and humanized antibody HuCC49.

SEQ ID NO: 4 shows the amino acid sequence of CDR1 from the heavy chain of murine antibody CC49 and humanized antibody HuCC49.

SEQ ID NO: 5 shows the amino acid sequence of CDR2 from the heavy chain of murine antibody CC49 and humanized antibody HuCC49.

SEQ ID NO: 6 shows the amino acid sequence of CDR3 from the heavy chain of murine antibody CC49 and humanized antibody HuCC49.

SEQ ID NO: 7 shows the amino acid sequence of CDR1 from the light chain of human antibody LEN SEQ ID NO: 8 shows the amino acid sequence of CDR2 from the light chain of human antibody LEN SEQ ID NO: 9 shows the amino acid sequence of CDR3 from the light chain of human antibody LEN SEQ ID NO: 10 shows the amino acid sequence of CDR1 from the heavy chain of human antibody 21/28'CL SEQ ID NO: 11 shows the amino acid sequence of CDR2 from the heavy chain of human antibody 21/28'CL SEQ ID NO: 12 shows the amino acid sequence of CDR3 from the heavy chain of human antibody 21/28'CL SEQ ID NO: 13 shows amino acid sequence of the $V_L$ domain of the humanized murine antibody HuCC49.

SEQ ID NO: 14 shows amino acid sequence of the $V_H$ domain of the humanized murine antibody HuCC49.

SEQ ID NOs: 15-32 show several synthetic oligonucleotides useful as probes and/or primers.

SEQ ID NOs: 33-36 show amino acid sequences of consecutive portions of the framework of the $V_L$ domain of the human antibody LEN.

SEQ ID NOs: 37-40 shows amino acid sequences of consecutive portions of the framework of the $V_H$ domain of the human antibody 21/28'CL.

SEQ ID NO: 41 show the nucleic acid sequence including the $V_L$ domain of the humanized murine antibody HuCC49 together with flanking oligomers.

SEQ ID NO: 42 shows the nucleic acid sequence complementary to SEQ ID NO: 41.

SEQ ID NO: 43 shows the nucleic acid sequence including the $V_H$ domain of the humanized murine antibody HuCC49 together with flanking oligomers.

SEQ ID NO: 44 shows the nucleic acid sequence complementary to SEQ ID NO: 43.

DEFINITIONS

Prior to setting forth the invention, definitions of certain terms which are used in this disclosure are set forth below:

Antibody: This refers to single chain, two-chain, and multi-chain proteins and glycoproteins belonging to the classes of polyclonal, monoclonal, chimeric and hetero immunoglobulins (monoclonal antibodies being preferred); it also includes synthetic and genetically engineered variants of these immunoglobulins. "Antibody fragment" includes Fab, Fab', F(ab')$_2$, and Fv fragments, as well as any portion of an antibody having specificity toward a desired target epitope or epitopes.

Chimeric antibody: This refers to an antibody which includes sequences derived from two different antibodies, which typically are of different species. Most typically, chimeric antibodies include human and murine antibody fragments, generally human constant and murine variable regions.

Humanized antibody: This refers to an antibody derived from a non-human antibody, typically murine, and a human antibody which retains or substantially retains the antigen-binding properties of the parent antibody but which is less immunogenic in humans.

Complementarity Determining Region, or CDR: This refers to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al., (1991) *Sequences of Proteins of Immunological Interest,* 5th Edition, Department of Health and Human Services, Public Health Service, National Institutes of Health, Bethesda (NIH Publication No. 91-3242).

Framework Region: This refers to amino acid sequences interposed between CDRs. These portions of the antibody serve to hold the CDRs in an appropriate orientation for antigen binding.

Specificity Determining Residue, or SDR: This refers to amino acid residues of an immunoglobulin that are directly involved in antigen contact.

Constant Region: This refers to the portion of the antibody molecule which confers effector functions. In the present invention, the variant antibodies include constant regions derived from human immunoglobulins. The heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. The light chain constant region can be of the kappa or lambda type, preferably the kappa type.

Mammals: This refers to animals that nourish their young with milk secreted by mammary glands, preferably warm blooded mammals.

Immunogenicity: A measure of the ability of a targeting protein or therapeutic moiety to elicit an immune response (humoral or cellular) when administered to a recipient. The present invention is concerned with the immunogenicity of humanized antibody CC49.

Reduced immunogenicity: This refers to an antibody, typically humanized, that exhibits reduced immunogenicity relative to the parent antibody.

Immunoreactivity: A measure of the ability of an immunoglobulin to recognize and bind to a specific antigen.

Substantially similar binding properties: This refers to a humanized antibody which retains the ability to specifically bind the antigen recognized by the parent antibody used to produce the humanized antibody. Preferably, the affinity of the humanized antibody is at least about 10% of the affinity of the parent antibody, more preferably at least about 25%, even more preferably at least about 50%. Most preferably, the humanized antibody exhibits antigen-binding affinity that is at least about 75% of the affinity of the parent antibody. Methods for assaying antigen-binding affinity are well known in the art and include half-maximal binding assays, competition assays, and Scatchard analysis.

Substantially Homologous: Refers to immunoglobulin sequences that exhibit at least about 85% identity, more preferably about 90% identity, most preferably about 95% identity with a reference immunoglobulin, wherein % identity is determined by comparing the number identical of amino acid residues between the two immunoglobulins, wherein the positions of the amino acid residues are indicated using the Kabat numbering scheme.

Nomenclature: Nucleic acids, amino acids, peptides, protective groups, active groups and so on, when abbreviated, are abbreviated according to the IUPAC IUB (Commission on Biological Nomenclature) or the practice in the fields concerned.

DETAILED DESCRIPTION

Figure 1:
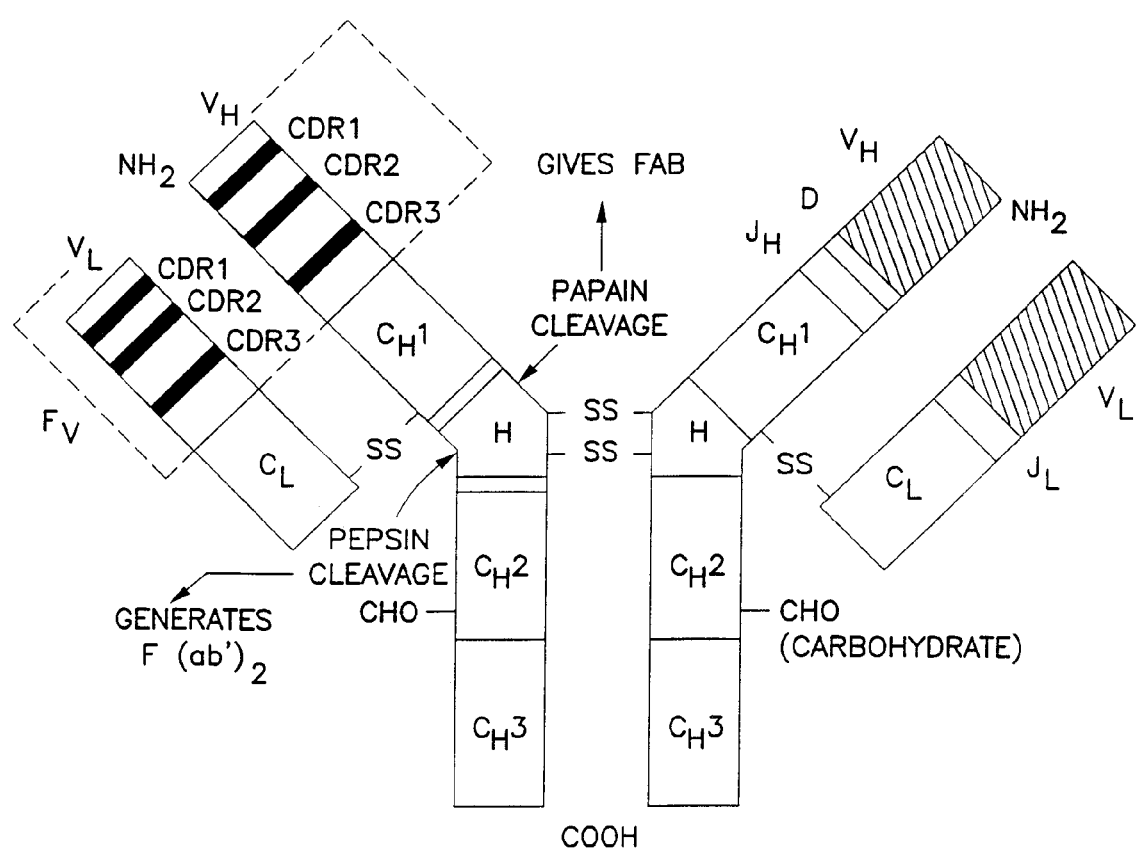
FIG. 1 illustrates a basic immunoglobulin structure.

To facilitate understanding of the invention, a discussion of the structure of a typical antibody molecule will first be provided. The basic immunological structural unit is shown in FIG. 1. Antibodies (also referred to as immunoglobulins) are constructed from four polypeptide chains, two heavy chains and two light chains. The two heavy chains are linked to each other by disulfide bonds and each heavy chain is linked to a light chain by a disulfide bond. There are two types of light chain, lambda ($\Sigma$) and kappa ($\kappa$). There are five main heavy chain classes (or isotypes) which determine the functional activity of an antibody molecule: IgM, IgD, IgG, IgA and IgE.

Each chain contains distinct sequence domains. The light chain includes two domains, a variable domain ($V_L$) and a constant domain ($C_L$). The heavy chain includes four domains, a variable domain ($V_H$) and three constant domains ($C_H1$, $C_H2$ and $C_H3$, collectively referred to as $C_H$) The variable regions of both light ($V_L$) and heavy ($V_H$) chains determine binding recognition and specificity to the antigen. The constant region domains of the light ($C_L$) and heavy ($C_H$) chains confer important biological properties such as antibody chain association, secretion, transplacental mobility, complement binding, and binding to Fc receptors. The Fv fragment is the N-terminal part of the Fab fragment of an immunoglobulin consisting of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site.

The variants of the invention are derived from a humanized CC49 (referred to as "parental HuCC49"). Parental HuCC49 is formed by grafting all six (three heavy chain and three light chain) MAb CC49 hypervariable regions onto the variable light ($V_L$) and variable heavy ($V_H$) frameworks of the human MAbs LEN and 21/28'CL, respectively, while retaining murine framework residues that may be required for the integrity of the antigen combining site structure (FIG. 11). (Kashmiri et al., (1995) Hybridoma, 14:461-473). The variants of the invention contain a reduced murine content, and consequently, reduced immunogenicity, when compared to HuCC49. Nonetheless, the variants of the invention retain a binding affinity that is substantially similar to that of HuCC49. Preferably the binding affinity is at least about $10^8$ $M^{-1}$. As used herein, HuCC49 refers to the humanized antibody formed by Kashmiri et al. The terms "variant HuCC49" or "variant" refer to the immunoglobulins of the invention.

A first aspect of the invention provides CDR variants of humanized monoclonal antibody (HuCC49) in which less than all six (three heavy chain and three light chain) Complementarity Determining Regions (CDRs) of CC49 are present. A second aspect of the invention provides SDR variants of humanized monoclonal antibody (HuCC49) in which only Specificity Determining Regions (SDRs) of at least one CDR from CC49 are present.

CDR Variants

According to the invention, CDR variants are formed by replacing at least one CDR of CC49 in HuCC49 with a corresponding CDR from a human antibody. Preferably, the L-CDR1 or L-CDR2, or both, from CC49 are replaced by a corresponding CDR from a human antibody. The inventors have found that a variant in which any of L-CDR3, H-CDR1, H-CDR2 or H-CDR3 of CC49 are replaced by a corresponding CDR from a human antibody do not retain significant binding affinity.

Binding Affinity of CDR Variants

According to the invention, CDR variants in which L-CDR1 or L-CDR2 of CC49, or both, are replaced by a corresponding CDR from a human antibody retain biological activity that is substantially similar to the binding affinity of the parental CC49. Generally, the CDR variants of the invention have a binding affinity that is about 25% to about 50% if the binding affinity of the parental CC49, more preferably about 50% to about 75%, most preferably, about 75% to about 100%.

CDR variants in which H-CDR2 is replaced by a corresponding CDR from a human antibody that is only slightly immunoreactive with TAG-72. In particular, such variants have a relative binding affinity that is about 300 fold less than that of CC49.

CDR variants in which L-CDR3, H-CDR1, or H-CDR3 are replaced by a corresponding CDR from a human antibody do not appear to retain any binding affinity for TAG-72.

Immunogenicity of CDR Variants

The CDR variants that have a reduced immunogenicity when compared to HuCC49 formed by grafting all six (three heavy chain and three light chain) CDR from CC49 onto the variable light ($V_L$) and variable heavy ($V_H$) frameworks of the human MAbs LEN and 21/28'CL, respectively. That is, the CDR variants of the invention are less likely to elicit an anti-idiotypic or HAMA response. Immunogenicity can be characterized using competition radioimmunoassays known in the art in which an "anti-CC49" antibody that recognizes the parental CC49 is exposed to both the parental MAb and the variant. Generally, a reduction in immunogenicity is reflected by a reduction in binding of the variant by the anti-CC49 antibody.

CDR variants in which L-CDR1 or L-CDR2, or both, of CC49 are replaced by a corresponding CDR from a human antibody show a slight reduction in immunogenicity, that is, the variants do not bind to the anti-CC49 antibody as well as HuCC49.

CDR variants in which L-CDR3 or H-CDR2 of CC49, is replaced by a corresponding CDR from a human antibody show a substantial reduction in immunogenicity. However, the inventors have found that such variants also show a substantial reduction in immunoreactivity.

CDR variants in which H-CDR1 or H-CDR3 or CC49 are replaced by a corresponding CDR from a human antibody do not show any measurable change in immunogenicity.

SDR Variants

The inventors have discovered that all six CDR of CC49 need not be present in their entirely for the humanized antibody to retain activity. Only residues that are directly involved in antigen contact, the Specificity Determining Residues (SDRs), are needed. SDR variants are formed by replacing at least one SDR of CC49 in HuCC49 with a residue at a corresponding position from a human antibody.

It should be noted that not all CDRs include SDRs. For example, it was determined that L-CDR1 and L-CDR2 of CC49 do not have any SDRs. Therefore, in one variant of the invention, L-CDR1 and L-CDR2 are replaced entirely with human CDRs. However, SDR variants can be formed by replacing residues within these CDRS with a corresponding human residue. L-CDR1 from CC49 and LEN differ at three positions, 27b, 27f and 29. Because residues 27b, 27f, 29 are not important for the binding affinity of CC49, a suitable SDR variant can include a corresponding human residue at any of these position, or at any combination of these positions. L-CDR2 from CC49 and LEN differ at position 53 only. Residue 53 is not considered important for the binding affinity of CC49. Thus, a suitable variant can include a corresponding human residue at position 53.

L-CDR3 of CC49 differs from LEN at three positions, 94, 96 and 97. The partially buried residue at position 97 is not important for the antigen binding activity of CC49. Thus, a suitable SDR variant can include a corresponding human residue at position 97. However, positions 94 and 96 of L-CDR3 are involved in ligand contact and should not be replaced to generate a functional SDR variant.

H-CDR1 of CC49 and 21/28'CL differ at three positions, 31, 32 and 34. However, SDR variants which include a corresponding human residue at positions 32 and 34 demonstrate no antigen binding affinity. Thus, a functional SDR variant should not include a corresponding human residue at either of these positions.

H-CDR2 of CC49 differs from human MAb 21/28'CL at eleven positions. The residues at positions 60, 61, 62 and 64 are not required for antigen binding activity. Therefore, a SDR variant of the invention can include a corresponding human residue at any of positions 60, 61, 62 and 64, or any combinations thereof.

Generally, H-CDR3 does not need to be considered when designing an SDR variant, because it does not show any reactivity to patients' sera.

In a preferred embodiment, the variant includes a combination of CDR and/or SDR substitutions to generate a variant having reduced immunogenicity and a binding affinity that is substantially similar to that of parental CC49. Suitable combinations include CDR variants in which both L-CDR1 and L-CDR2 of CC49 are replaced by a corresponding CDR from a human antibody. Other suitable variants include a combination of SDR and CDR substitutions. For example, a suitable variant can include corresponding human residues at position 97 of the light chain in addition to a substitution of L-CDR1 and/or L-CDR2 from CC49 with the corresponding CDRs from a human antibody. In another preferred embodiment, the variant includes a substitution at position 97 on the light chain in combination with substitutions at positions 60, 61, 62 and 64 on the heavy chain. In yet another embodiment, the variant includes a substitution at position 97 on the light chain in addition to a substitution of L-CDR1 and/or L-CDR2 from CC49 with the corresponding CDRs from a human antibody in combination with substitutions at positions 60, 61, 62 and 64 on the heavy chain.

In addition to variants specifically described herein, other "substantially homologous" modified immunoglobulins can be readily designed and manufactured using various recombinant DNA techniques well known to those skilled in the art. For example, the framework regions can be varied at the primary structure level. Moreover, a variety of different human framework regions may be used singly or in combination as a basis for the variant. In general, modifications of the genes may be readily accomplished by a variety of well-known techniques, such as site-directed mutagenesis.

Alternatively, polypeptide fragments comprising only a portion of the primary antibody structure may be produced wherein the fragment substantially retains the immunoreactive properties of the variant. These polypeptide fragments include fragments produced by proteolytic cleavage of intact antibodies by methods well known in the art, or fragments produced by inserting stop codons at the desired locations nucleotide sequence using site-directed mutagenesis. For example, a stop codon can be inserted after $C_H1$ to produce Fab fragments or after the hinge region to produce $F(ab')_2$ fragments. Single chain antibodies and fusion proteins which includes at least an immunoreactive fragment of the variant are also included within the scope of the invention. For example, the variants may be directly or indirectly attached to effector moieties having therapeutic activity. Suitable effector moieties include cytokines, cytotoxins, radionuclides, drugs, immunomodulators, therapeutic enzymes, anti-proliferative agents, etc. Methods for attaching antibodies to such effectors are well known in the art.

Binding Affinity of SDR Variants

L-CDR1 from CC49 and LEN differ at three positions, 27b, 27f and 29. Since L-CDR1 of CC49 can be replaced with the corresponding CDR from LEN without any significant loss of antigen binding reactivity, residues 27b, 27f, 29 are not considered important for the binding affinity of CC49. Thus, a variant of the invention can include a corresponding human residue at any of these three positions, or any combination thereof, and retain a binding affinity that is substantially similar to that of the parent HuCC49.

In L-CDR2, CC49 and LEN differ at position 53 only. Since L-CDR2 of CC49 can be replaced with the corresponding CDR from LEN without any significant loss of antigen binding reactivity, residue 53 is not considered important for the binding affinity of CC49. Thus, the humanized antibody of the invention can include a corresponding human residue at residue 53 and retain a binding affinity that is substantially similar to that of the parent HuCC49.

L-CDR3 of CC49 differs from LEN at three positions, 94, 96 and 97. The partially buried residue at position 97 is not important for the antigen binding activity of CC49. Thus, the humanized antibody of the invention can include a corresponding human residue at position 97 and retain a relative binding affinity that is substantially similar to that of CC49. However, positions 94 and 96 of L-CDR3 appear to be involved in ligand contact. Therefore, an SDR variant which includes a corresponding human residue at either position 94 or 96, or both will generally suffer total or near total loss of antigen binding reactivity.

H-CDR1 of CC49 and 21/28'CL differ at three positions, 31, 32 and 34. SDR variants which include a corresponding human residue at positions 32 and 34 demonstrate no antigen binding affinity.

H-CDR2 of CC49 differs from human MAb 21/28'CL at eleven positions. The residues at positions 60, 61, 62 and 64 do not appear to be required for antigen binding activity. Therefore the humanized antibody of the invention can include a corresponding human residue at any of positions 60, 61, 62 and 64, or any combinations thereof, and the variant will retain a binding affinity that is substantially similar to that of CC49.

Immunogenicity of SDR Variants

SDR variants are particularly beneficial because some CDRs that are important for immunoreactivity are also immunogenic (e.g., L-CDR3 and H-CDR2). Thus, the immunogenicity of various SDR replacements within L-CDR3 and H-CDR2 were examined.

As shown in FIG. 2, L-CDR3 consists of residues 89-97 and H-CDR2 consists of residues 50-65. The inventors have found that SDR variants which include a corresponding human residue in positions 32 and 34 (found within H-CDR1) or at position 97 (found within L-CDR3) are still immunogenic. Whereas, SDR variants which include a corresponding human residue in positions 60, 61, 62, and 64 (found within H-CDR2) or at position 94 (found within L-CDR3) show a reduction in immunogenicity. SDR variants which include a corresponding human residue in position 96 (found within L-CDR3) do not appear to be immunogenic.

Generally, the residues found in H-CDR3 does not need to be considered when designing SDR variants, because it does not show any reactivity to patients' sera.

Human Antibodies

Suitable human antibodies include, but are not limited to: ROY, AU, REI, HAU, HK101'CL, SCW, WEA, HK137'CL, HK134'CL, DAUDI'CL, WALKER'CL, GAL(1), LAY, WES, Vb'CL, HK102'CL, EU, DEN, AMYLOID BAN, MEV, Vd'CL, Va'CL, KUE, Ve'CL, V13'CL, V18A'CL, V19A'CL, V19B'CL, V18C'CL, NIM, CUM, GM603CL, FR, RP M1-6410'CL, TI, WOL, SIE, NG9'CL, NEU, GOT, PAY, SON. GAR', PIE, FLO, GLO, CUR, IARC/BL41'CL, POM, REE, K-EV15'CL, VJI'CL, VKAPPAIV, GERMLINE'CL, PB171'CL, LEN, NEWM, HA, NIG-64, NEW, BL2'CL, WAH, NIG-77, VOR, RHE, LOC, OKA, COX, NIG-51, NIG-84, MES, WH, NEI, WEIR, TOG, TRO, BOH, NIG-58, VIL, WIN, 41'CL, HIL, LAP, GAR, MOT, BO, MDG, AMYLOID-AR, SUT, THO,LBV'CL, NIG-48, HG3'CL, ND'CL, COR, DAW, OU, MCE', CE-1'CL, HE, SUP-T1, VH-JA'CL, HIG1'CL, TUR, LAMDA-VH26'CL, WAS, H11'CL, TEI, BRO'IGM, GRA', ZAP, JON, DOB, NIE, 333'CL, IHI'CL, IBIi'CL, 126'CL, 112'CL, 115'CL, KOL and 21/28'CL. New human antibodies are being discovered and sequenced, many of those, as of yet unknown antibodies may also be suitable. Preferably, human antibody has a sequence that is identical or substantially similar (containing as few mutations as possible) to the human germ line sequences. For example, the light chain CDR of CC49 in HuCC49 can be replaced with the corresponding CDR from LEN (Kabat et al., 1991) and the heavy chain CDR can be replaced with the corresponding CDR from 21/28'CL (Kabat et al., 1991).

Methods of Producing

The variants of the invention can be produced by expressing the appropriate DNA sequence in a host after the sequence has been operably linked to (i.e., positioned to ensure the functioning of) an expression control sequence. Such expression vectors are typically replicable in a host organism either as episomes or as an integral part of the host chromosomal DNA. The expression vectors typically contain expression control sequences compatible with the host cell, such as an origin of replication. In addition, the expression vector will typically include a promoter. Suitable promoters include the polyhedrin promoter, lactose promoter system, a tryptophan promoter system, a beta-lactamase promoter system, or a promoter system from phage lambda. Promoters typically control expression of the gene, optionally, with operator sequences, and have ribosome binding site sequences and the like for initiating and completing transcription and translation. Commonly, expression vectors will contain selection markers. DNA sequences encoding the light chain and heavy chain of the antibody may be inserted into separate expression vectors, or into the same expression vector.

Suitable hosts include prokaryotic strains such as *E. coli; Bacilli*, including *Bacillus subtilus*; enterobacteriacae, including *Salmonella, Serratia* and *Psuedomonas*. Suitable hosts also include eukaryotic hosts such as yeast, including *Saccharomyces; Pichia pastoris*; Sf9 insect cells; Sp2/0, VERO and HeLa cells, Chinese hamster ovary (CHO) cell lines; W138, BHK, COS-7 and MDCK cell lines.

The vectors containing the DNA segments of interest can be transferred into the host cell by well-known methods, which vary depending on the type of cellular host. For example, calcium chloride transfection, calcium phosphate treatment, electroporation or cationic liposome mediated transfection (such as DOTAP). Successfully transformed cells, can be identified by a variety of techniques well known in the art for detecting the binding of a receptor to a ligand.

Once expressed, the gene products can be purified according to standard procedures of the art, including ammonium sulfate precipitation, affinity columns, column chromatography, and gel electrophoresis. Substantially pure immunoglobulins of at least about 90% to about 95% homogeneity are preferred, and 98% to 99% or more homogeneity most preferred for pharmaceutical uses.

Methods of Use

Once purified, the variants of the invention may be used therapeutically, or in developing and performing assays, in vivo or in vitro diagnostic procedures, and imaging. The variants of the invention are particularly useful for the treatment of diseases such as cancer, in particular for treating or detecting cancer. The variants can be administered to a patient alone or in combination with a pharmaceutical formulation. Typically, the variants are incorporated into a pharmaceutically acceptable, non-toxic, sterile carrier as a suspension or solution. The antibodies of the invention can be used as separately administered compositions or given in conjunction with chemotherapeutic or immunosuppressive agents.

The variants provide unique benefits when used for the treatment of cancer. In addition to the ability to bind specifically to malignant cells and localize tumors without binding to non-cancerous cells, the variants have a reduced immunogenicity when compared to HuCC49.

For diagnostic purposes, the antibodies may either be labeled or unlabeled. Unlabeled antibodies can be used in combination with other labeled antibodies (second antibodies) that are reactive with the humanized antibody, such as antibodies specific for human immunoglobulin constant regions. Alternatively, the antibodies can be directly labeled. A wide variety of labels can be employed, such as radionuclides, fluors, enzymes, enzyme substrates, enzyme cofactors, enzyme inhibitors, ligands (particularly haptens), etc. Numerous types of immunoassays are available and are well known to those of skill in the art.

Kits according to the present invention include frozen or lyophilized variant to be reconstituted by thawing or by suspension in a liquid vehicle. The kits may also include a carrier or buffer. Preferably, the kit also comprises instructions for reconstituting and using the variant antibody.

WORKING EXAMPLES

To identify the CDRs essential for binding, a panel of variant HuCC49 MAbs were generated using the baculovirus expression system. HuCC49 was prepared by grafting MAb CC49 CDRs onto the $V_L$ and $V_H$ frameworks of the human MAbs LEN and 21/28' CL, respectively, as described by Kashmiri et al., (1995) *Hybridoma*, 14:461-473. Six CDR variants were constructed by replacing a single CC49 CDR of either the light or heavy chain with the corresponding human antibody CDR (LEN and 21/28'CL, respectively). Variants were denoted as L-1, L-2, L-3, H-1, H-2 or H-3. A seventh variant, L-1,2 was made by replacing two CC49 light chain CDRs (L-CDR1 and L-CDR2) with the corresponding CDRs of the human antibody LEN.

Since the seven CDR variants were derived by simply replacing the murine CDRs with the human antibody hypervariable regions, all of the variants carry identical $V_H$ and $V_L$ frameworks and K1 and k chain constant regions SDR heavy chain and light variants were constructed by substituting mutagenic nucleotides in or near the CDRs.

Example I

Preparation of CDR Substituted MAb CC49

According to the invention, CDR variants are formed by replacing at least one CDR of CC49 in HuCC49 with a corresponding CDR from a human antibody. The CDR variants of the invention include:

Variant L-1: L-CDR1 of CC49 (SEQ ID NO: 1) was replaced with L-CDR1 of LEN (SEQ ID NO: 7).

Variant L-2: L-CDR2 of CC49 (SEQ ID NO: 2) was replaced with L-CDR2 of LEN (SEQ ID NO: 8).

Variant L-3: L-CDR3 of CC49 (SEQ ID NO: 3) was replaced with L-CDR3 of LEN (SEQ ID NO: 9).

Variant L-1,2: L-CDR1 and L-CDR2 of CC49 (SEQ ID NOs: 1 and 2, respectively) were replaced with L-CDR1 and L-CDR2 of LEN (SEQ ID NOs: 7 and 8, respectively).

Variant H-1: H-CDR1 of CC49 (SEQ ID NO: 4) was replaced with H-CDR1 of 21/28'CL (SEQ ID NO: 10).

Variant H-2: H-CDR2 of CC49 (SEQ ID NO: 5) was replaced with H-CDR2 of 21/28'CL (SEQ ID NO: 11).

Variant H-3: H-CDR3 of CC49 (SEQ ID NO: 6) was replaced with H-CDR3 of 21/28'CL (SEQ ID NO: 12).

Production of Oligomers to Generate $V_H$ Variants

Synthesis of three variant $V_H$ genes was performed using the overlap extension PCR technique described by Kashmiri et al., (1995) *Hybridoma* 14:461-473. Four 123-126 base pair long overlapping oligonucleotides (SEQ ID NOs: 15-18), (which together encompass the entire sequence of the variant $V_H$ gene on alternating strands) were used to generate variant $V_H$ genes. (FIG. 12B) The oligomers were supplied by Midland Certified Reagent Co., Midland, Tex. Instead of a template DNA, the PCR mixture contained 2 pmoles of the four oligonucleotides. PCR was carried out by three cycles of a denaturing step at 94° C. for 1 minute, a primer annealing step at 55° C. for 2 minutes, and an extension step at 70° C. for 2 minutes, followed by 17 additional cycles of denaturation (94° C., 1 minute), primer annealing (55° C., 2 minutes), and extension (72° C., 1 minute). All polymerase chain reactions (PCRs) were carried out in a final volume of 100 Tl of PCR buffer containing 100 TM of dNTPs, 5 units of Taq DNA polymerase (Boehringer Mannheim) and 20 pmol of each end primer.

Production of Oligomers to Generate $V_L$ Variants

The three variant $V_L$ genes were generated using 30-43 base oligonucleotides as a mutagenic primer. The oligonucleotides contained the desired base changes in the targeted CDR. The mutagenic primers for the $V_L$ genes were synthesized using a Model 8700 DNA synthesizer (Miligen/Bioresearch, Burlington, Vt.). (FIG. 12A) Primer induced mutagenesis was carried out by a two-step PCR method, as described by Landt et al., (1990) Gene, 96:125-128. pLNXCHuCC49HuK (Kashmiri et al, (1995) Hybridoma 14:461-473) (FIG. 2) was used as a template in both steps. In the first step, the mutagenic primer was used as a 3' primer while a 20 nucleotide long end primer served as a 5' primer. The product of the first PCR was gel purified and utilized as a 5' primer for the second PCR in which a 20 nucleotide long end primer was used as a 3' primer. The 20 nucleotide long end primers used for DNA amplification were supplied by Midland Certified Reagent Co. (Midland, Tex.). The sequences for these primers are reported by Kashmiri et al., (1995) Hybridoma 14:461-473 and are as follows:

```
                                           (SEQ ID NO: 23)
1.   5' V_H,  5'-CTA AGC TTC CAC CAT GGA G-3'

(SEQ ID NO: 24)
2.   3' V_H,  5'-ATG GGC CCG TAG TTT GGC G-3'

(SEQ ID NO: 25)
3.   5' V_L,  5'-GCA AGC TTC CAC CAT GGA TA-3'

(SEQ ID NO: 26)
4.   3' V_L,  5'-AGC CGC GGC CCG TTT CAG TT-3'
```

Each of the primers carries a single restriction endonuclease site at its flank. The 5' primers carry a HindIII site, while the 3'$V_H$ primer carries an ApaI, and the 3'$V_L$ primer has a SacII site. The restriction endonuclease recognition sequences are underlined.

The first PCR was carried out in a final volume of 100 Tl containing 10 ng of the template DNA, 20 pmol each of the 3' and 5' primers, 100 TM dNTPs and 5 units of Taq DNA polymerase (Boehringer Mannheim, Indianapolis, Ind.). Each step of the PCR consisted of 25 cycles of denaturation (94° C., 1 minute), primer annealing (45° C., 2 minutes), and extension (72° C., 2 minutes). The PCR product was extracted with phenol/chloroform, precipitated with ethanol and gel purified prior to insertion into a vector.

Example II

Assembly of CDR Substituted MAb CC49 PCR Products

The PCR products encoding the $V_H$ were treated with HindIII/ApaI. The PCR products were subcloned for sequencing in pBluescript S/K+ (Stratagene, La Jolla, Calif.) at a HindIII/ApaI site after the plasmid was linearized using the appropriate restriction endonucleases. Inserts were sequenced to check their fidelity to their templates.

Figure 3:
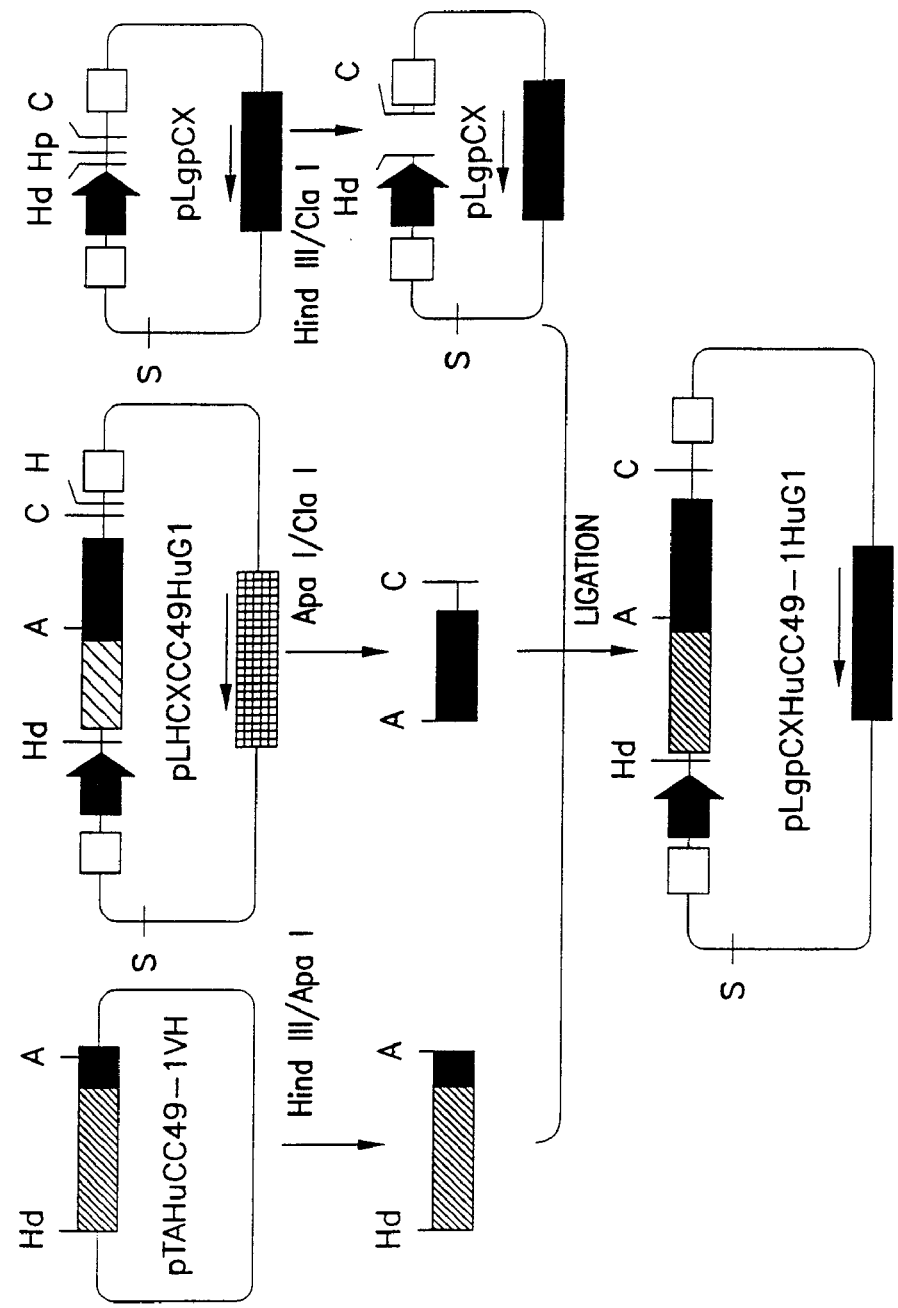
FIG. 3 is a schematic representation of the eukaryotic expression constructs of the humanized heavy (B) chains of HuCC49. Thin lines represent sequences derived from the prokaryotic vectors pBR322, pBluescript SK⁻, or pCR II. Thick lines depict human K constant region. Boxes with vertical, horizontal, or cross bars show neomycin, mycophenolic acid, or hygromycin resistance genes; thin arrows show their transcriptional direction. Empty boxes are retroviral long terminal repeats, while thick arrows show the HCMV promoter and its transcriptional direction. Only relevant enzyme sites are shown. A: ApaI; B: BamHI; C: ClaI; Hd: HindIII; Hp: HpaI; N: NheI; R: EcoRI; and S: SacII.
Figure 4:
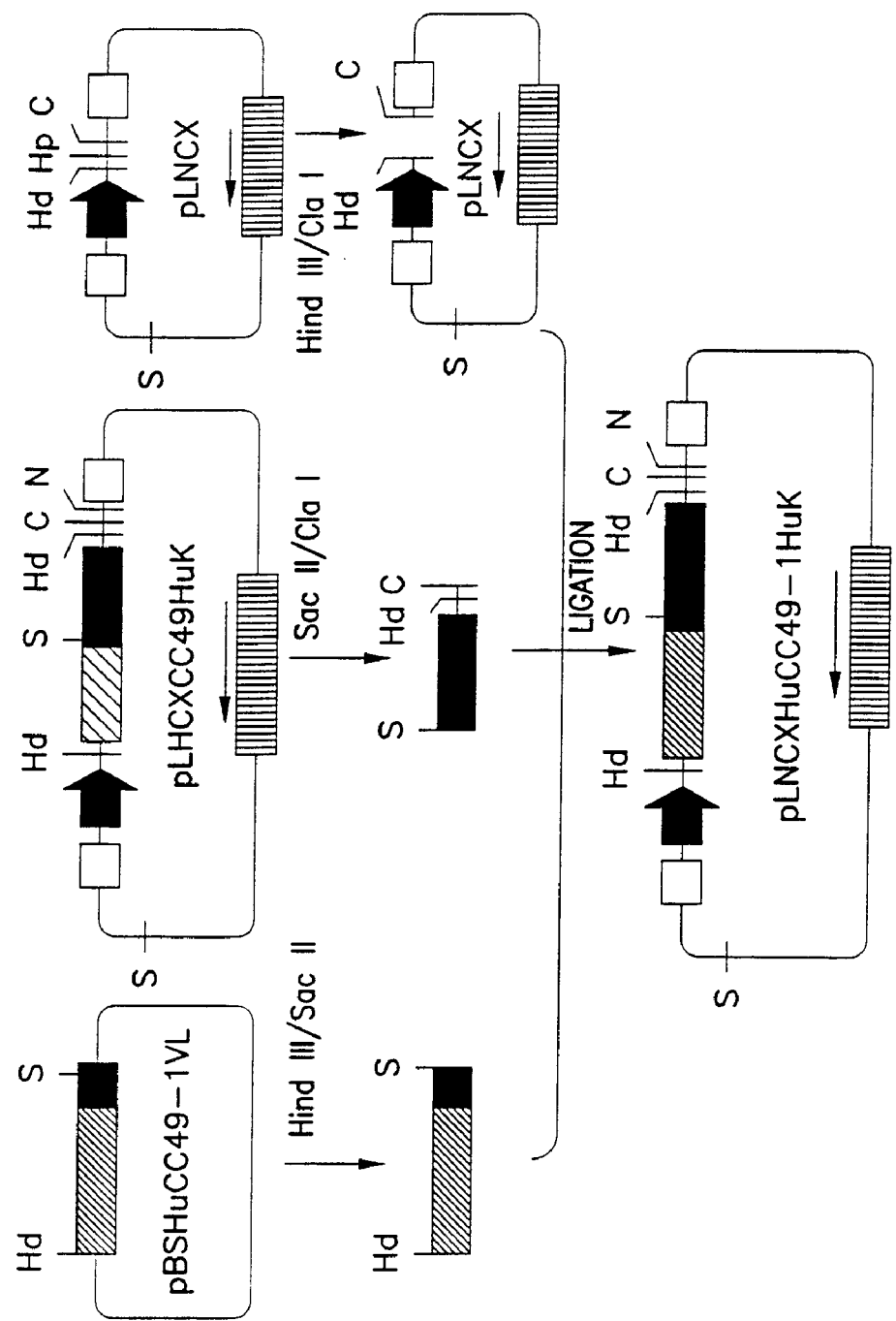
FIG. 4 is a schematic representation of the eukaryotic expression constructs of the humanized light chains of HuCC49. As with FIG. 3, thin lines represent sequences derived from the prokaryotic vectors pBR322, pBluescript SK⁺, or pCR II. Thick lines depict human k constant region. Boxes with vertical, horizontal, or cross bars show neomycin, mycophenolic acid, or hygromycin resistance genes; thin arrows show their transcriptional direction. Empty boxes are retroviral long terminal repeats, while thick arrows show the HCMV promoter and its transcriptional direction. Only relevant enzyme sites are shown. A: ApaI; B: BamHI; C: ClaI; Hd: HindIII; Hp: HpaI; N: NheI; R: EcoRI; and S: SacII.
Figure 5:
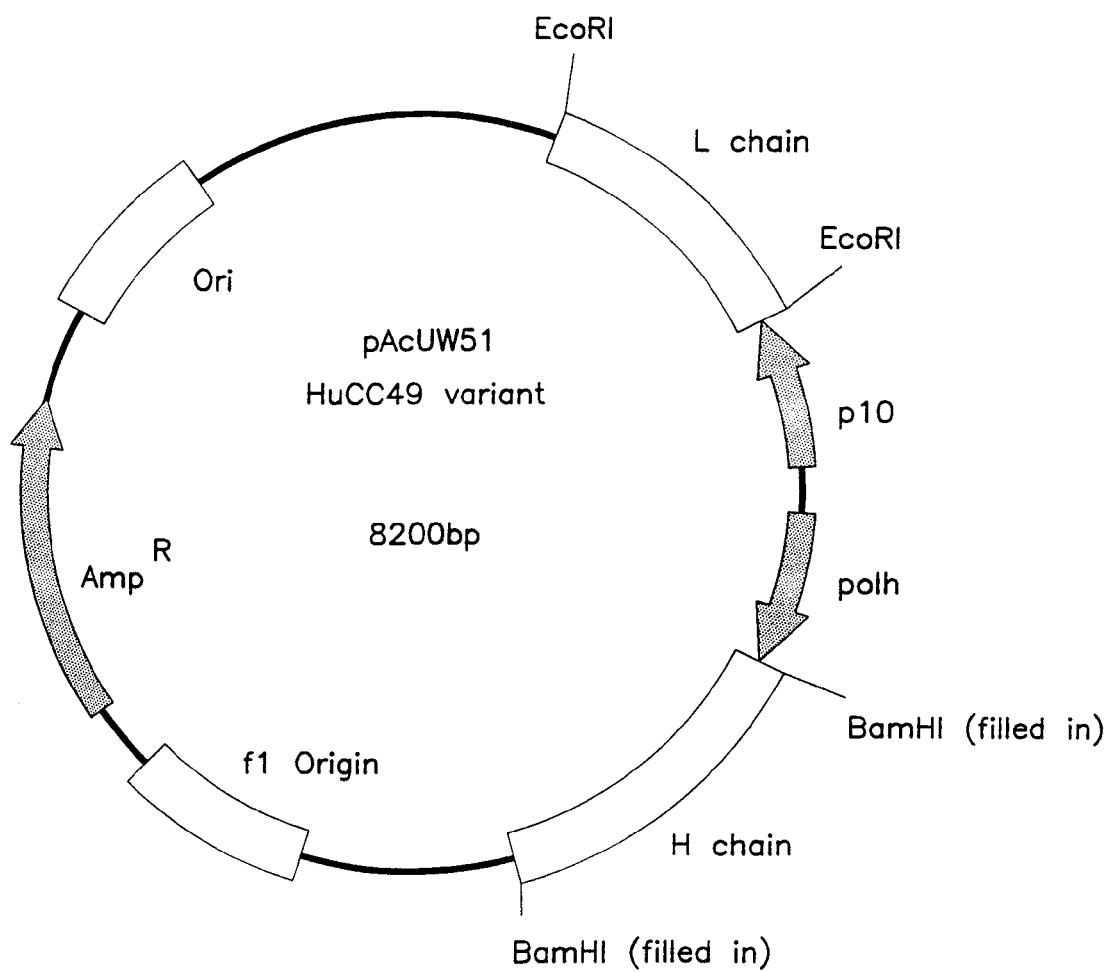
FIG. 5 is a schematic representation of the dual expression constructs of the variant heavy (H) and light (L) chain genes derived from the baculovirus vector pAcUW51. P10 and polh represent p10 and polyhedrin promoter; arrows show their direction of transcription. Ori and f1 are SV40 and f1 origin of replication. $Amp^R$ represents an ampicillin resistant gene.

To assemble the variable and constant regions of the heavy chain the HindIII/ApaI insert was released form pBluescript. A DNA fragment encoding the human K1 constant region was excised from pLgpCXHuCC49HuG1 (Kashmiri et al, (1995) Hybridoma 14:461-473), (FIG. 3) by ApaI/ClaI cleavage. The HindIII/ApaI and the ApaI/ClaI fragments were joined. The recombinant was unidirectionally inserted, by three way ligation, between the HindIII and ClaI sites of pBluescript. The DNA sequence encoding the entire heavy chain was then cleaved from pBluescript by HindIII/ClaI digestion. Its termini were filled in using the Klenow fragment of the DNA polymerase. The insert was subcloned in a light chain construct of pAcUW51 (FIG. 4), at the blunt ended BamHI site located downstream of the polyhedrin promoter.

The PCR products encoding the $V_L$ were treated with HindIII/SacII. The PCR products were subcloned for sequencing in pBluescript S/K+ (Stratagene, La Jolla, Calif.) at a HindIII/SacII site after the plasmid was linearized using the appropriate restriction endonucleases. Inserts were sequenced to check their fidelity to their templates.

To assemble the variable and constant region of the light chain, the HindIII/SacII insert was released from the pBluescript construct. A DNA fragment encoding the human kappa constant region was excised from pLNCXHuCC49HuK (Kashmiri et al, (1995) Hybridoma 14:461-473), (FIG. 2) by SacII/ClaI treatment. The HindIII/SacI fragments were joined to the HindIII/ClaI linearized pBluescript by three way ligation. The entire light chain was cleaved from pBluescript using EcoRI. The EcoRI fragment was inserted into the baculovirus expression vector pAcUW51 (Pharmingen, San Diego, Calif.) at the EcoRI site located downstream from the p10 promoter.

The baculovirus expression construct of the parental HuCC49 was generated using DNA fragments encoding HuCC49 heavy and light chains obtained from PLNCXHuCC49HuK and pLgpCXHuCC49HuG1. PLNCXHuCC49HuK was cleaved with HindIII. The resulting >1.0 Kb DNA fragment encoding HuCC49Huk was subcloned in pBluescript at the HindIII site. The resulting construct was then cleaved with BamHI and the fragment was cloned in the baculovirus vector pAcUW51 at the BamHI site, downstream from the polyhedrin promoter. A >1.4 Kb DNA fragment encoding HuCC49HuG1 was cloned from pLgpCXHuCC49HuG1 using HindIII/ClaI. The DNA fragment was filled using the Klenow fragment of DNA polymerase. pAcUW51 was linearized with BglII and its ends blunted using the Klenow fragment. The DNA fragment was then inserted in the pAcUW51 expression construct of HuCC49HuK, downstream from the p10 promoter.

Example III

Generation of Baculovirus Recombinant CDR Substituted CC49 MAb

Serum free adapted Sf9 insect cells (Gibco BRL, Gaithersburg, Md.) were cultured at 28° C. in Sf900-II medium (Gibco BRL) without supplements as described by Salgaller et al, (1993) Cancer Res., 53:2154-2161. To develop the recombinant baculovirus, 1×10⁶ Sf9 cells in a 35 mm dish were co-transfected with 0.5 ml pAcUW51 derived baculovirus expression construct of the CDR substituted light chain gene and the HuCC49 heavy chain gene along with linearized BACULOGOLD wild type baculovirus DNA (Pharmingen), using a cationic liposome mediated transfection system, DOTAP (Boehringer Mannheim) according to the suggested protocol. Similarly, variant antibodies containing CDR substituted heavy chain were produced by co-transfecting Sf9 cells with BACULOGOLD baculovirus DNA and baculovirus dual expression constructs carrying CDR substituted heavy chain and HuCC49 light chain genes. Baculovirus recombinant HuCC49 (hereafter referred to as HuCC49) was used as a control antibody. HuCC49 was produced by transfecting insect cells with pAcUW51 carrying HuCC49 light and heavy chains.

Five days after transfection, the infectious supernatants were harvested from the transfectants. 1 ml of this supernatant was serially diluted and used to infect a monolayer of $5 \times 10^6$ Sf9 cells in a 100 mm dish. The cells were then overlaid with 0.5% Baculovirus Agarose (Invitrogen, Carlsbad, Calif.) as described by Bei et al., (1995) *J. Immunol. Methods,* 186: 245-255. Viral plaques were expanded by three rounds of infection. For each round of expansion, a larger population of freshly seeded monolayers of Sf9 cells were infected, using the highest producing clone as a source of inoculum. The putative recombinant viral plaques were purified and isolated in 1 ml of Sf900 media. If necessary, viruses were further amplified by infecting cells at an Multiplicity of Infection (MOI) of 0.1. To produce the recombinant antibodies, $6.0 \times 10^8$ Sf9 cells were infected with the infectious supernatant at an MOI of 5.

Purification of CDR Substituted MAbs

The culture supernatant was clarified by pelleting cell debris at 10,000×g, and was applied to an ion-exchange column (DE52; Whatman, Hillsboro, Oreg.) at pH 7.2 to remove extraneous proteins. The unbound protein fraction was subjected to protein G (Gibco BRL) affinity chromatography. The material bound to protein G was eluted from the column using 0.1 M glycine hydrochloride buffer, pH 2.6 and the pH of the eluted material was immediately adjusted to 7.4 using 1.0 M Tris buffer, pH 8.0. The buffer was replaced by phosphate buffered saline and the eluted material was concentrated using a Centricon 30 micro concentrator (Amicon, Beverly, Mass.). Protein concentration was determined by the method of Lowry et al., (1951) *J. Biol. Chem.* 193:265-275. The purity of the antibody preparation was analyzed using a precast continuous 4-15% SDS-polyacrylamide Tris-glycine gel (Novex Systems, San Diego, Calif.) and visualized by Coomassie blue staining as described by Kashmiri et al., (1995) *Hybridoma* 14:461-473.

Radiolabeling of MAbs

The murine MAb CC49 and HuCC49 were labeled with Na $^{125}$I using the iodogen (Pierce, Rockford, Ill.) method as described by Fraker (1978) *Biochem. Biophys. Res. Commun.,* 80:849-857 and Colcher (1988) *Cancer Res.,* 48:4597-4603. The protocol routinely resulted in specific activities at 5-10 TCi/Tg. The immunoreactivities of the radiolabeled MAbs were assessed by the radioimmunoassay described by Schott et al., (1992) *Cancer Res.,* 52:6413-6417 using bovine submaxillary mucin (BSM) immobilized on a solid support (Reacti-gel HW 65F; Pierce)

Immunoglobulin Production

The titer of the transfectants and the putative viral plaques were assayed for immunoglobulin production by enzyme-linked immunosorbent assay (ELISA) based on reactivity of the test aliquot with goat anti-human Fc (K1) and goat anti-human kappa antibodies as described by Bei et al., (1995) *J. Immunol. Methods,* 186:245-255. Transfectants and viral plaques derived from each of the expression constructs were positive for immunoglobulin production.

However, when the transfectants and the viral plaques were assayed for immunoreactivity with TAG-72 positive bovine submaxillary mucin (BSM), the clones derived from the expression constructs carrying L-1, L-2 and L-1,2 were positive, while those generated by the H-2 expression construct were barely immunoreactive. Those derived from the constructs carrying either L-3, H-I and H-3 demonstrated no immunoreactivity with BSM at all.

Figure 6:
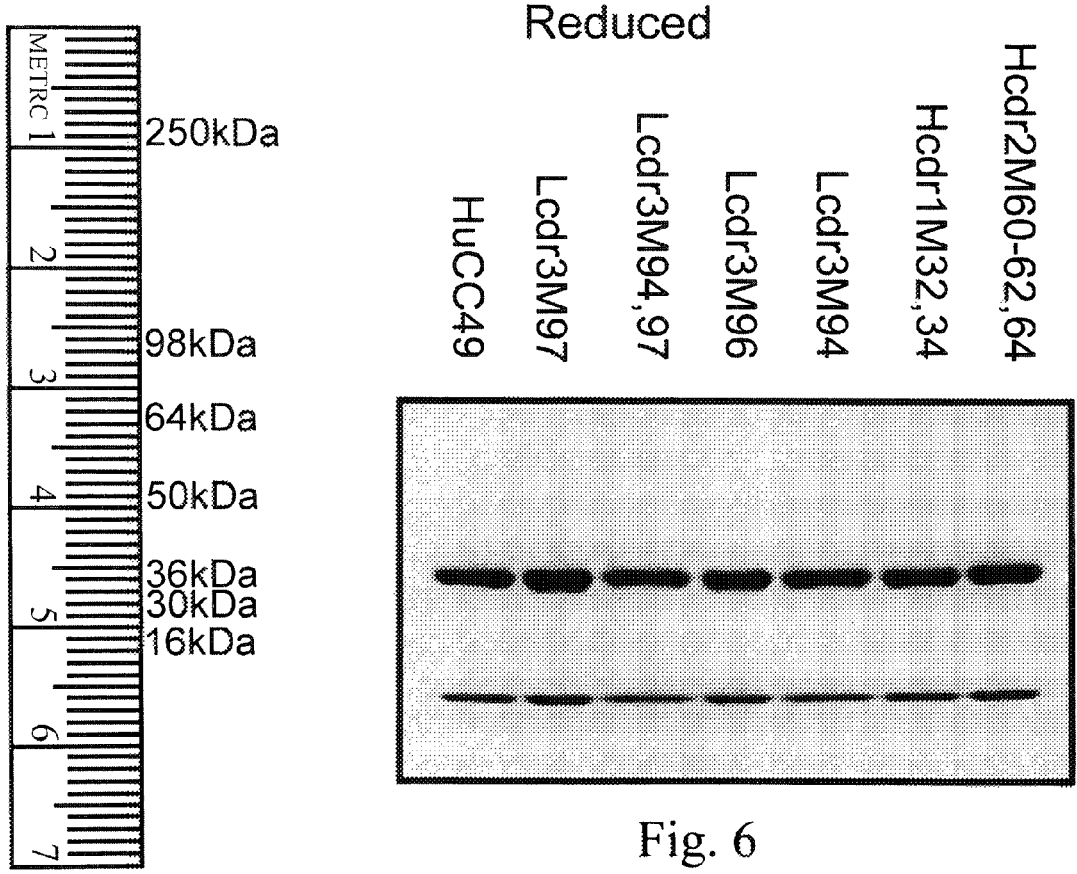
FIG. 6 shows an SDS-PAGE analysis of purified MAb HuCC49 and its variants. All samples are shown in a reduced condition. Lane 1: molecular weight marker (Gibco Brl); Lanes 2-8: variants L-1, L-2, L-3, L-1,2, H-1, H-2 and H-3; Lane 9: HuCC49.

It was then assessed whether the poor or lack of BSM reactivity of the clones derived from L-3, H-1, H-2 and H-3 expression constructs was due to low levels of immunoglobulin secretion by these clones. To that end, Sf9 cells were infected with the infectious supernatants at an MOI of 5 and cultured under the conditions described above. The secreted antibody was purified from equal volumes of the culture supernatant from each of the infected cultures, and analyzed by SDS-PAGE. The gel profile under non-reducing conditions showed that the mobility of the variant antibodies was identical to that of the HuCC49, which has a molecular weight of approximately 160 kDa (data not shown). Under reducing conditions, the variant antibodies, like the HuCC49 MAb, yielded two protein bands of approximately 25-28 kDa and 50-55 kDa (FIG. 6). These mobilities are in conformity with the molecular masses of the immunoglobulin heavy and light chains. More importantly, it is evident that regardless of their BSM reactivity, clones derived from each of the constructs encoding CDR-substituted heavy or light chain produce as much immunoglobulin as the clone derived from the constructs encoding the parental humanized heavy and light chains.

Example IV

Competition Radioimmunoassays for CDR Substituted Variants

Binding Affinity of Variant Antibodies

The relative binding affinity of the HuCC49 and the CDR substituted variant antibodies to TAG-72 was determined using the competition radioimmunoassay (RIA) described by Milenic et al., (1991) *Cancer Res.,* 51:6363-6371. Serial dilutions of the purified variant MAbs, as well as the parental HuCC49, were prepared in phosphate buffered saline (PBS) containing 1% bovine serum albumin (BSA). 25 Tl was added to the wells of microtiter plates containing 10 ng BSM. $^{125}$I-labeled HuCC49 (50,000 cpm in 25 Tl) was then added to each well. The plates were incubated overnight at 4° C. and then washed and counted in a K-scintillation counter.

Figure 7:
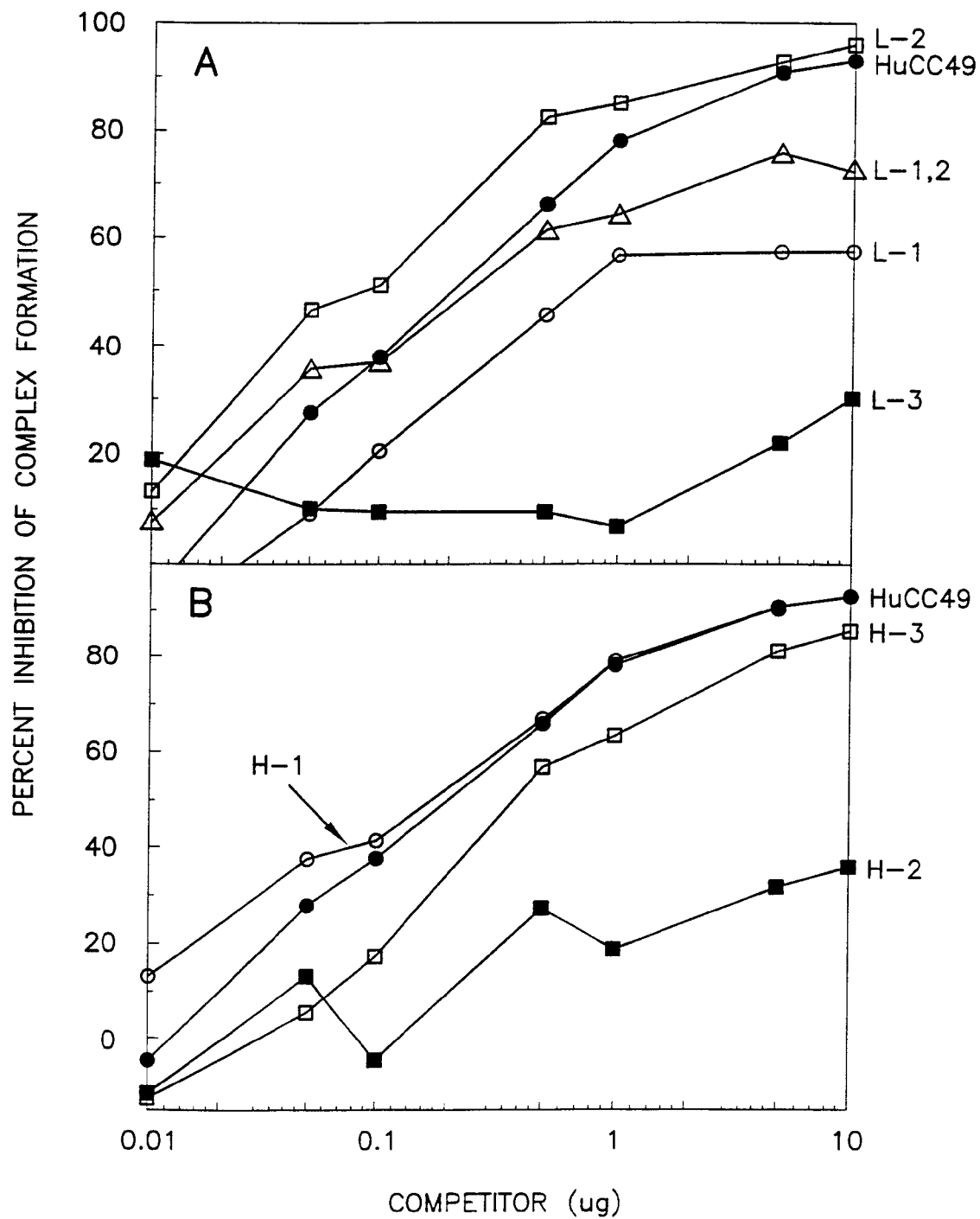
FIG. 7 shows an analysis of parental and variant forms of HuCC49 in a competitive RIA. The antigen binding of the light chain (A) and heavy chain (B) CDR variants was assessed using $^{125}$I-labeled HuCC49. In panel A, the competitors were: HuCC49, L-1, L-2, L-3, L-1,2. In panel B, the competitors were: H-1, H-2 and H-3.

Unlabeled HuCC49 or its variants were used to compete for the binding of $^{125}$I-HuCC49 to TAG-72 positive BSM. The variants, L-1, L-2 and L-1,2, were found to completely inhibit the binding of the $^{125}$I-labeled HuCC49 to TAG-72, while L-3 did not compete at all (FIG. 7).

The relative affinity constants were calculated by the modification of the Scatchard method described by Frankel et al., (1979) Mol. Immunol., 16: 101-106. An approximation of the specific activity of the $^{125}$I-HuCC49 was made and used to determine the final concentration for each of the dilutions of the variant MAbs. The calculations were performed as described by Milenic et al., (1991) *Cancer Res.,* 51:6363-6371.

The relative affinity constants (Ka) of the variants were as follows:

L-1 had a Ka of $3.3 \times 10^{-8}$ M (only about 2-fold less than that of HuCC49).

L-2 had a Ka of $6.81 \times 10^{-8}$ M (comparable to that of HuCC49).

L-1,2 had a Ka of $2.9 \times 10^{-8}$ M (only about 2-fold less than that of HuCC49).

H-1 and H-3 displayed no competition

H-2 competed only slightly with the HuCC49. The Ka of H-2 was $0.018 \times 10^{-8}$ M (approximately 300-fold less than the Ka of HuCC49).

Reactivity of the CC49 Anti-idiotypic Antibodies to the Variant Antibodies

The variant MAbs were also characterized in the competition radioimmunoassay RIA described by Irvine et al., (1993) *Cancer Immunol. Immunother.*, 36:281-292 using mouse anti-idiotypic MAb generated against MAb CC49. Three anti-idiotypic (AI49-8, AI49-3 and AI49-1) were selected, representing each of the anti-idiotypic subsets, I, Θ, and K, respectively. In the same manner described above, 100 ng of MAb AI49-3 (Θ-subset), AI49-1 (K-subset) or AI49-8 (I-subset) were adsorbed to each well of a 96-well microtiter plate. 25 Tl of the serially diluted variant MAbs or HuCC49 was added to each well along with 25 Tl of $^{125}$I-murine CC49. The plates were washed and counted after an overnight incubation at 4° C.

Figure 8:
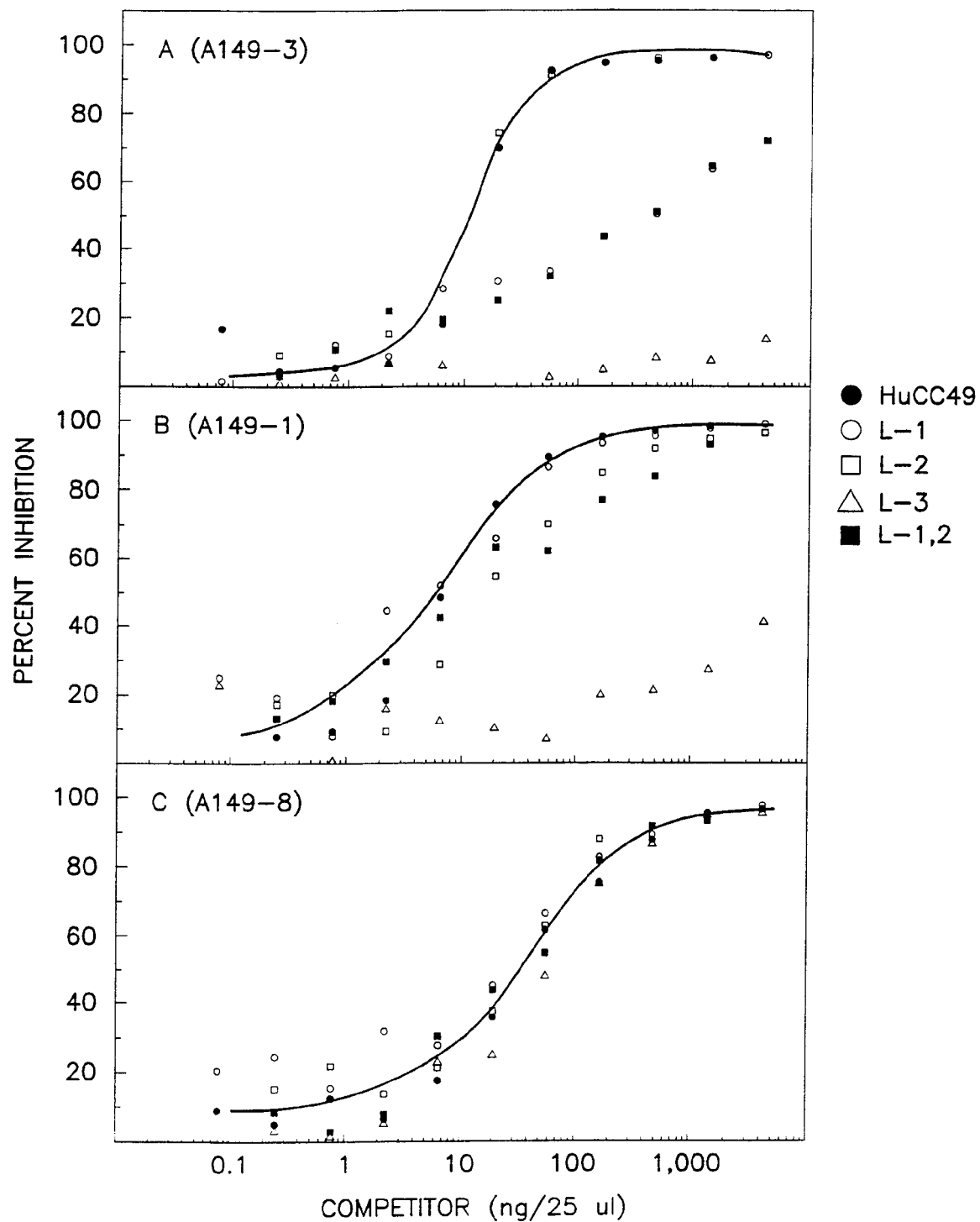
FIG. 8 shows the effect of light chain CDRs on binding of anti-idiotypic MAbs. The HuCC49 CDR variants were characterized in a competition RIA with $^{125}$I-HuCC49 and CC49 anti-idiotypic MAbs AI49-3 (panel A), AI49-1 (panel B) and AI49-8 (panel C). The competitors were: HuCC49, L-1, L-2, L-3, L-1,2.

The results for the light chain variants are shown in FIG. 8. For the AI49-3 (Θ-subset): L-CDR1 appears to be only partially involved in the recognition of CC49 by AI49-3; L-CDR2 does not appear to be involved in the recognition of CC49 by AI49-3; and L-CDR3 appears to be important for recognition of CC49 by AI49-3. For the AI49-1 (K-subset): L-CDR1 appears to be not required for recognition of CC49 by AI49-1; L-CDR2 appear to be only modestly involved in the recognition of CC49 by AI49-1; and L-CDR3 appears to be important for recognition of CC49 by AI49-1. For the AI49-8 (I-subset): neither L-CDR1, L-CDR2, nor L-CDR3 appear to have any influence on the interaction of AI49-8 with CC49.

Figure 9:
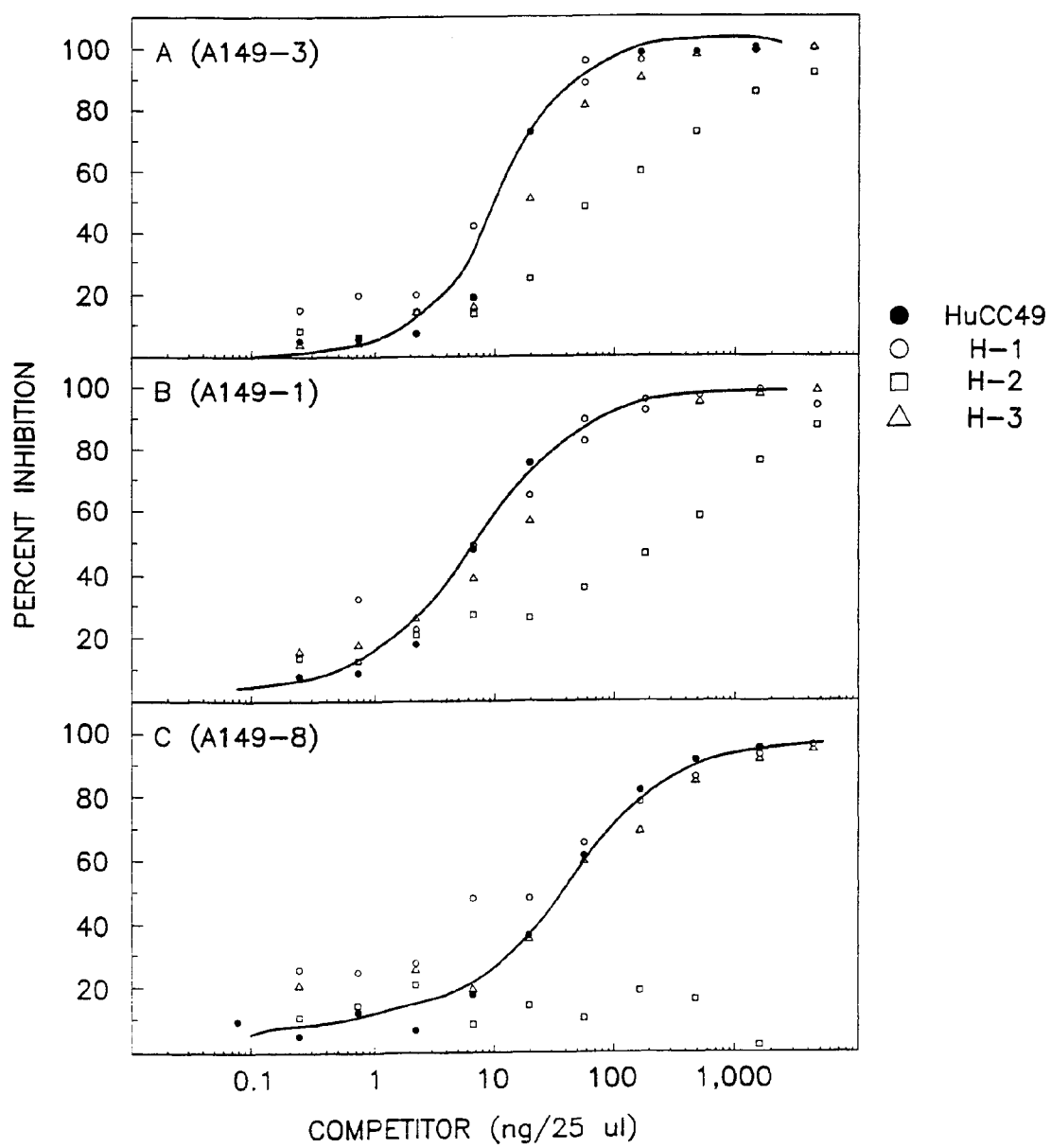
FIG. 9 shows the effect of heavy chain CDRs on binding of anti-idiotypic MAbs. The HuCC49 CDR variants were characterized in a competition RIA with $^{125}$I-CC49 and CC49 anti-idiotypic MAbs AI49-3 (panel A), AI49-1 (panel B) and AI49-8 (panel C). The competitors were: HuCC49, H-1, H-2, H-3.

The results for the heavy chain variants are shown in FIG. 9. For the AI49-3 (Θ-subset): H-CDR1 and H-CDR3 do not appear to be involved in binding of HuCC49 to AI49-3, while H-CDR2 appears to be important for recognition of CC49 by AI49-3 (approximately 4-15 times more competitor is required for 50% inhibition by H-2 as compared to HuCC49). For the AI49-1 (K-subset): H-CDR1 and H-CDR3 do not appear to be involved in binding of HuCC49 to AI49-1, while H-CDR2 appears to be important for recognition of CC49 by AI49-1 (approximately 4-15 times more competitor is required for 50% inhibition by H-2 as compared to HuCC49). For the AI49-8 (I-subset): H-CDR1 and H-CDR3 do not appear to be involved in binding of HuCC49 to AI49-8, while H-CDR2 appears to be important for recognition of CC49 by AI49-8 (there is a complete loss of inhibition by the variant).

An analysis of patient reactivity to the variants of HuCC49 show that three of the 6 CDRs (L-CDR2, H-CDR1 and H-CDR3) do not seem to be recognized by the patient, while L-CDR1 and H-CDR2 appear to be involved in the patient's recognition of HuCC49 to some degree. L-CDR3 (which is important for antigen binding) is the immunodominant CDR recognized by the patient. L-CDR3 is immunodominant in mice as well (AI49-1 and AI49-3, the two anti-idiotypic antibodies that inhibit antigen binding of HuCC49, require L-CDR3 for recognition of HuCC49).

Example V

High Performance Liquid Chromatography

The CDR variants were further characterized using the serum from a patient that had received $^{177}$Lu-CC49 in a phase 1 radioimmunotherapy clinical trial (Mulligan et al., (1995) *Clin. Cancer Res.*, 1: 1447-1454. Several of the patients in this study were found to have anti-idiotypic antibodies to MAb CC49. One patient was selected to perform a preliminary study to identify whether any of the CC49 CDRs were immunodominant.

Using a modification of the method reported by Colcher et al., (1990) *J. Nucl. Med.*, 31:1133-1142 and Mulligan et al., (1995) *Clin. Cancer Res.*, 1: 1447-1454, serial dilutions of the purified CDR variants were incubated with the patient's sera along with $^{125}$I-labeled HuCC49. Specifically, the method of Colcher and Mulligan was modified as follows: prior to the study, HAMA and TAG-72 were removed from the sera by adsorption with CC92 conjugated solid support. The amount of sera required for half maximal complex formation with HuCC49 was then determined. Specifically, 8 Tl of patient sera was mixed with >500,000 cpm of $^{125}$I-HuCC49 and serial dilutions of purified HuCC49 or its variants. The preparations were brought to a final volume of 50 Tl.

The ability of the variants to inhibit complex formation of the patent sera with $^{125}$I-labeled HuCC49 was monitored using HPLC analysis. 25 Tl of each solution was applied to a TSK3000 analytical column (7.8 mm×30 cm; Tosohaas, Montgomeryville, Pa.) and eluted at 0.5 ml/min with 100 mM KCl in 67 mM sodium phosphate (pH 6.8). Radioactivity was monitored using a flow-through K-scintillation detector (Model 170, Beckman).

If the variant contained the CDR recognized by the patient, then the variant would compete with the radiolabeled HuCC49 and complex formation would not occur and there would not be an alteration in the retention time of the $^{125}$I-HuCC49. If the variant no longer contained a CDR recognized by the patient, then complex formation would result. Thus, the ability of the CDR variants to inhibit complex formation of the patient sera with the radiolabeled HuCC49 was determined by the retention time of the $^{125}$I-HuCC49. The percent inhibition of complex formation was calculated and plotted versus concentration of each competitor to evaluate the degree of the patient's reactivity with the individual CDR variants. FIG. 15 shows a comparison of patient reactivity with HuCC49 and CDR variants.

L-1 (variant without CC49 L-CDR1) showed some inability to inhibit complex formation. Thus L-CDR1 appears to be somewhat involved in immunogenicity (0.7 Tg of competitor was required for 50% inhibition of complex formation).

L-2 appeared to compete better than parental HuCC49 by 2 fold (an enhanced recognition by the patient)

L-3 showed no inhibition of complex formation, thus L-CDR3 appears necessary for immunogenicity L-1,2 demonstrated some inability to inhibit complex formation, indicating that L-CDR1 and/or L-CDR2 are somewhat involved in immunogenicity.

H-1 inhibits complex formation and therefore contributes to immunogenicity.

H-2 showed little complex formation, thus H-CDR2 does not appear to be necessary for immunogenicity (10 Tg of competitor was unable to achieve 50% inhibition of complex formation).

H-3 demonstrated some inability to inhibit complex formation, thus H-CDR3 appears to be somewhat involved in immunogenicity (0.4 Tg of competitor was required for 50% inhibition of complex formation).

Example VII

Preparation of SDR Substituted MAb CC49

Padlan et al., (1995) *FASEB J.*, 9:133-139 disclose that the SDRs of light chain are bounded by positions 27d and 34; 50 and 55; and 89 and 96. The heavy chain SDRs are contained within positions 31 and 35b; 50 and 58; and 95 and 101.

FIG. 2 shows the differences between the amino acid residues of the light chain CDRs of CC49 and LEN, and the heavy chain CDRs of CC49 and 21/28'CL.

In L-CDR1, CC49 and LEN differ in three residues; at positions 27b, 27f and 29. The residues at positions 27b (a buried residue) and 27f were found not to be directly involved in ligand contact, while the one at position 29 was found to interact with ligand in two complexes; in one only by main chain atoms. Residue 27b is located outside the suggested SDR boundaries. Residues 27f and 29 are well within the suggested SDR boundaries.

In L-CDR2, CC49 and LEN differ at position 53 only, and this position was found to be involved in ligand contact in only three of the 31 complexes of known structure. Residue 53 is well within the suggested SDR boundaries.

Since L-CDR1 and 2 of CC49 were replaced with their counterparts from LEN without any significant loss of antigen binding reactivity (above), it was concluded that residues 27b, 27f, 29 and 53 were not important for binding of CC49 to its antigen. L-CDR1 and L-CDR2 of CC49 were not considered for the mutation experiments because they were replaced with the corresponding CDRs of the human MAb LEN without significant loss of antigen binding reactivity.

The immunodominant L-CDR3 of CC49 differs from LEN at three positions, 94, 96 and 97. Each of the three residues of CC49 L-CDR3 was replaced with the residue present at the corresponding position in the LEN CDR to generate light chain variants $^{94}$L, $^{96}$L and $^{97}$L, respectively. Another light chain variant, $^{94,97}$L was generated carrying two substitutions, one at position 94 and the other at 97. Two additional variants were derived from the HuCC49 light chain variant $L_{1,2}$, in which the L-CDR1 and L-CDR2 of CC49 were earlier replaced with their counterparts from the human MAb LEN. One variant, $^{97}L_{1,2}$, carried a single substitution at position 97. The other, $^{94,97}L_{1,2}$, had substitutions at two positions, 94 and 97.

Of the three residues that differ between L-CDR3 of CC49 and LEN, a partially buried residue at position 97 was not important for the antigen binding activity of CC49. This residue is not located within the suggested boundary of SDRs of the L-CDR3. Thus, variant $^{97}$L did not show any loss in antigen binding activity. Variant $^{97}L_{1,2}$ showed only an insignificant loss of antigen binding activity.

Positions 94 and 96 of L-CDR3 are involved in ligand contact in 19 and 22 known antibody:antigen complexes, respectively. Thus it was consistent that variants $^{96}$L and $^{94}$L suffered total and near total loss of antigen binding reactivity. When the mutation at position 94 was imposed on the variants $^{97}$L and $^{97}L_{1,2}$, it destroyed their antigen binding function.

H-CDR1 of CC49 and 21/28'CL differ at three positions, 31, 32 and 34. The residue at position 31 is directly involved in ligand binding in 12 of the 31 complexes; in five of those, only main chain atoms were involved. The residue at position 32 is ligand contacting in eight of the 31 complexes of known structure. The residue at position 34 is involved in ligand contact in none of the 31 complexes of known structure. Residues at positions 32 and 34 of the CC49 H-CDR1 were replaced with the corresponding residues of 21/28'CL MAb ($^{32,34}$H) to test whether position 32 is important for ligand contact and in eliciting anti-idiotypic response.

H-CDR2 of CC49 differs from human MAb 21/28'CL at eleven positions. The residues at positions 60, 61, 62 and 64 were not ligand contacting in any of the complexes of known structure. Therefore, these residues of CC49 were prime candidates for replacement. Accordingly, a heavy chain variant of HuCC49, $^{60-62,64}$H, was generated by replacing these residues of HuCC49 with their counterparts in human MAb 21/28'CL.

H-CDR3 was not considered for mutations, because it did not show any reactivity to patient's sera (above).

The following SDR variants were made:

Variant $^{94}$L: residue 94 of CC49 L-CDR3 was replaced with the residue present at the corresponding position in LEN.

Variant $^{96}$L: residue 96 of CC49 L-CDR3 was replaced with the residue present at the corresponding position in LEN.

Variant $^{97}$L: residue 97 of CC49 L-CDR3 was replaced with the residue present at the corresponding position in LEN.

Variant $^{94,97}$L: residue 94 and 97 of CC49 L-CDR3 was replaced with the residue present at the corresponding position in LEN.

Variant $^{97}L_{1,2}$: derived from the HuCC49 light chain variant $L_{1,2}$, in which the L-CDR1 and L-CDR2 of CC49 were replaced with their counterparts from the human MAb LEN; residue 97 of CC49 L-CDR3 was replaced with the residue present at the corresponding position in LEN.

Variant $^{94,97}L_{1,2}$: derived from the HuCC49 light chain variant $L_{1,2}$, in which the L-CDR1 and L-CDR2 of CC49 were replaced with their counterparts from the human MAb LEN; residues 94 and 97 of CC49 L-CDR3 were replaced with the residue present at the corresponding position in LEN.

Variant $^{32,34}$H: residues at positions 32 and 34 of the CC49 H-CDR1 were replaced with the corresponding residues of 21/28'CL MAb.

Variant $^{60-62,64}$H: residues at positions 60, 61, 62 and 64 of the CC49 H-CDR2 were replaced with the corresponding residues of 21/28'CL MAb.

Production of Oligomers

The oligomers were produced essentially as described in Example 1. pLgpCXHuCC49HuK1, the expression construct for parental HuCC49 heavy chain genes was used as the template for heavy ($^{32,34}$H and $^{60-62,64}$H) chain variant gene synthesis. pLNCXHuCC49HuK, the expression construct of the parental HuCC49 light chain gene was used as a template for the light ($^{94}$L, $^{96}$L, $^{97}$L and $^{94,97}$L) chain variant gene synthesis. Variants $L_1$ and $L_{1,2}$ were developed by replacing only the L-CDR1 or both L-CDR1 and L-CDR2 of CC49, respectively, with their LEN counterparts. For the synthesis of $^{94}L_{1,2}$ and $^{94,97}L_{1,2}$ genes, an expression construct of the $L_{1,2}$ variant in a baculoviral expression construct was used as a template.

Mutagenic oligonucleotide primers, ranging in size from 37 to 56 nucleotides, were synthesized using a Model 8700 DNA synthesizer (Milligen/Bioresearch, Burlington, Vt.). They were purified on oligo-Pak columns (Milligen/Bioresearch) according to the supplier's recommendation. The sequences of the mutagenic primers were as follows, where the mutagenic changes are underlined:

$V_L$ CDR3:

(SEQ ID NO: 27)
5'-GCC AGC GCC GAA <u>GCT</u> GAG GGG ATA GCT ATA ATA CTG CTG ACA-3'

(SEQ ID NO: 28)
5'-GGT GCC AGC GCC GAA <u>GCT</u> GAG GGG <u>GGT</u> GCT ATA ATA CTG CTG ACA-3'

-continued (SEQ ID NO: 29)
5'-GCC ACG GCC GAA TGT GTA GGG ATA GCT ATA ATA CTG
CTG ACA-3'

(SEQ ID NO: 30)
5'-GCC GAA TGT GAG GGG GGT GCT ATA ATA CTG CTG ACA
ATA-3'

$V_H$ CDR1:

(SEQ ID NO: 31)
5'-GTT TCA CCC AGT GCA TTG CAT AAT CAG TGA AGG TGT
A-3'

$V_H$ CDR2:

(SEQ ID NO: 32)
5'-GTG GCC TTG CCC TGG AAC TTC TGT GAG TAC TTA AAA
TCA TCG TTT CCG GGA GAG AA-3'

Example VIII

Assembly of PCR Products

The PCR products were assembled and sequenced as described in Example II. The 425 base pair (bp) PCR product obtained using the HuCC49 light chain construct as a template carried sequences encoding the leader peptide, the CC49 $V_L$ domain and the amino terminus of the kappa (κ) constant region, terminating in a SacII site located 10 bp downstream of the $V_L$. Similarly, the 432 base pair (bp) PCR product from the heavy chain template encompassed sequences encoding the leader, the $V_H$ and the amino terminus of the $C_H1$ domain, extending to the ApaI site, which is located 17 bp downstream from the start of the $C_H1$ domain.

Generation of Recombinant SDR Substituted CC49 MAb

SDR substituted variants were generated essentially as described Example III, except for the following. The Sf900-II medium included 50 Tg/ml of antibiotic, gentamicin and the infectious supernatants were harvested six days after transfection.

Purification of SDR Substituted CC49 MAb

Three days after infection, the tissue culture supernatant was harvested and clarified by centrifugation at 2000×g for 10 minutes. Tris buffer was added to the supernatant to a final concentration of 20 mM. Following incubation at 4° C. for 2-3 hours, any contaminating proteins were pelleted by centrifugation at 10,000×g for 15 minutes. The supernatant was applied to a protein G agarose column (Gibco BRL) and the bound protein was eluted from the column, using 0.1 M glycine hydrochloride, pH 2.5. The pH of the eluted material was immediately adjusted to 7.0 with 1.0 M Tris buffer, pH 8.0. The protein was concentrated using a Centriplus 30 microconcentrator (Amicon, Beverly, Mass.), centrifuged at 3000×g for 80 minutes. The concentrated protein was recovered in phosphate-buffered saline (PBS). The protein concentration was determined by the as described in Example III. The purity of the antibody preparation was evaluated by electrophoresis on 4-12% SDS-PAGE, under reducing and non-reducing conditions. The proteins were visualized by staining with Coomassie blue, as described in Example III.

Example IX

Competition Radioimmunoassays for SDR Substituted Variants

ELISA

The ability of the variants to express immunoglobulin molecules and their antigen reactivity of the heavy ($^{32,34}$H and $^{60-62,64}$H) or variant light ($^{94}$L, $^{96}$L, $^{97}$L, $^{94,97}$L, $^YL_{1,2}$ and $^{94,97}L_{1,2}$) chain variants was evaluated using ELISA assays. ELISA assays were carried out by coating individual wells of a 96-well polyvinyl microtiter plates with 1 Tg/well of TAG-72 positive bovine submaxillary mucin (BSM) (Sigma Chem. Co., St. Louis, Mo.), and following the procedure described by Bei et al., (1995) *J. Immunol. Methods*, 186:245-255.

Not all variant antibodies were positive for antigen binding activity. Results of the ELISA assay for the binding activity to the TAG-72 positive BSM showed that the variant antibodies specified by expression constructs carrying the variant genes $^{32,34}$H and $^{96}$L were not reactive with BSM. In contrast, variant antibodies expressed by $^{97}$L and $^{60-62,64}$H constructs showed strong BSM binding activity. While immunoglobulin molecules expressed by $^{94}$L and $^{94}L_{1,2}$ constructs showed moderate positive antigen binding reactivity, those expressed by $^{94,97}L_{1,2}$ were only weakly positive. (FIG. 13)

A partial or complete loss of antigen binding activity of the variant immunoglobulins might be attributed to the detrimental effect of the SDR substitutions on the combining site of HuCC49. Alternatively, the plaques may show lower or no antigen binding reactivity because some of the expression constructs failed to express, were expressing at significantly lower level, or producing antibodies that were not physically normal. To examine these possibilities, variant antibodies were produced and purified from a larger batch of cells that were freshly infected with inoculum derived from the highest producing clone for each of the constructs. The concentration of the secreted variant antibodies in culture supernatants ranged between 2-3 Tg/ml. Purified immunoglobulin molecules were characterized by SDS-PAGE. Under reducing conditions, immunoglobulin molecules expressed by each of the constructs yielded two bands that co-migrated with the heavy and light chains of HuCC49 MAb (data not shown) Antibodies produced by the insect cells harboring expression constructs $^{97}L_{1,2}$ and $^{94,97}L_{1,2}$ genes paired with the HuCC49 heavy chain gene showed similar results (data not shown). These results make it evident that all constructs expressed and produced comparable levels of immunoglobulin molecules of appropriate size. Therefore, it can safely be concluded that the variant HuCC49 MAbs carrying $^{96}$L and $^{32,34}$H substitutions suffered a total loss of antigen binding activity.

Competition Radioimmunoassay

Competition radioimmunoassays (RIAs) were performed to determine relative binding of the variant MAbs and the parental HuCC49 to BSM. Details of the procedure are described by Kashmiri et al., (1995) *Hybridoma*, 14:461-473. Serial dilutions of the purified unlabeled variant antibodies or the parental HuCC49 MAb were used to compete with radiolabeled HuCC49 for binding to the TAG-72 positive BSM. Briefly, 25 Tl of serial dilutions of the purified SDR substituted variants or the parental HuCC49 in PBS containing 1% BSA were added to wells of 96-well microtiter plates containing 10 ng of BSM. 25 Tl of $^{125}$I-labeled HuCC49 (50,000 cpm) was added to each well to compete with the unlabeled parental or variant HuCC49 for binding to the BSM coated on the plates. The plates were incubated overnight at 4° C. and then washed and counted in a K-scintillation counter.

Competition profiles of the light chain variants presented in panel A show that the variant $^{96}$L failed to compete, while all other variants antibodies competed with the parental HuCC49 completely and with similar slopes. (FIG. 13) However, the competition curves of all variants with the exception of $^{97}$L were shifted significantly to the right, indicating a loss of reactivity with antigen (BSM). This shift was notably less pronounced for $^{97}$L$_{1,2}$. Similarly, it is evident from the competition profiles of the heavy chain variants (panel B) that the variant MAb $^{32,34}$H, with substitutions in H-CDR1, did not inhibit binding of HuCC49 MAb to BSM, whereas $^{60-62,64}$H, the variant with substitutions in the H-CDR2, competed completely with a profile that was almost identical to that of the parental HuCC49.

The relative affinity constants were calculated as described in Example IV. The relative affinity constants (Ka) of the variants were calculated from the linear parts of the competition curves. The Ka of $^{97}$L and $^{60-62,64}$H MAbs were 3.6×10$^8$ M$^{-1}$ and 2.2×10$^8$ M$^{-1}$, respectively. These values are comparable to 3.2×10$^8$ M$^{-1}$, the Ka of the parental HuCC49. The variant $^{97}$L$_{1,2}$ was found to have a Ka of 1.4×10$^8$ M$^{-1}$, which is approximately 2- to 3-fold less than the Ka of HuCC49 MAb.

Two new expression constructs were then generated and expressed in Sf9 cells; in one of them, the gene encoding the variant heavy chain $^{60-62,64}$H was paired with the gene encoding the light chain variant $^{97}$L. Gene $^{60-62,64}$H was paired with the $^{97}$L$_{1,2}$ light chain gene in the other construct. Competition profiles of the purified antibodies show that these variant MAbs competed completely with HuCC49 MAb for antigen binding, yielding competition curves of the same slope as HuCC49. (FIG. 13) The relative affinity constant of the Variant MAb $^{97}$L/$^{60-62,64}$H was 5.48×10$^8$ M$^{-1}$, a figure favorably comparable to that of HuCC49, while the Ka of the variant MAb $^{97}$L$_{1,2}$/$^{60-62,64}$H was 1.15×10 M$^{-1}$, which is about 3-fold less than that of the parental HuCC49 MAb.

Example X

High Performance Liquid Chromatography

In a reported Phase I clinical trial, in which $^{177}$Lu-labeled MAb CC49 was administered to adenocarcinoma patients, several patients were found to have anti-idiotypic antibodies to MAb CC49. Sera collected from the study was used to examine the potential immunogenicity of the variants. The sera was obtained by separating the blood by centrifugation. High Performance Liquid Chromatography (HPLC) was used to determine antigen reactivity of the variants by monitoring complex formation between antibodies in the patient sera and the variant MAbs.

Prior to HPLC analysis, any free TAG-72 and human anti-murine antibodies other than anti-idiotypic antibodies to CC49 present in the sera were absorbed out using MAb CC92 conjugated to a solid support. MAb CC92 is a murine anti-TAG-72 antibody which as the same isotype as CC49 and recognizes an epitope of TAG-72 other than that recognized by CC49. Patient sera was then incubated with $^{125}$I-labeled HuCC49 (approximately 500,000 cpm) and 5 Tg of the cold competitor; either HuCC49 or one of the variant MAbs.

The competition assay is described in Example V. Briefly, patient sera was mixed with >0.3 TCi of $^{125}$I-HuCC49 and serial dilutions of purified HuCC49 or its variants. Prior to the assay, the amount of sera required in half-maximal immune complex formation was determined. The mixture was brought to a final volume of 50 Tl. 25 Tl of the final solution was applied to a 7.8 mm×30 cm TSK3000 analytical column (Tosohaas, Montgomeryville, Pa.) and eluted at 0.5 ml/min with elution buffer (100 mM KCl in 67 mM sodium phosphate, pH 6.8). Radioactivity was monitored using a flow-through Model 170 K-scintillation detector (Beckman).

Complex formation of the radiolabeled HuCC49 with the anti-idiotypic antibodies in patient sera reduced the retention time of the radiolabel on the column. The ability of the variant to inhibit complex formation with $^{125}$I-labeled HuCC49 was determined by the differential in the retention time of the radiolabel on HPLC column, when a mixture of sera and $^{125}$I-labeled HuCC49 was loaded on the column with or without incubation with the cold competitor. Inhibition of complex formation by a competitor indicates that the competitor shares the immunogenic epitope with HuCC49. (FIG. 14)

From an analysis of the percent of input counts recovered as a complex, when a mixture of $^{125}$I-labeled HuCC49 and sera from each of the four patients was incubated with 5 Tg of cold competitor and subjected to HPLC analysis, it is evident that the variant antibodies $^{97}$L and $^{32,34}$H, like HuCC49, inhibited complex formation. In contrast, the variant MAbs $^{96}$L and $^{94,97}$L$_{1,2}$, like the nonspecific Human immunoglobulin did not inhibit complex formation of HuCC49 with sera from any patient except EA. Complex formation with EA sera was partially inhibited by the two variants. The variant MAbs $^{94}$L, $^{94,97}$L, $^{97}$L$_{1,2}$ and $^{60-62,64}$H inhibited complex formation only partially with sera from all patients. The variant $^{97}$L/$^{60-62,64}$H, whose antigen binding activity was comparable to that of parental HuCC49, inhibited sera of three patients (DG, CP and DS) only partially, but completely inhibited the sera from EA patient to form complexes with HuCC49. More importantly, the variant $^{97}$L$_{1,2}$/$^{60-62,64}$H did not compete with HuCC49 to form complex with anti-idiotypic antibodies present in sera from two patients (CP and DS) while showing only partial competition with sera from two other patients (DG and DS).

Using serial dilutions of the competitors, competition profiles were developed to determine the relative amounts of unlabeled competitor antibodies required to achieve 50% competition of the binding of $^{125}$I-labeled HuCC49 to the anti-idiotypic antibodies present in sera from one of the patients (CP). The percent inhibition of complex formation was calculated and plotted versus the concentration of competitor.

The competition profiles show that the cold HuCC49 competed completely and it required approximately 250 ng of the parental HuCC49 antibody to achieve 50% competition. In contrast, variant $^{97}$L$_{1,2}$/$^{60-62,64}$H inhibited binding of the radiolabeled HuCC49 to the sera anti-idiotypic antibodies only minimally; even 1 Tg of the variant failed to achieve more than 25% competition, that was achieved by 60 ng of HuCC49. This variant, which retains moderate antigen binding activity and reacts with patient's sera only minimally, might be most advantageous for clinical applications. This variant was further studied for plasma clearance and biodistribution in an animal model.

FIG. 16 is a graph showing the immunoreactivity of variant $^{97}$L$_{1,2}$/$^{60-62,64}$H to human sera containing anti-murine CC49 variable region antibodies as assessed by HPLC analysis. The percent inhibition of the complex formation was calculated and plotted versus ng of the competitors. The competitors were HuCC49 (■) and variant (□).

Example XI

Biodistribution and Pharmacokinetic Studies

Pharmacokinetics

Since the rate of plasma clearance has a bearing on in vivo tumor targeting, a comparison of the pharmacokinetics of the variant to the parental HuCC49 was assessed using the procedures described by Kashmiri et al., (1995) *Hybridoma*, 14:461-473.

To study pharmacokinetics, athymic mice bearing TAG-72 positive LS-174T tumors (Colcher et al., (1983) *Cancer Res.*, 43:736-742) were injected intravenously in the tail vein with a mixture containing 1.4 TCi $^{131}$I-labeled HuCC49 and 4.4 TCi $^{125}$I-labeled variant MAb $^{97}L_{1,2}/^{60-62,64}H$. Blood samples were collected at various time points via the tail vein into 10 Tl heparinized capillary tubes (Drummond, Broomall, Pa.). The amounts of $^{131}$I and $^{125}$I in the plasma were determined and corrected for the respective rates of the decay of the two radionuclides. The percentage of the injected dose of each radionuclide remaining in the plasma was then calculated for each time point. The results suggest that the blood clearance patterns of the two antibodies are not significantly different. (FIG. 17). For 50% of the injected dose of the HuCC49 or variant to clear the blood compartment, required 1 and 2 hours, respectively. At 24 hours, 85% and 80% of the radiolabeled HuCC49 and the variant, respectively, was cleared from the blood. At 48 hours, the percentage of HuCC49 and the variant cleared from the blood was 92% and 88%, respectively.

Biodistribution

Biodistribution assays were performed as described by Kashmiri et al., (1995) *Hybridoma*, 14:461-473. To investigate the ability of the variant HuCC49 MAb to localize to human tumor xenograft and determine radiolocalization index (RI), athymic mice bearing TAG-72 positive LS-174T tumors (Colcher et al., (1983) *Cancer Res.*, 43:736-742) were injected intravenously in the tail vein with a mixture containing 1.4 TCi $^{131}$I-labeled HuCC49 and 4.4 TCi $^{125}$I-labeled variant MAb $^{97}L_{1,2}/^{60-62,64}H$. The amount of $^{131}$I and $^{125}$I were determined in blood samples collected via tail vein at specified times. For each time point, 5 mice were sacrificed to collect and weigh tumor, blood and all other major organs. Radioactivity was measured in a K-scintillation counter and it was corrected for the decay. The percentage of the injected dose per gram (% ID/gm) for each organ was determined.

The % injected dose of the two antibodies per gram of either tumor or different normal tissues that were collected at different time points shows that the biodistribution patterns of the two antibodies are essentially the same. Both showed significant tumor localization by 24 hours. (FIG. 18) By 48 hours, when only 8% and 12% of the injected dose was present in the blood, 17.6% and 23.8% ID/b of HuCC49 and the variant were, respectively, present in the tumor.

Example XII

Characterization of Humoral Immune Response against CC49

In this Example, the humoral immune response against HuCC49 CDR-replacement variants is examined.

Generation of Humanized CC49 (HuCC49) and Humanized CC49 CDR-Replacement Variants (CDR Variants)

A clone producing humanized CC49 (HuCC49) was grown in protein free hybridoma medium PFHM-II (GIBCO-BRL, Gaithersburg, Md.) as described by Kashmiri (1995), *Hybridoma*, 14:461-473. The humanized CC49 monoclonal antibody (MAb) was purified from the tissue culture supernatant by Protein G affinity chromatography as described by Kashmiri (1995), *Hybridoma*, 14:461-473.

Seven HuCC49 CDR-variants were produced as described in Examples I-III.

Radiolabeling

MAb HuCC49, BL-3 and the CDR-replacement variants of HuCC49 were labeled with Na $^{125}$I, using the iodogen method (Pierce, Rockford, Ill.) as described by Fraker et al. (1978), *Biochem. Biophys. Res. Commun.* 80:849-857; and Colcher et al. (1988), *Cancer Res.*, 48:4597-4603. BL-3 is an isotype-matched control for CC49 (described by Colcher et al. (1987), *Cancer Res.*, 47:4218-4224). The labeling procedure typically resulted in specific activities of 5-10 TCi/Tg.

Patients and Sample Collection

Patients with recurrent metastatic adenocarcinoma were enrolled in a Phase I Study to assess the maximum tolerated does of intravenously administered $^{177}$Lutetium radiolabeled MAb CC49 (Mulligan, (1995) *Clin. Cancer Res.* 1: 1447-1454).

In the Phase I Study, adenocarcinoma patients were given a test dose of 0.1 mg (i.v. bolus) of MAb CC49 and observed for 30 minutes prior to administration of the $^{177}$Lu-labeled MAb CC49. The radiolabeled MAb was given as a 1 hour i.v. infusion. Blood samples were collected prior to and at the end of the infusion, and 0.5, 1 and 2 hours after the infusion, and afterward, daily for 7 days. Patients returned for a follow-up examination 10 at 3, 6 or 8 weeks, at which time blood samples were collected. Sera was separated and stored at −20° C. until analyzed. Sera from these patients provided a resource for assessing the humoral response of patients to the murine MAb CC49. The patient characteristics are presented in Table 1, below.

TABLE 1

Patient Characteristics

| Dose Level | Patient | Age | Sex | Tumor | Dose[a] mCi | mg MAb |
|---|---|---|---|---|---|---|
| 10 mCi/m² | DS | 52 | F | Breast | 16.0 | 20 |
|  | LW | 45 | F | Breast | 19.0 | 20 |
|  | JJ | 61 | F | Breast | 17.2 | 20 |
| 25 mCi/m² | DG | 45 | F | Breast | 41.0 | 20 |
|  | LJ | 45 | F | Breast | 40.3 | 20 |
|  | JM | 42 | F | Breast | 45.4 | 20 |
| 15 mCi/m² | JG | 61 | M | Colon | 29.8 | 44 |
|  | RW | 46 | F | Lung | 24.2 | 20 |
|  | TD | 50 | M | Colon | 31.5 | 47 |
|  | EA[b] | 53 | F | Colon | 24.2 | 20 |
|  | CP[b] | 53 | F | Colon | 26.0 | 20 |
|  | LQ[b] | 45 | F | Colon | 29.7 | 20 |

[a]Patients were administered $^{177}$Lu-PA-DOTA-CC49 by intravenous injection.
[b]Patient received new formulation of $^{177}$Lu-PA-DOTA-CC49 that was labeled using a modification of the method described by Mulligan et al. (1995), Clin. Cancer Res. 1: 1447-1454.

PA-DOTA was conjugated to human serum albumin (HSA), radiolabeled with Na $^{125}$I, incubated with the patient sera and analyzed for immune complex formation by size-exclusion HPLC. None of the sera showed detectable reactivity with the PA-DOTA-HSA conjugate (Data not shown).

Determination of Patient Humoral Response

The sera from the twelve patients was evaluated for the presence of human anti-murine antibodies (HAMA) in response to MAb CC49 using high performance liquid chromatograph (HPLC) as described by Mulligan et al. (1996) *Clin. Cancer Res.*, 1:1447-1454. The analysis was performed by adding about 500,000 cpm (0.4TCi) of $^{125}$I-BL-3 to 50 Tl of patient sera. Following a 60 minute incubation at 37° C., 25 Tl of the mixture was applied to a size-exclusion column (TSK 3000SW; TosoHaas, Montgomeryville, Pa.) equilibrated in 67 mM sodium phosphate (pH 6.8) containing 100 mM KCl. The sera samples were eluted at a flow rate of 0.5 ml/min. The protein was detected by absorbance at 280 nm and the radioactivity was measured using a flow-through K-scintillation counter (Model 170, Beckman Instruments, Inc., Berkeley, Calif.). The presence of HAMA was indicated by a shift in the elution profile of the $^{125}$I-BL-3 because the formation of immune complexes with the radiolabeled BL-3 results in a shorter retention time. The patients' pre-study sera, normal human sera and phosphate buffered saline with $^{125}$I-BL-3 were used as controls. A patient with a known HAMA response from a previous study (Colcher et al. (1990), J. Nucl. Med., 31:1133-1142) served as a positive control. The patients' sera were demonstrated to have antibodies against the variable region of the murine CC49.

FIG. 19 shows an HPLC analysis of patient HAMA following intravenous injection of $^{177}$Lu-CC49. Serum samples from LQ were analyzed for the presence of HAMA at various timepoints before and after injection with 20 mg of $^{177}$Lu-labeled CC49. Pre-study sera (A), sera collected at 7 days (B), 3 weeks (C), and 6 weeks (D) were mixed with $^{125}$I-BL-3 and applied to a size exclusion column. Reduction in retention time of the radiolabeled BL-3 as compared to migration of the $^{125}$I-BL-3 in buffer (E) were indicative of immune complex formation and therefore the presence of HAMA.

Lack of complex formation is evident (FIG. 19A) when the pre-study sera of Patient LQ is incubated with the $^{125}$I-BL-3. All of the radioactivity is associated with the peak at about 18.5 minutes, the same retention time for $^{125}$I-BL-3 in buffer (FIG. 19E). Complex formation is also absent when the sera collected at seven days is incubated with $^{125}$I-BL-3 (FIG. 19B). With sera collected at 3 weeks (FIG. 19C), however, there is an indication of complex formation (46%) with the appearance of two peaks with a shorter retention time (i.e., 14 and 16 minutes). The peaks at a shorter retention time indicate the development of a higher molecular weight species in the sera. At 6 weeks (FIG. 19D), the HAMA response has increased, the amount of radioactivity bound in complexes is now 66%.

FIG. 20 shows an HPLC analysis of patients' humoral response to the variable region of MAb CC49. The percent complex formation has been plotted versus time for (solid lines) patients DS (○), LW (□), JJ (△), DG (●), LJ (■), TD(▲); (dotted lines) JG (○), RW (□), JM (△), EA (●), CP (■), LQ (▲);

At one week, none of the patients showed a detectable response against the HuCC49 (FIG. 20). At 3 weeks, sera from nine of the twelve patients (75%) appears to contain antibody against the variable region of CC49 with one patient having a notably higher response than the others. For the eleven patients evaluated at six weeks, only two patients did not elicit a human antivariable region antibody response (HAVRA) against CC49, i.e., 9 of 11 evaluable patients (82%) had antibody against the variable region of the murine MAb CC49.

Three patterns of HAMA-HAVRA response are evident. The patterns of the HAMA and HAVRA responses elicited in each of the patients were very similar, differing only in the apparent level of antibody. Patients DG, LW, LQ and CP developed HAVRA simultaneously with HAMA. Patients DS and JM appear to have a strong HAVRA, while HAMA response is modest. While in patients TD, JG, and EA, the HAVRA level is lower than HAMA at 3 weeks, followed by HAMA and HAVRA attaining high levels at later timepoints. In no patient was there a HAVRA response without the development of HAMA.

The HAMA results for the twelve patients are summarized below in Table 2.

TABLE 2

HPLC Analysis of Patients' Anti-mouse immunoglobulin response after i.v. injection of $^{177}$Lu-CC49

| Patient | Days Post-Injection of $^{177}$Lu-CC49 | | | |
| --- | --- | --- | --- | --- |
| | 7 | 21 | 42 | 56 |
| DS | 0$^a$ | 1 | 16 | 27 |
| LW | 3 | 6 | 81 | NA |
| JJ | 0 | 12 | 3 | 4 |
| DG | 0 | 24 | 84 | NA |
| LJ | 0 | 42 | NA | NA |
| JM | 0 | 8 | 47 | NA |
| JG | 4 | 83 | 83 | NA |
| RW | 0 | 1 | 2 | NA |
| TD | 0 | 95 | 100 | NA |
| EA | 0 | 27 | 100 | 100 |
| CP3 | 0 | 33 | 27 | NA |
| LQ | 0 | 46 | 66 | 100 |

$^a$The values are the percent of $^{125}$I-BL-3 detected in complexes after a brief incubation with the patient sera and resolved by size-exclusion chromatography. The timepoints of each patient are background corrected using the patients' pre-study sera.

The patterns of the HAMA responses are varied and are consistent with previous findings by Colcher et al. (1990), J. Nucl. Med. 31:1133-1142. Ten out of the twelve patients (83%) demonstrate a HAMA response at 3 weeks following a single intravenous injection of 20 mg $^{177}$Lu-labeled CC49, two patients (LW and JG) have minimal responses evident at 7 days with complexes of 3% and 4%, respectively. One patient (RW) may be considered a nonresponder. Some of the patients show an escalating HAMA response, while others plateau. Yet another (JJ) peaks at 3 weeks, followed by an apparent decrease in the HAMA level. Overall, at 3 weeks, 8 of 12 patients (57%) at and 6 weeks, 9 of 11 (82%) were HAMA positive.

Specificity of Patient Response

The specificity of the patients' antibody response to CC49 was assessed using $^{125}$I-labeled HuCC49 and HuCC49 CDR-replacement variants to determine whether or not any of the responses were directed against the variable region of CC49. To accomplish this, the HPLC methodology was employed using $^{125}$I-HuCC49 as the probe (See, Kashmiri et al. (1995), Hybridoma, 14:461-473).

To eliminate the artifactual influence of TAG-72 in the HPLC analysis for anti-CC49 antibody responses found in the patient's serum, immunoadsorbents were prepared as reported by Ferroni et al. (1992) J. Clin. Lab. Analysis, 4:465-473. For the purpose of these studies, purified MAb CC92 was coupled to Reacti-gel (HW65F, Pierce) according to the method of Heam et al. (1979), J. Chromatog, 185:463-470. MAb CC92 is a second-generation monoclonal antibody that reacts with TAG-72, but with an epitope distinct from the one recognized by CC49.

Before probing the patients' sera with the $^{125}$I-HuCC49, removal of HAMA and circulating TAG-72 were confirmed using $^{125}$I-BL-3 and $^{125}$I-B72.3, respectively (data not shown). MAb B72.3 is an anti-TAG-72 MAb that has been shown to form complexes with TAG-72 in patient sera (Colcher et al. (1990), J. Nucl. Med., 31:1133-1142).

In the competition assay, 5 Tg of the cold competitor (either purified HuCC49 or one of its variants) was added to a mixture of patient sera (collected 8 weeks post-i.v. injection with $^{177}$Lu-CC49) and $^{125}$I-HuCC49 and then analyzed by size-exclusion chromatography for the absence or presence of complexes. The percent inhibition of complex formation was calculated. If the variant competed with the $^{125}$I-labeled MAb, and complex formation was inhibited, then the variant still contained the immunodominant CDR. If the variant failed to inhibit complex formation, then the CDR that is no longer present in the variant is recognized by the patient and hence it is an immunogenic CDR. An example of this assay (using serum from patient LQ) is shown in FIG. 21. Panel A is the profile of the HuCC49 in buffer only. Panel B, is the profile showing complex formation (42.9%) resulting from patient sera (LQ) incubated with $^{125}$I-HuCC49. When HuCC49 is added as a competitor, there is competition for the $^{125}$I-HuCC49 and a loss or absence of complexes is observed (Panel C). The same is true of a variant which still contains an immunogenic CDR (e.g., light chain CDR2 as the competitor) (Panel D). In contrast, there is either a partial (Panel F) or total retention of the complexes (Panel E), when light chain CDR1 or CDR3 variants, respectively, are the competitors.

The results are very striking, see Table 3.

TABLE 3

HPLC Analysis of Patient Reactivity to CDR-Replacement variants of HuCC49[a]

| Competitor | | Patient | | | | | |
|---|---|---|---|---|---|---|---|
| | CDR[b] | DS | DG | JG | EA | CP | LQ |
| None | — | 33.5[c] | 46.2 | 24.5 | 56.8 | 32.2 | 42.9 |
| HuCC49 | — | 0 | 0 | 2.6 | 0.5 | 1.5 | 3.0 |
| Hu IgG | — | 46.4 | 59.0 | 25.1 | 63.6 | ND | 54.1 |
| Light Chain | 1 | 16.0 | 12.2 | 9.8 | 10.1 | 16.9 | 14.3 |
| | 2 | 2.7 | 3.4 | 2.7 | 4.4 | 3.0 | 2.4 |
| | 3 | 34.8 | 48.2 | 22.4 | 37.6 | 33.5 | 46.7 |
| | 1, 2 | 24.6 | 24.5 | 12.6 | 19.4 | 15.7 | 20.2 |
| Heavy Chain | 1 | 10.2 | 3.9 | 3.3 | 7.0 | 5.8 | 3.5 |
| | 2 | 32.7 | 32.5 | 12.7 | 24.7 | 29.7 | 36.6 |
| | 3 | 7.3 | 5.1 | 3.7 | 8.2 | 6.7 | 4.6 |

[a]The sera from patients injected with $^{177}$Lu-CC49 were tested for reactivity with variants of HuCC49 in which individual CDRs had been substituted with human sequences in both the heavy and light chains of HuCC49. Five Tg of the purified CDR-replacement variants were added to a mixture of $^{125}$I-HuCC49 and the patient sera and then analyzed for the presence or absence of immune complex formation.
[b]The number indicates which CDR in the HuCC49 has been replaced with a human CDR sequence.
[c]The values are the percent of complexes, the higher molecular weight species, resolved by size-exclusion chromatography.

Of the six patients analyzed, all six demonstrated reactivity with CDR3 light chain indicating that light chain CDR3 may be immunodominant in murine CC49 MAb. In the heavy chain, CDR2 appears to be dominant but not with the same level of consensus (four of the six patients show the same level of reactivity, the other two demonstrated partial reactivity). Concordance was obtained among the six patients in regard to CDR2 of the light chain and CDR1 and CDR3 of the heavy chain, which do not appear to contribute to the immunogenicity of the MAb. This is also the case with the light chain CDR1 and, it follows, the variant with the dual substitution of CDR1 and 2 in the light chain, in which all six patients displayed a partial recognition of the variants. Partial recognition with the heavy chain CDR2 variant with two patients may be due to a loss of part but not all of the cognizant epitope, a change in the conformation or conformational epitope, or loss of amino acid residues that might stabilize the antibody:antibody interaction.

Quantitation of Patient Antibody Response

Quantitation of the HAMA or anti-variable region antibody levels in four patients was performed using HPLC analysis. The quantitation study was performed by adding either 500 ng of unlabeled BL-3 or 250 ng of HuCC49, respectively, to the mixture of patient serum and $^{125}$I-HuCC49 and calculating the amount of BL-3 or HuCC49 bound in complexes.

As shown in Table 4, below, at 6 weeks, the amount of HAMA varies from patient to patient by 43-fold, while the variability of HAVRA is within 4-fold. Furthermore, the HAMA versus HAVRA levels may vary from 10 to 145-fold. Clearly, HAVRA can be detected at 3 weeks, and, not surprisingly, it does not appear to attain the same levels as HAMA. In patient EA, there is a dramatic 1 0-fold increase in the level of HAVRA from 6 to 8 weeks that is noteworthy.

TABLE 4

Quantitation of anti-CC49 variable region and anti-murine response of patients administered $^{177}$Lu-CC49

| | | Tg of Ab/ml Sera | |
|---|---|---|---|
| Patient | Post-Mab Injection | BL-3[a] | HuCC49[b] |
| EA | 0 | 0 | 0 |
| | 3 weeks | 4.1 | 0.3 |
| | 6 weeks | 289.0 | 2.3 |
| | 8 weeks | 314.4 | 21.6 |
| CP | 0 | 0 | 0 |
| | 3 weeks | 16.0 | 0.8 |
| | 5 weeks | 25.2 | 0.7 |
| | 6 weeks | 23.2 | 0.7 |
| LQ | 0 | 0 | ND |
| | 3 weeks | 4.61 | 0.4 |
| | 6 weeks | 6.64 | 0.7 |
| | 8 weeks | ND | 1.7 |
| JG | 0 | 0 | 0 |
| | 3 weeks | 58.6 | 0.7 |
| | 6 weeks | 47.8 | 2.6 |

Competition Radioimmunoassay

To confirm whether the HAVRA was actually an anti-idiotypic response, including internal image anti-idiotypic antibodies, to the murine MAb CC49, the sera from one patient (EA) was selected and assessed for blocking of the binding of $^{125}$I-HuCC49 to BSM in a radioimmunoassay.

The immunoreactivity of the radiolabeled MAbs was assessed using bovine submaxillary mucin (BSM) immobilized on a solid support (Reacti-Gel HW65, Pierce) as a modification of the method reported by Heam et al. (1979), *J. Chromatog.*, 185:463-470 and Schott (1992) *Cancer Res.*, 52:6413-6417. Briefly, 15 bovine submaxillary mucin (BSM), which is TAG-72 positive, was adsorbed to each well of a 96-well polyvinylchloride microtiter plate at 10 ng in 50Tl of phosphate buffered saline (pH 7.2) as described by Horan Hand et al. (1992), *Cancer Immunol. Immunother.*, 353: 165-174. After treating the wells with 5% BSA in PBS, serial dilutions of the patient sera (25 Tl in 1% BSA in PBS) were added to each; $^{125}$I-CC49 (38 nCi in 25 Tl) was also added. Following an 18 hour incubation at 4° C., the plates were washed and the wells counted in a K-scintillation counter. The percent inhibition was calculated and compared to that of unlabeled CC49. Human IgG (Organon Teknika, Durham, N.C.), which does not react with TAG-72 was included as a control antibody.

It was found that the patient sera could block the binding of $^{125}$I-HuCC49 with BSM (FIG. 22) suggesting that the patient, in actuality, demonstrates an anti-idiotypic response, consisting of the internal image anti-idiotypic antibodies. Furthermore, the anti-idiotypic response was observed to increase over an eight week period. FIG. 22 shows the detection of patient (EA) anti-idiotypic antibody response to murine CC49: pre-study sera from patient EA (ô); sera collected at 3 weeks (A), 6 weeks (B), and 8 weeks (C).

All references cited in this disclosure are hereby incorporated by reference.

We claim:

1. A recombinant nucleic acid sequence encoding a humanized anti-TAG-72 antibody, wherein the humanized anti-TAG-72 antibody comprises:
   a light chain Complementarity Determining Region (L-CDR)1, a L-CDR2, and a L-CDR3; and a heavy chain Complementarity Determining Region (H-CDR) 1, a H-CDR2, and a H-CDR3,
   wherein L-CDR3, H-CDR1, H-CDR2 and H-CDR3 are parental HuCC49 antibody Complementarity Determining Regions (CDRs), and wherein (i) L-CDR1 is from the human monoclonal LEN antibody and L-CDR2 is from the parental HuCC49 antibody, (ii) L-CDR1 is from the parental HuCC49 antibody and L-CDR2 is from the human monoclonal LEN antibody, or (iii) L-CDR1 and L-CDR2 are from the human monoclonal LEN antibody,
   wherein the human monoclonal LEN antibody L-CDR1 has the amino acid sequence set forth as SEQ ID NO: 7 and the human mononoclonal LEN antibody L-CDR2 has the amino acid sequence set forth as SEQ ID NO: 8, and
   wherein the humanized anti-TAG-72 antibody retains binding affinity for TAG-72 and has reduced immunogenicity, as compared to the parental HuCC49 antibody.

2. The recombinant nucleic acid sequence of claim 1, wherein L-CDR1 is the human monoclonal LEN antibody L-CDR1.

3. The recombinant nucleic acid sequence of claim 1, wherein L-CDR2 is the human monoclonal LEN antibody L-CDR2.

4. The recombinant nucleic acid sequence of claim 1, wherein both L-CDR1 and L-CDR2 are human monoclonal LEN antibody L-CDR1 and L-CDR2, respectively.

5. A recombinant nucleic acid sequence comprising a promoter sequence operably linked to the recombinant nucleic acid sequence of claim 1.

6. A recombinant vector comprising the recombinant nucleic acid sequence of claim 5.

7. A cultured host cell transformed with the recombinant vector of claim 6.

8. A recombinant nucleic acid sequence encoding a humanized anti-TAG-72 antibody, wherein the humanized anti-TAG-72 antibody comprises:
   a light chain Complementarity Determining Region (L-CDR)1, a L-CDR2, and a L-CDR3; and a heavy chain Complementarity Determining Region (H-CDR) 1, a H-CDR2, and a H-CDR3,
   wherein LCDR3, H-CDR1, H-CDR2 and H-CDR3 are of the parental HuCC49 antibody, L-CDR1 is the human monoclonal LEN antibody L-CDR1 having the amino acid sequence set forth as SEQ ID NO: 7, and L-CDR2 is the human monoclonal LEN antibody L-CDR2 having the amino acid sequence set forth as SEQ ID NO: 8, and wherein at least one amino acid at position 60, 61, 62, or 64 in the parental HuCC49 H-CDR2 is replaced with an amino acid at a corresponding position in the human mononoclonal 21/28'CL antibody H-CDR2 having an amino acid sequence set forth as SEQ ID NO: 11, wherein the humanized anti-TAG-72 antibody retains binding affinity for TAG-72 and has reduced immunogenicity, when compared to the parental HuCC49 antibody.

9. The recombinant nucleic acid sequence of claim 8, wherein an asparagine at position 60 in the parental HuCC49 H-CDR2 is replaced with a serine, a glutamic acid at position 61 in the parental HuCC49 H-CDR2 is replaced with a glutamine, an arginine at position 62 in the parental HuCC49 H-CDR2 is replaced with a lysine, and a lysine at position 64 in the parental HuCC49 H-CDR2 is replaced with a glutamine.

10. A recombinant nucleic acid sequence comprising a promoter sequence operably linked to the recombinant nucleic acid sequence of claim 8.

11. A recombinant vector comprising the recombinant nucleic acid sequence of claim 10.

12. A cultured host cell transformed with the recombinant vector of claim 11.

13. A recombinant nucleic acid sequence encoding a humanized anti-TAG-72 antibody, wherein the humanized anti-TAG-72 antibody comprises:

a light chain Complementarity Determining Region (L-CDR)1, a L-CDR2, and a L-CDR3; and a heavy chain Complementarity Determining Region (H-CDR) 1, a H-CDR2, and a H-CDR3, wherein L-CDR3, H-CDR1, H-CDR2 and H-CDR3 are of the parental HuCC49 antibody, L-CDR1 is the human monoclonal LEN antibody L-CDR1 having the amino acid sequence set forth as SEQ ID NO: 7, and L-CDR2 is the human monoclonal LEN antibody L-CDR2 having the amino acid sequence set forth as SEQ ID NO: 8, and wherein a threonine at position 97 in the parental HuCC49 L-CDR3 is replaced with a serine, wherein the humanized anti-TAG-72 antibody retains binding affinity for TAG-72 and has reduced immunogenicity, when compared to the parental HuCC49 antibody.

14. The recombinant nucleic acid sequence of claim 13, wherein at least one amino acid of positions 60, 61, 62, or 64 in the parental HuCC49 H-CDR2 is replaced with an amino acid at a corresponding position in the human monoclonal 21/28'CL antibody H-CDR2 having an amino acid sequence set forth as SEQ ID NO: 11.

15. The recombinant nucleic acid sequence of claim 14, wherein an asparagine at position 60 in the parental HuCC49 H-CDR2 is replaced with a serine, a glutamic acid at position 61 in the parental HuCC49 H-CDR2 is replaced with a glutamine, an arginine at position 62 in the parental HuCC49 H-CDR2 is replaced with a lysine, and a lysine at position 64 in the parental HuCC49 H-CDR2 is replaced with a glutamine.

16. A recombinant nucleic acid sequence comprising a promoter sequence operably linked to the recombinant nucleic acid sequence of claim 14.

17. A recombinant vector comprising the recombinant nucleic acid sequence of claim 16.

18. A cultured host cell transformed with the recombinant vector of claim 17.

19. A recombinant nucleic acid sequence encoding a humanized anti-TAG-72 antibody, wherein the humanized anti-TAG-72 antibody comprises:

a light chain Complementarity Determining Region (L-CDR)1, a L-CDR2, and a L-CDR3; and a heavy chain Complementarity Determining (H-CDR)1, a H-CDR2, and a H-CDR3, wherein L-CDR3, H-CDR1, H-CDR2 and H-CDR3 are of the parental HuCC49 antibody, L-CDR1 is the human monoclonal LEN antibody L-CDR1 having the amino acid sequence set forth as SEQ ID NO: 7, and L-CDR2 is the human monoclonal LEN antibody L-CDR2 having the amino acid sequence set forth as SEQ ID NO: 8, and wherein (1) a threonine is at position 94 in the L-CDR3, or (2) a seine is at position 97 in the L-CDR3, or (3) a threonine is at position 94 and a serine is at position 97 in the L-CDR3, wherein the humanized anti-TAG-72 antibody retains binding affinity for TAG-72 and has reduced immunogenicity, when compared to the parental HuCC49 antibody.

20. A recombinant nucleic acid sequence comprising a promoter sequence operably linked to the recombinant nucleic acid sequence of claim 19.

21. A recombinant vector comprising the recombinant nucleic acid sequence of claim 19.

22. A cultured host cell transformed with the recombinant vector of claim 21.

23. The recombinant nucleic acid of claim 9, wherein a threonine at position 97 of the HuCC49 L-CDR3 is replaced with a serine.

* * * * *

UNITED STATES PATENT AND TRADEMARK OFFICE
CERTIFICATE OF CORRECTION

| | | |
|---|---|---|
| PATENT NO. | : 7,763,719 B2 | Page 1 of 1 |
| APPLICATION NO. | : 11/776437 | |
| DATED | : July 27, 2010 | |
| INVENTOR(S) | : Schlom et al. | |

It is certified that error appears in the above-identified patent and that said Letters Patent is hereby corrected as shown below:

In the Specification:

Column 4, line 16, "21/28°CL" should read --21/28' CL--

Column 4, line 21, "SK" should read --SK$^+$--

Column 6, line 2, "JM A)," should read --JM ($\Delta$),--

Column 10, line 30, "CDRS" should read --CDRs--

Column 12, line 57, "IHI'CL" should read --1H1'CL--

Column 12, line 58, "IBIi'CL" should read --IBII'CL--

Column 14, line 30, "regions SDR heavy" should read --regions. SDR heavy--

Column 25, line 35, "1.15×10 M$^{-1}$" should read --1.15×10$^8$ M$^{-1}$--

Column 28, line 29, "examination 10 at" should read --examination at--

Column 31, line 11, "HuCC49" should read --$^{125}$I-HuCC49--

Column 32, line 45, "Briefly, 15 bovine" should read --Briefly, bovine--

In the Claims:

Claim 19, column 52, line 34, "(2) a seine is at" should read --(2) a serine is at--

Signed and Sealed this
Twelfth Day of February, 2013

Teresa Stanek Rea
*Acting Director of the United States Patent and Trademark Office*

```
                        SEQUENCE LISTING

<160> NUMBER OF SEQ ID NOS: 44

<210> SEQ ID NO 1
<211> LENGTH: 17
<212> TYPE: PRT
<213> ORGANISM: Mus musculus

<400> SEQUENCE: 1

Lys Ser Ser Gln Ser Leu Leu Tyr Ser Gly Asn Gln Lys Asn Tyr Leu
1               5                   10                  15

Ala

<210> SEQ ID NO 2
<211> LENGTH: 7
<212> TYPE: PRT
<213> ORGANISM: Mus musculus

<400> SEQUENCE: 2

Trp Ala Ser Ala Arg Glu Ser
1               5

<210> SEQ ID NO 3
<211> LENGTH: 9
<212> TYPE: PRT
<213> ORGANISM: Mus musculus

<400> SEQUENCE: 3

Gln Gln Tyr Tyr Ser Tyr Pro Leu Thr
1               5

<210> SEQ ID NO 4
<211> LENGTH: 5
<212> TYPE: PRT
<213> ORGANISM: Mus musculus

<400> SEQUENCE: 4

Asp His Ala Ile His
1               5

<210> SEQ ID NO 5
<211> LENGTH: 17
<212> TYPE: PRT
<213> ORGANISM: Mus musculus

<400> SEQUENCE: 5

Tyr Phe Ser Pro Gly Asn Asp Asp Phe Lys Tyr Asn Glu Arg Phe Lys
1               5                   10                  15

Gly

<210> SEQ ID NO 6
<211> LENGTH: 6
<212> TYPE: PRT
<213> ORGANISM: Mus musculus

<400> SEQUENCE: 6

Ser Leu Asn Met Ala Tyr
1               5
```

```
<210> SEQ ID NO 7
<211> LENGTH: 17
<212> TYPE: PRT
<213> ORGANISM: Homo sapiens

<400> SEQUENCE: 7

Lys Ser Ser Gln Ser Val Leu Tyr Ser Ser Asn Ser Lys Asn Tyr Leu
1               5                   10                  15
Ala

<210> SEQ ID NO 8
<211> LENGTH: 7
<212> TYPE: PRT
<213> ORGANISM: Homo sapiens

<400> SEQUENCE: 8

Trp Ala Ser Thr Arg Glu Ser
1               5

<210> SEQ ID NO 9
<211> LENGTH: 9
<212> TYPE: PRT
<213> ORGANISM: Homo sapiens

<400> SEQUENCE: 9

Gln Gln Tyr Tyr Ser Thr Pro Tyr Ser
1               5

<210> SEQ ID NO 10
<211> LENGTH: 5
<212> TYPE: PRT
<213> ORGANISM: Homo sapiens

<400> SEQUENCE: 10

Ser Tyr Ala Met His
1               5

<210> SEQ ID NO 11
<211> LENGTH: 17
<212> TYPE: PRT
<213> ORGANISM: Homo sapiens

<400> SEQUENCE: 11

Trp Ile Asn Ala Gly Asn Gly Asn Thr Lys Tyr Ser Gln Lys Phe Gln
1               5                   10                  15
Gly

<210> SEQ ID NO 12
<211> LENGTH: 12
<212> TYPE: PRT
<213> ORGANISM: Homo sapiens

<400> SEQUENCE: 12

Gly Gly Tyr Tyr Gly Ser Gly Ser Gly Ser Asn Tyr
1               5                   10

<210> SEQ ID NO 13
<211> LENGTH: 113
<212> TYPE: PRT
<213> ORGANISM: Artificial Sequence
<220> FEATURE:
<223> OTHER INFORMATION: Mouse and Human Chimeric Antibody Light Chain
      Variable Region

<400> SEQUENCE: 13
```

```
Asp Ile Val Met Ser Gln Ser Pro Asp Ser Leu Ala Val Ser Leu Gly
1               5                   10                  15

Glu Arg Val Thr Leu Asn Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys
```

```
<210> SEQ ID NO 14
<211> LENGTH: 115
<212> TYPE: PRT
<213> ORGANISM: Artificial Sequence
<220> FEATURE:
<223> OTHER INFORMATION: Mouse and Human Chimeric Antibody Heavy Chain
      Variable Region

<400> SEQUENCE: 14

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser
        115
```

```
<210> SEQ ID NO 15
<211> LENGTH: 124
<212> TYPE: DNA
<213> ORGANISM: Artificial Sequence
<220> FEATURE:
<223> OTHER INFORMATION: VH Oligonucleotide Primer

<400> SEQUENCE: 15
ctaagcttcc accatggagt ggtcctgggt cttcctcttc ctcctgctgc tgtgggtgag      60
agtgcactcc caggtccagc tggtgcagtc cggcgctgag tccctggccg tgtcccaggg     120
cgtg                                                                  124
```

```
<210> SEQ ID NO 16
<211> LENGTH: 123
<212> TYPE: DNA
```

<213> ORGANISM: Artificial Sequence
<220> FEATURE:
<223> OTHER INFORMATION: VH Oligonucleotide Primer

<400> SEQUENCE: 16

```
ggagagaaat atccaatcca ctccaggcgc tgtccaggat tctgtttctt ctgatttccg    60
ctatagagag tgaaggtgta gccgcttgcc ttgcaggaaa tcttcacgcc cagggacacg   120
gcc                                                                 123
```

<210> SEQ ID NO 17
<211> LENGTH: 126
<212> TYPE: DNA
<213> ORGANISM: Artificial Sequence
<220> FEATURE:
<223> OTHER INFORMATION: VH Oligonucleotide Primer

<400> SEQUENCE: 17

```
tggagtggat tggatatttc tctcccggaa acgatgattt aagtacaat gagaggttca     60
agggcaaggc cacactgact gcagacacat ctgccagcac tgcctacgtg agctctcca   120
gcctga                                                              126
```

<210> SEQ ID NO 18
<211> LENGTH: 125
<212> TYPE: DNA
<213> ORGANISM: Artificial Sequence
<220> FEATURE:
<223> OTHER INFORMATION: VH Oligonucleotide Primer

<400> SEQUENCE: 18

```
atgggcccgt agttttggcg ctggagacgg tgaccagggt tccctgtccc cagtaggcca    60
tattcaggga tcttgtgcag aagtacactg cagtatcctc ggatctcagg ctggagagct   120
ccacg                                                               125
```

<210> SEQ ID NO 19
<211> LENGTH: 122
<212> TYPE: DNA
<213> ORGANISM: Artificial Sequence
<220> FEATURE:
<223> OTHER INFORMATION: VL Oligonucleotide Primer

<400> SEQUENCE: 19

```
gcaagcttcc accatggata gccaggccca ggtgctcatg ctcctgctgc tgtgggtgag    60
cggcacatgc ggcgacatcg tgatgagcca gtctccagac tccctggccg tgtcccaggg   120
cg                                                                  122
```

<210> SEQ ID NO 20
<211> LENGTH: 121
<212> TYPE: DNA
<213> ORGANISM: Artificial Sequence
<220> FEATURE:
<223> OTHER INFORMATION: VL Oligonucleotide Primer

<400> SEQUENCE: 20

```
gggctctgcc ctggtttctg ctgataccag gcgagatagt tcttctgatt ccgctatag     60
agcagggact ggctggactt gcaattcaga gtcaccctct cgcccaggga cacggccagg   120
g                                                                   121
```

<210> SEQ ID NO 21
<211> LENGTH: 121

-continued

```
<212> TYPE: DNA
<213> ORGANISM: Artificial Sequence
<220> FEATURE:
<223> OTHER INFORMATION: VL Oligonucleotide Primer

<400> SEQUENCE: 21
gcagaaacca gggcagagcc ctaaactgct gatttactgg gcatccgcta gggaatccgg      60
cgtgcctgat cgcttcagcg gcagcggatc tgggacagac ttcactctga caatcagcag     120
c                                                                      121

<210> SEQ ID NO 22
<211> LENGTH: 126
<212> TYPE: DNA
<213> ORGANISM: Artificial Sequence
<220> FEATURE:
<223> OTHER INFORMATION: VL Oligonucleotide Primer

<400> SEQUENCE: 22
agccgcggcc cgtttcagtt ccagcttggt gccagcgccg aatgtgaggg gatagctata      60
atactgctga caataataga ctgccacgtc ttctgcctgc acgctgctga ttgtcagagt     120
gaagtc                                                                 126

<210> SEQ ID NO 23
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 23
ctaagcttcc accatggag                                                   19

<210> SEQ ID NO 24
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 24
atgggcccgt agtttggcg                                                   19

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 25
gcaagcttcc accatggata                                                  20

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 26
agccgcggcc cgtttcagtt                                                  20

<210> SEQ ID NO 27
```

```
<211> LENGTH: 42
<212> TYPE: DNA
<213> ORGANISM: Artificial Sequence
<220> FEATURE:
<223> OTHER INFORMATION: Mutagenic primer

<400> SEQUENCE: 27
gccagcgccg aagctgaggg gatagctata atactgctga ca                    42

<210> SEQ ID NO 28
<211> LENGTH: 45
<212> TYPE: DNA
<213> ORGANISM: Artificial Sequence
<220> FEATURE:
<223> OTHER INFORMATION: Mutagenic primer

<400> SEQUENCE: 28
ggtgccagcg ccgaagctga gggggggtgct ataatactgc tgaca               45

<210> SEQ ID NO 29
<211> LENGTH: 42
<212> TYPE: DNA
<213> ORGANISM: Artificial Sequence
<220> FEATURE:
<223> OTHER INFORMATION: Mutagenic primer

<400> SEQUENCE: 29
gccacggccg aatgtgtagg gatagctata atactgctga ca                   42

<210> SEQ ID NO 30
<211> LENGTH: 39
<212> TYPE: DNA
<213> ORGANISM: Artificial Sequence
<220> FEATURE:
<223> OTHER INFORMATION: Mutagenic primer

<400> SEQUENCE: 30
gccgaatgtg aggggggtgc tataatactg ctgacaata                       39

<210> SEQ ID NO 31
<211> LENGTH: 37
<212> TYPE: DNA
<213> ORGANISM: Artificial Sequence
<220> FEATURE:
<223> OTHER INFORMATION: Mutagenic primer

<400> SEQUENCE: 31
gtttcaccca gtgcattgca taatcagtga aggtgta                         37

<210> SEQ ID NO 32
<211> LENGTH: 56
<212> TYPE: DNA
<213> ORGANISM: Artificial Sequence
<220> FEATURE:
<223> OTHER INFORMATION: Mutagenic primer

<400> SEQUENCE: 32
gtggccttgc cctggaactt ctgtgagtac ttaaaatcat cgtttccggg agagaa    56

<210> SEQ ID NO 33
<211> LENGTH: 23
<212> TYPE: PRT
<213> ORGANISM: Homo sapiens

<400> SEQUENCE: 33

Asp Ile Val Met Thr Gln Ser Pro Asp Ser Leu Ala Val Ser Leu Gly
```

```
                   1               5                  10                  15
Glu Arg Ala Thr Ile Asn Cys
                   20

<210> SEQ ID NO 34
<211> LENGTH: 15
<212> TYPE: PRT
<213> ORGANISM: Homo sapiens

<400> SEQUENCE: 34

Trp Tyr Gln Gln Lys Pro Gly Gln Pro Pro Lys Leu Leu Ile Tyr
1               5                  10                  15

<210> SEQ ID NO 35
<211> LENGTH: 32
<212> TYPE: PRT
<213> ORGANISM: Homo sapiens

<400> SEQUENCE: 35

Gly Val Pro Asp Arg Phe Ser Gly Ser Gly Ser Gly Thr Asp Phe Thr
1               5                  10                  15

Leu Thr Ile Ser Ser Leu Gln Ala Glu Asp Val Ala Val Tyr Tyr Cys
                   20                  25                  30

<210> SEQ ID NO 36
<211> LENGTH: 10
<212> TYPE: PRT
<213> ORGANISM: Homo sapiens

<400> SEQUENCE: 36

Phe Gly Gln Gly Thr Lys Leu Glu Ile Lys
1               5                  10

<210> SEQ ID NO 37
<211> LENGTH: 30
<212> TYPE: PRT
<213> ORGANISM: Homo sapiens

<400> SEQUENCE: 37

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr
                   20                  25                  30

<210> SEQ ID NO 38
<211> LENGTH: 14
<212> TYPE: PRT
<213> ORGANISM: Homo sapiens

<400> SEQUENCE: 38

Trp Val Arg Gln Ala Pro Gly Gln Arg Leu Glu Trp Met Gly
1               5                  10

<210> SEQ ID NO 39
<211> LENGTH: 32
<212> TYPE: PRT
<213> ORGANISM: Homo sapiens

<400> SEQUENCE: 39

Arg Val Thr Ile Thr Arg Asp Thr Ser Ala Ser Thr Ala Tyr Met Glu
1               5                  10                  15

Leu Ser Ser Leu Arg Ser Glu Asp Thr Ala Val Tyr Tyr Cys Ala Arg
                   20                  25                  30
```

<210> SEQ ID NO 40
<211> LENGTH: 11
<212> TYPE: PRT
<213> ORGANISM: Homo sapiens

<400> SEQUENCE: 40

Trp Gly Gln Gly Thr Leu Val Thr Val Ser Ser
1               5                   10

<210> SEQ ID NO 41
<211> LENGTH: 424
<212> TYPE: DNA
<213> ORGANISM: Artificial Sequence
<220> FEATURE:
<223> OTHER INFORMATION: Mouse and Human Nucleotide Sequences Encoding a
      Chimeric Antibody Light Chain Variable Region Together with
      Flanking Oligomers

<400> SEQUENCE: 41
gcaagcttcc accatggata gccaggccca ggtgctcatg ctcctgctgc tgtgggtgag        60
cggcacatgc ggcgacatcg tgatgagcca gtctccagac tccctggccg tgtcccaggg       120
cgagagggtg actctgaatt gcaagtccag ccagtccctg ctctatagcg aaatcagaa        180 gaactatctc gcctggtatc agcagaaacc agggcagagc cctaaactgc tgatttactg       240
ggcatccgct agggaatccg gcgtgcctga tcgcttcagc ggcagcggat ctgggacaga       300
cttcactctg acaatcagca gcgtgcaggc agaagacgtg gcagtctatt attgtcagca       360
gtattatagc tatccctca cattcggcgc tggcaccaag ctggaactga aacgggccgc       420
ggct                                                                    424

<210> SEQ ID NO 42
<211> LENGTH: 424
<212> TYPE: DNA
<213> ORGANISM: Artificial Sequence
<220> FEATURE:
<223> OTHER INFORMATION: Nucleotide Sequences Complementary to Mouse and
      Human Nucleotide Sequences Encoding a Chimeric Antibody Light
      Chain Variable Region Together with Flanking Oligomers

<400> SEQUENCE: 42
agccgcggcc cgtttcagtt ccagcttggt gccagcgccg aatgtgaggg gatagctata        60
atactgctga caataataga ctgccacgtc ttctgcctgc acgctgctga ttgtcagagt       120
gaagtctgtc ccagatccgc tgccgctgaa gcgatcaggc acgccggatt ccctagcgga       180
tgcccagtaa atcagcagtt tagggctctg ccctggtttc tgctgatacc aggcgagata       240
gttcttctga tttccgctat agagcaggga ctggctggac ttgcaattca gagtcaccct       300
ctcgcccagg gacacggcca gggagtctgg agactggctc atcacgatgt cgccgcatgt       360
gccgctcacc cacagcagca ggagcatgag cacctgggcc tggctatcca tggtggaagc       420
ttgc                                                                    424

<210> SEQ ID NO 43
<211> LENGTH: 434
<212> TYPE: DNA
<213> ORGANISM: Artificial Sequence
<220> FEATURE:
<223> OTHER INFORMATION: Mouse and Human Nucleotide Sequences Encoding a
      Chimeric Antibody Heavy Chain Variable Region Together with
      Flanking Oligomers

<400> SEQUENCE: 43

-continued

```
ctaagcttcc accatggagt ggtcctgggt cttcctcttc ctcctgctgc tgtgggtgag      60
agtgcactcc caggtccagc tggtgcagtc cggcgctgag tccctggccg tgtcccaggg     120
cgtgaagatt tcctgcaagg caagcggcta caccttcact ctctatagcg gaaatcagaa     180
gaaacagaat cctggacagc gcctggagtg gattggatat ttctctcccg gaaacgatga     240 tttaagtac aatgagaggt tcaagggcaa ggccacactg actgcagaca catctgccag      300
cactgcctac gtggagctct ccagcctgag atccgaggat actgcagtgt acttctgcac     360
aagatccctg aatatggcct actggggaca gggaaccctg gtcaccgtct ccagcgccaa     420
aactacgggc ccat                                                      434
```

<210> SEQ ID NO 44
<211> LENGTH: 434
<212> TYPE: DNA
<213> ORGANISM: Artificial Sequence
<220> FEATURE:
<223> OTHER INFORMATION: Nucleotide Sequences Complementary to Mouse and
      Human Nucleotide Sequences Encoding a Chimeric Antibody Heavy
      Chain Variable Region Together with Flanking Oligomers <400> SEQUENCE: 44

```
atgggcccgt agttttggcg ctggagacgg tgaccagggt tccctgtccc cagtaggcca      60
tattcaggga tcttgtgcag aagtacactg cagtatcctc ggatctcagg ctggagagct     120
ccacgtaggc agtgctggca gatgtgtctg cagtcagtgt ggccttgccc ttgaacctct     180
cattgtactt aaaatcatcg tttccgggag agaaatatcc aatccactcc aggcgctgtc     240
caggattctg tttcttctga tttccgctat agagagtgaa ggtgtagccg cttgccttgc     300
aggaaatctt cacgcccagg gacacggcca gggactcagc gccggactgc accagctgga     360
cctgggagtg cactctcacc cacagcagca ggaggaagag gaagacccag gaccactcca     420
tggtggaagc ttag                                                      434
```